(12) United States Patent
Ting et al.

(10) Patent No.: US 10,301,624 B2
(45) Date of Patent: May 28, 2019

(54) TARGETING HUMAN SATELLITE II (HSATII)

(71) Applicant: The General Hospital Corporation, Boston, MA (US)

(72) Inventors: David T. Ting, Dover, MA (US); Daniel A. Haber, Chestnut Hill, MA (US); Shyamala Maheswaran, Lexington, MA (US); Francesca Bersani, Turin (IT); Anders M. Naar, Arlington, MA (US); Mihir Shivadatta Rajurkar, Worcester, MA (US); Sakari Kauppinen, Holte (DK); Andreas Petri, Frederiksberg (DK)

(73) Assignees: The General Hospital Corporation, Boston, MA (US); Aalborg University, Aalborg (DK)

( * ) Notice: Subject to any disclaimer, the term of this patent is extended or adjusted under 35 U.S.C. 154(b) by 0 days.

(21) Appl. No.: 15/321,391

(22) PCT Filed: Jun. 25, 2015

(86) PCT No.: PCT/US2015/037792
§ 371 (c)(1),
(2) Date: Dec. 22, 2016

(87) PCT Pub. No.: WO2015/200697
PCT Pub. Date: Dec. 30, 2015

(65) Prior Publication Data
US 2017/0198288 A1    Jul. 13, 2017

Related U.S. Application Data

(60) Provisional application No. 62/017,012, filed on Jun. 25, 2014.

(51) Int. Cl.
  C12N 15/11    (2006.01)
  A61K 48/00    (2006.01)
  (Continued)

(52) U.S. Cl.
  CPC .......... *C12N 15/113* (2013.01); *C12Q 1/6886* (2013.01); *C12N 2310/11* (2013.01);
  (Continued)

(58) Field of Classification Search
  CPC .............. C12N 15/11; C12N 2310/321; C12N 15/113; C12N 2310/11; C12N 2310/315;
  (Continued)

(56) References Cited

FOREIGN PATENT DOCUMENTS

| EP | 2 119 784 | 11/2009 |
|---|---|---|
| WO | 2004/035819 | 4/2004 |

(Continued)

OTHER PUBLICATIONS

Stump et al. (Nucleic Acids Research, 1999 vol. 27:4642-4648).*

(Continued)

*Primary Examiner* — Terra C Gibbs
(74) *Attorney, Agent, or Firm* — Fish & Richardson P.C.

(57) ABSTRACT

Methods for treating cancer, e.g., cancer of epithelial origin, by specifically targeting human satellite II (HSATII) using sequence specific agents such as oligonucleotides. As shown herein, the hetero chromatic HSATII satellite repeat is silenced in normal cells, but massively over expressed in epithelial cancers and in cancer cell lines when grown as xenografts or in 3D culture. Induction of HSATII RNA, either in xenografts or using in vitro reconstitution models, suggests the appearance of complementary DNA intermediates.

25 Claims, 23 Drawing Sheets
Specification includes a Sequence Listing.

(51) Int. Cl.
    C07H 21/02     (2006.01)
    C07H 21/04     (2006.01)
    C12N 15/113    (2010.01)
    C12Q 1/6886    (2018.01)
(52) U.S. Cl.
    CPC .. C12N 2310/315 (2013.01); C12N 2310/321
        (2013.01); C12N 2310/3231 (2013.01); C12N
            2310/341 (2013.01); C12Q 2600/106
        (2013.01); C12Q 2600/156 (2013.01); C12Q
                            2600/158 (2013.01)
(58) Field of Classification Search
    CPC . C12N 2310/341; A61K 47/60; C12Q 1/6886
    See application file for complete search history.

(56)              References Cited

FOREIGN PATENT DOCUMENTS

| WO | WO 2008/083634 * | 7/2008 | |
|----|------------------|--------|---|
| WO | WO-2009090639 A2 * | 7/2009 | C12N 15/113 |
| WO | 2012/048113 | 4/2012 | |
| WO | WO 2013/035114 | 3/2013 | |
| WO | 2013/063035 | 5/2013 | |

OTHER PUBLICATIONS

Watts et al. (J Pathol, 2012 vol. 226:365-379).*
Azzalin et al., "Telomeric Repeat—Containing RNA and RNA Surveillance Factors at Mammalian Chromosome Ends," Science, Nov. 2007, 318: 798-801.
Bass et al., "Genomic sequencing of colorectal adenocarcinomas identifies a recurrent VTI1A-TCF7L2 fusion," Nat Genet Sep. 2011, 43: 964-968.
Bierhoff et al., "Noisy silence: non-coding RNA and heterochromatin formation at repetitive elements," Epigenetics, Jan. 2014, 9: 53-61.
Black et al., "H3K9/36me3 Demethylase KDM4A Promotes Site-Specific Copy Gain and Re-replication of Regions Amplified in Tumors," Cell, Aug. 2013, 154: 541-555.
Bouzinba-Segard et al., "Accumulation of small murine minor satellite transcripts leads to impaired centromeric architecture and function," PNAS, Jun. 2006, 103: 8709-8714.
Carone et al., "A new class of retroviral and satellite encoded small RNAs emanates from mammalian centromeres," Chromosoma, Feb. 2009, 118: 113-125.
Cheng et al., "Plasma membrane associated transcription of cytoplasmic DNA," PNAS, Jul. 2012, 109: 10827-10831.
Chu et al., "Genomic Maps of Long Noncoding RNA Occupancy Reveal Principles of RNA-Chromatin Interactions," Mol Cell, Nov. 2011, 44: 667-678.
Cohen et al., "Mouse major satellite DNA is prone to eccDNA formation via DNA Ligase IV-dependent pathway," Oncogene, Aug. 2006, 25: 4515-4524.
Crosetto et al., "Nucleotide-resolution DNA double-strand break mapping by next-generation sequencing," Nat Methods, Apr. 2013, 10: 361-365.
Day et al., "Estimating enrichment of repetitive elements from high-throughput sequence data," Genome Biol, 2010, 11: R69.
de Lange, "T-loops and the origin of telomeres," Nat Rev Mol Cell Biol, Apr. 2004, 5: 323-329.
Eymerry et al., "A transcriptomic analysis of human centromeric and pericentric sequences in normal and tumor cells," Nucleic Acids Res, 2009, 37: 6340-6354.
Eymery et al., "The secret message of heterochromatin: new insights into the mechanisms and function of centromeric and pericentric repeat sequence transcription," Int J Dev Biol, 2009, 53: 259-268.
International Preliminary Report on Patentability in International Application No. PCT/US2015/037792, dated Dec. 27, 2016.
Jeanpierre, "Human satellites 2 and 3," Ann Genet, 1994, 37: 163-171.

Jiang et al., "A molecular view of plant centromeres," Trends Plant Sci, Dec. 2003, 8: 570-575.
Lander et al., "Initial sequencing and analysis of the human genome," Nature, Feb. 2001, 409: 8360-921.
Lee et al., "Landscape of Somatic Retrotransposition in Human Cancers," Science, Aug. 2012, 337: 967-971.
Lipson et al., "Quantification of the yeast transcriptome by single-molecule sequencing," Nat Biotechnol, Jul. 2009, 27: 652-658.
Maida et al., "An RNA dependent RNA polymerase formed by hTERT and the RNase MRP RNA," Nature, Sep. 2009, 461: 230-235.
Martinez and Blasco, "Telomeric and extra-telomeric roles for telomerase and the telomere-binding proteins," Nat Rev Cancer, 2011, 11: 161-176.
Martinez et al., "Centromere fission, not telomere erosion, triggers chromosomal instability in human carcinomas," Carcinogenesis, 2011, 32; 796-803.
Masutomi et al., "The telomerase reverse transcriptase regulates chromatin state and DNA damage responses," PNAS, 2005, 102.
Meyne et al., "Distribution of non-telo 1neric sites of the (TT AGGG)n telomeric sequence in vertebrate chromosomes," Chromosoma, 1990, 99: 3-10.
Neumann et al., "Plant centromeric retrotransposons: a structural and cytogenetic perspective," Mobile DNA, 2011, 2: 4.
Ozsolak et al., "Amplification-free digital gene expression profiling from minute cell quantities," Nat Methods, Aug. 2010, 7: 619-621.
Park et al., "Telomerase modulates Wnt signalling by association with target gene chromatin," Nature, Jul. 2009, 460: 66-72.
Peters et al., "Loss of the Suv39h Histone Methyltransferases Impairs Mammalian Heterochromatin and Genome Stability," Cell, Nov. 2001, 107: 323-337.
Plohl et al., "Satellite DNAs between selfishness and functionality: Structure, genomics and evolution of tandem repeats in centromeric (hetero)chromatin," Gene, 2008, 409: 72-82.
Prosser et al., "Sequence relationships of three human satellite DNAs," J Mol Biol., Jan. 1986, 187(2):145-55.
Pushkarev et al., "Single-molecule sequencing of an individual human genome," Nat Biotechnol, Sep. 2009, 27: 847-850.
Richards et al., "The centromere region of Arabidopsis thaliana chromosome 1 contains telomere-similar sequences," Nucleic Acids Res, 1991, 19: 3351-3357.
Rizzi et al., "Transcriptional Activation of a Constitutive Heterochromatic Domain of the Human Genome in Response to Heat Shock," Mol Biol Cell, Feb. 2004, 15: 543-551.
Sharma et al., "2A peptides provide distinct solutions to driving stop-carry on translational recoding," Nucleic Acids Res, Apr. 2012, 40: 3143-3151.
Sharma, "Clinical practice. Barrett's esophagus.," N Engl J Med., 2009, 361(26):2548-56 Erratum in: N Engl J Med. Apr. 15, 2010;362(15): 1450.
Simonet et al., "The human TTAGGG repeat factors 1 and 2 bind to a subset of interstitial telomeric sequences and satellite repeats," Cell Res, 2011, 21: 1028-1038.
Smith, "Evolution of repeated DNA sequences by unequal crossover," Science, Feb. 1976, 191: 528-535.
Tek and Jiang, "The centromeric regions of potato chromosomes contain megabase-sized tandem arrays of telomere-similar sequence," Chromosoma, Sep. 2004, 113: 77-83.
Ting et al., "Aberrant Overexpression of Satellite Repeats in Pancreatic and Other Epithelial Cancers," Science, 2011, 331(6017):593-6.
Villasante et al., "Centromeres were derived from telomeres during the evolution of the eukaryotic chromosome," PNAS, Jun. 2007, 104: 10542-7.
Warburton et al., "Analysis of the largest tandemly repeated DNA families in the human genome," BMC Genomics, 2008, 9:533.
Xi et al., "Copy number variation detection in whole-genome sequencing data using the Bayesian information criterion," PNAS, 2011, 108: E1128-E1136.
Zhdanova et al., "Unusual distribution pattern of telomeric repeats in the shrews Sorex araneus and Sorex granaris," Chromosome Res, Aug. 2005, 13: 617-625.

(56) References Cited

OTHER PUBLICATIONS

Zhu et al., "BRCA1 tumor suppression occurs via heterochromatin mediated silencing," Nature, 2011, 477: 179-184.
International Search Report and Written Opinion dated Oct. 28, 2015 in international application No. PCT/US2015/037792, 12 pgs.
Ting et al, "Aberrant Overexpression of Satellite Repeats in Pancreatic and Other Epithelial Cancers," Science, Feb. 4, 2011 (Feb. 4, 2011), vol. 331, pp. 592-596.
Tahira et al. "Long noncoding intronic RNAs are differentially expressed in primary and metastatic pancreatic cancer," Molecular Cancer, Nov. 13, 2011 (Nov. 13, 2011), vol. 10, No. 141, pp. 1-19.
Alexiadis et al., "RNAPol-ChIP analysis of 1-4 transcription from FSHD-linked tandem repeats and satellite DNA," Biochimica et Biophysica Acta, Jan. 2007, 1769: 29-40.
Bersani et al., "Pericentromeric satellite repeat expansions through RNA-derived DNA intermediates in cancer," PNAS, Nov. 2015, 112: 15148-15153.
Extended European Search Report in Application No. 15811533.7, dated Jan. 8, 2018, 7 pages.
Kususda et al., "Clusterin inhibition using OGX-011 synergistically enhances antitumour activity of sorafenib in a human renal cell carcinoma model," British Journal of Cancer, Jun. 2012, 106: 1945-1952.

* cited by examiner

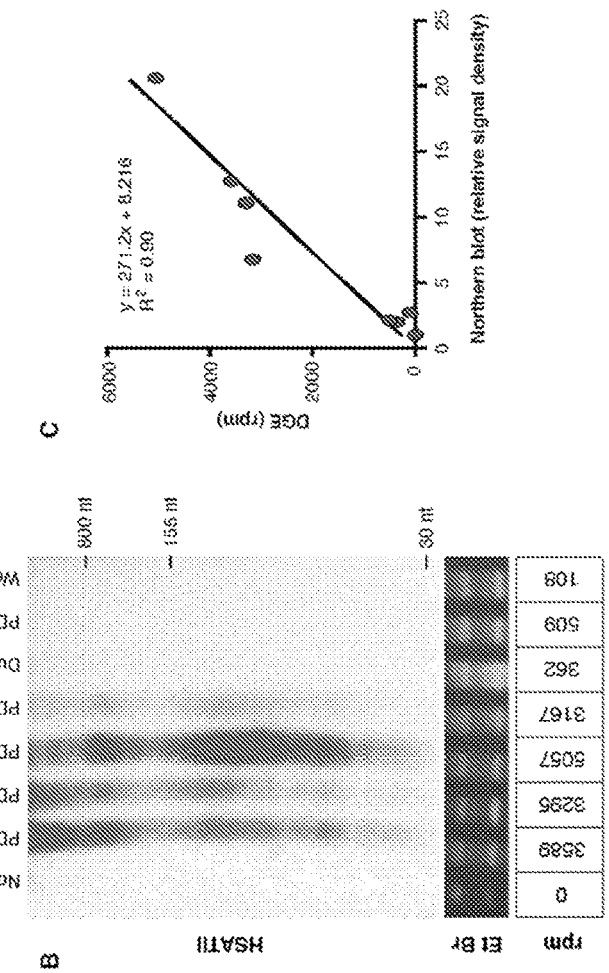
FIGURES 1A-C

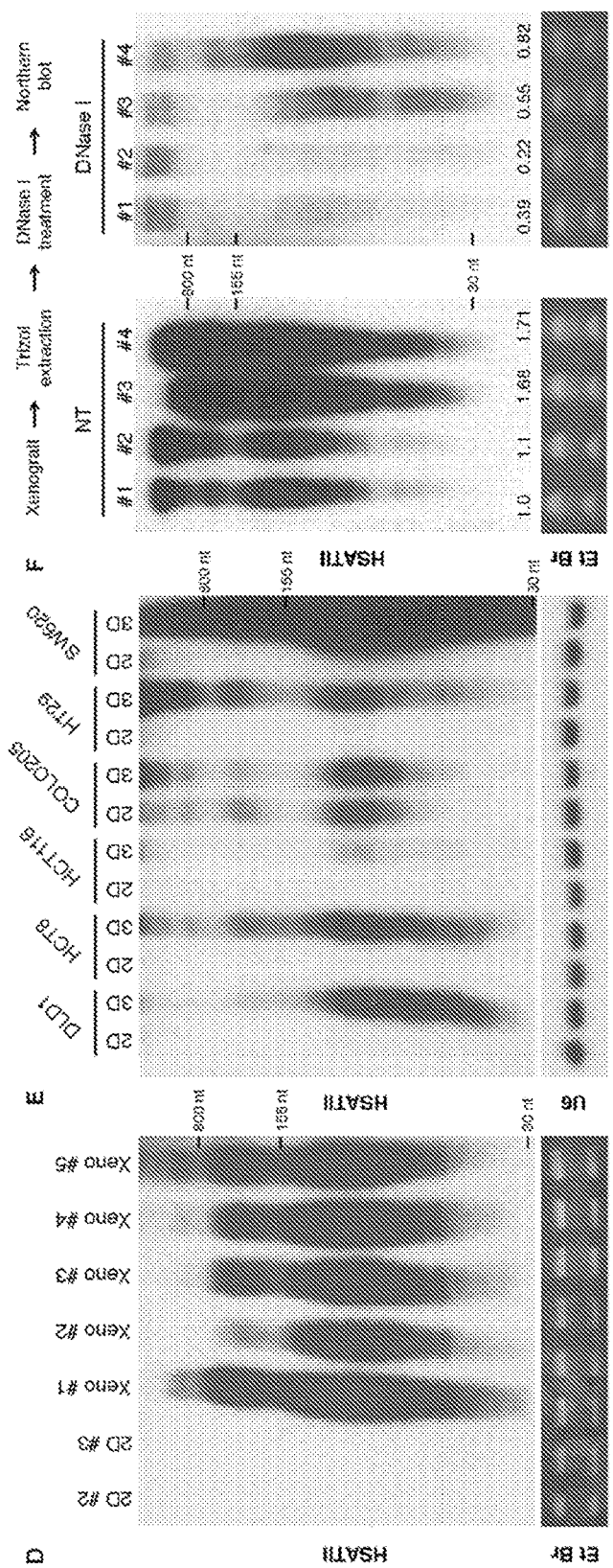
FIGURES 1D-F

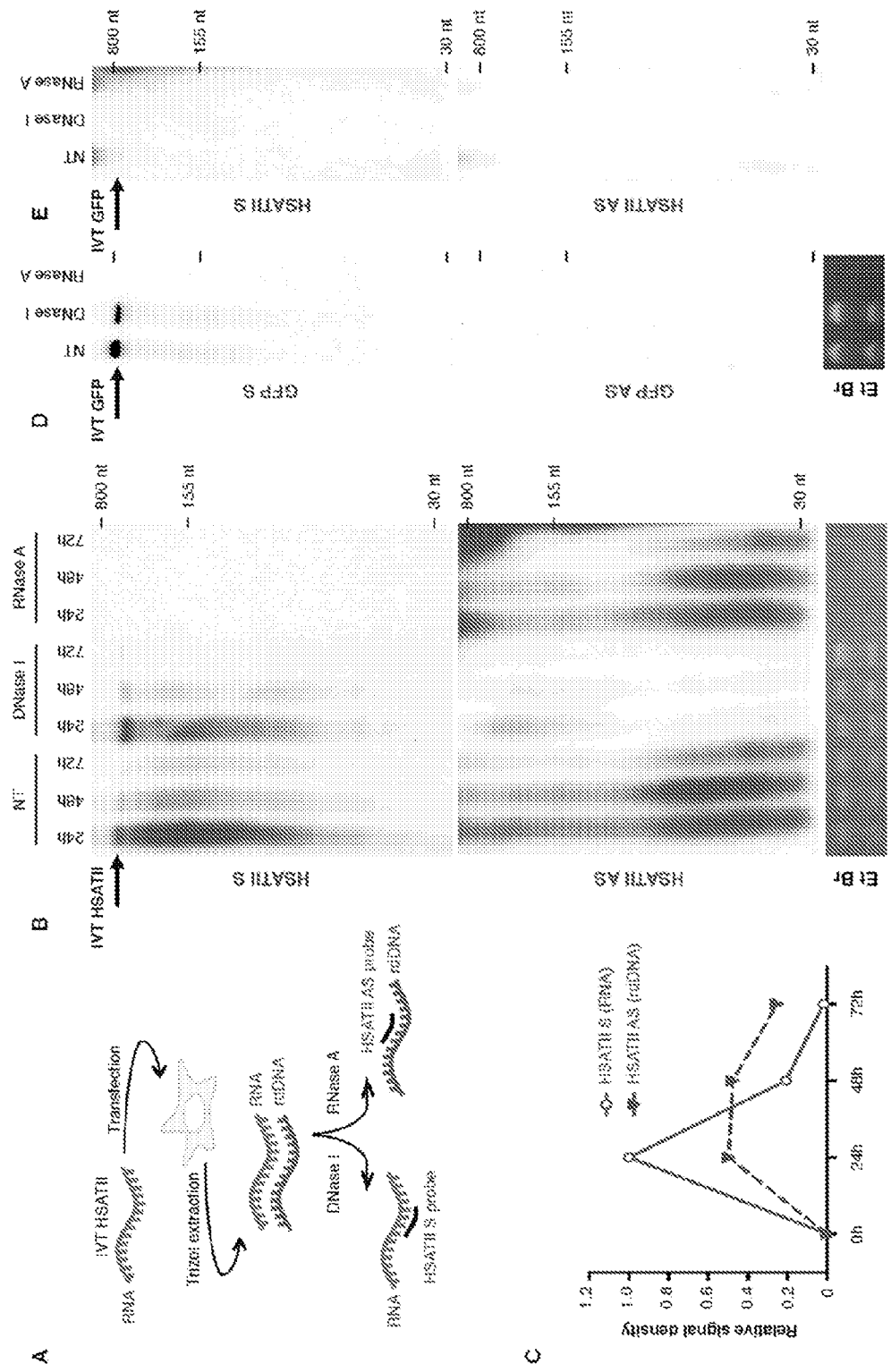
FIGURES 2A-E

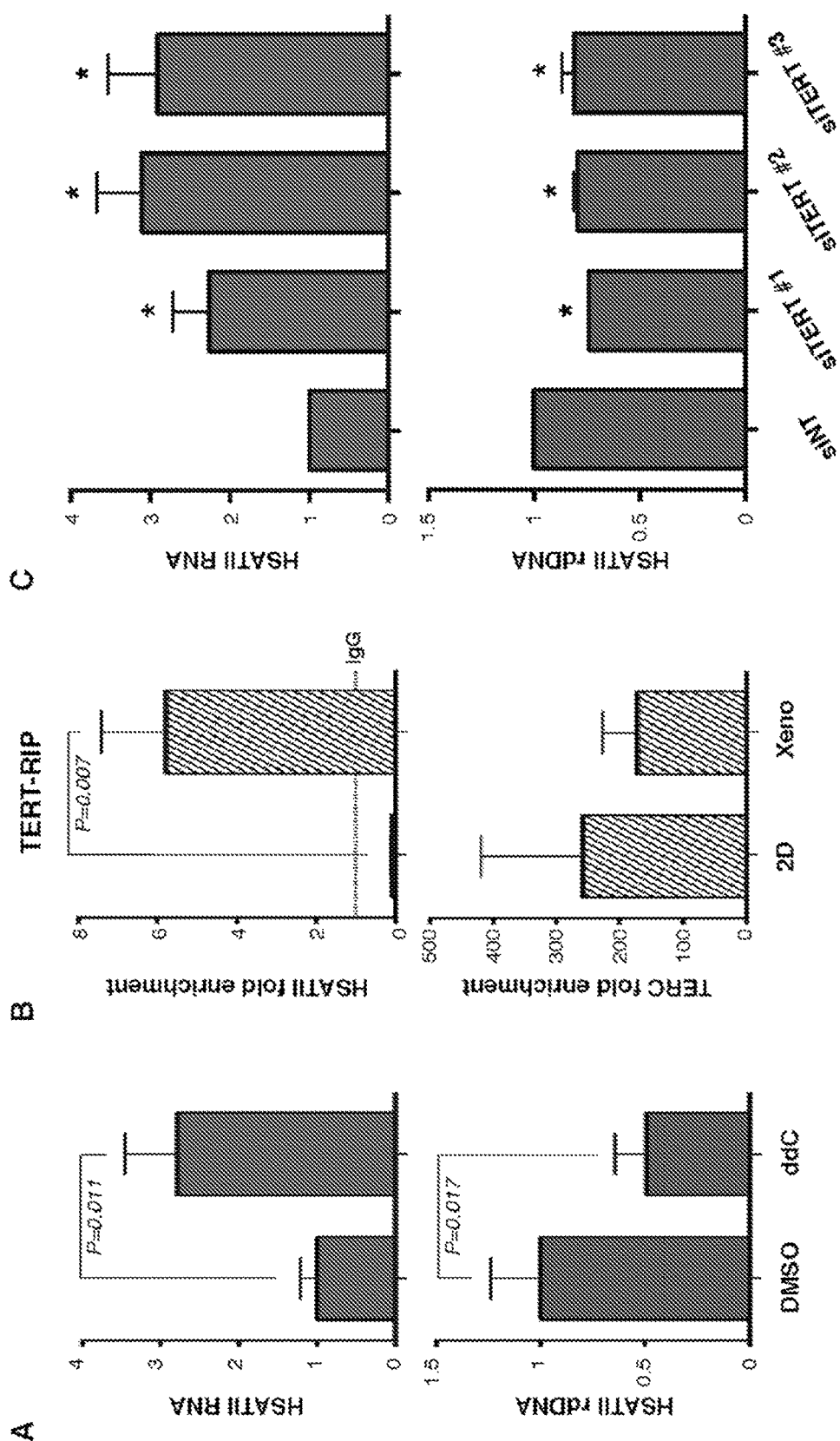
FIGURES 3A-C

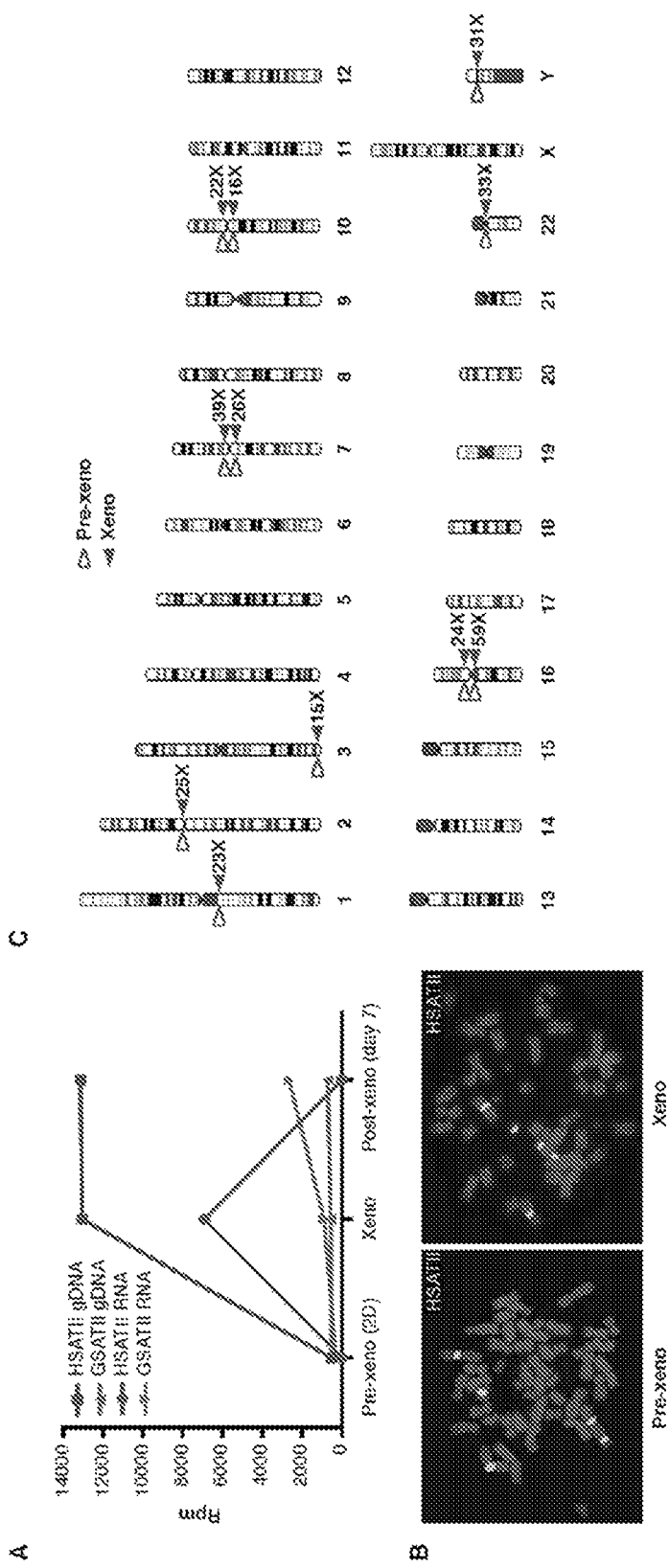
FIGURES 4A-C

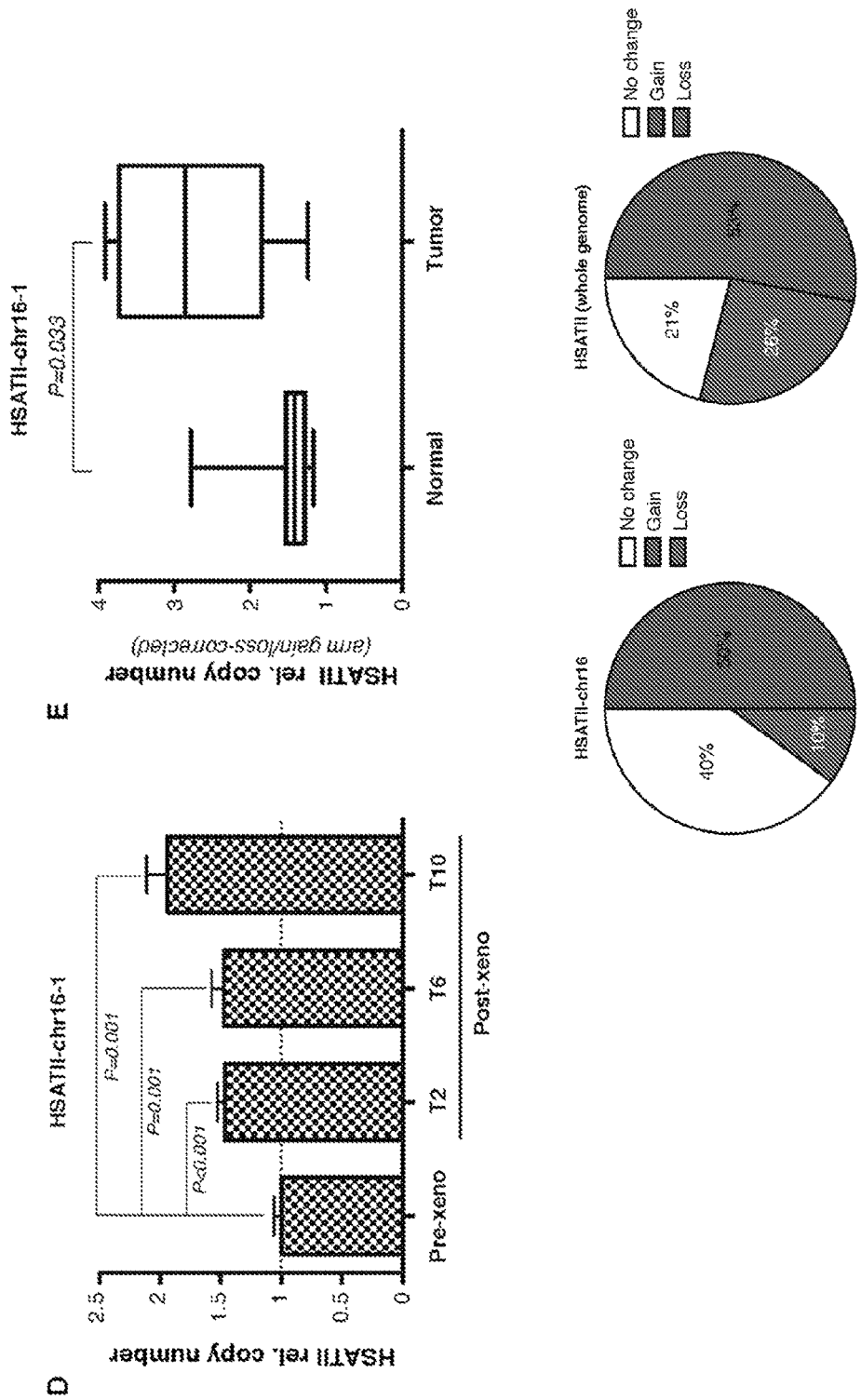
FIGURES 4D-E

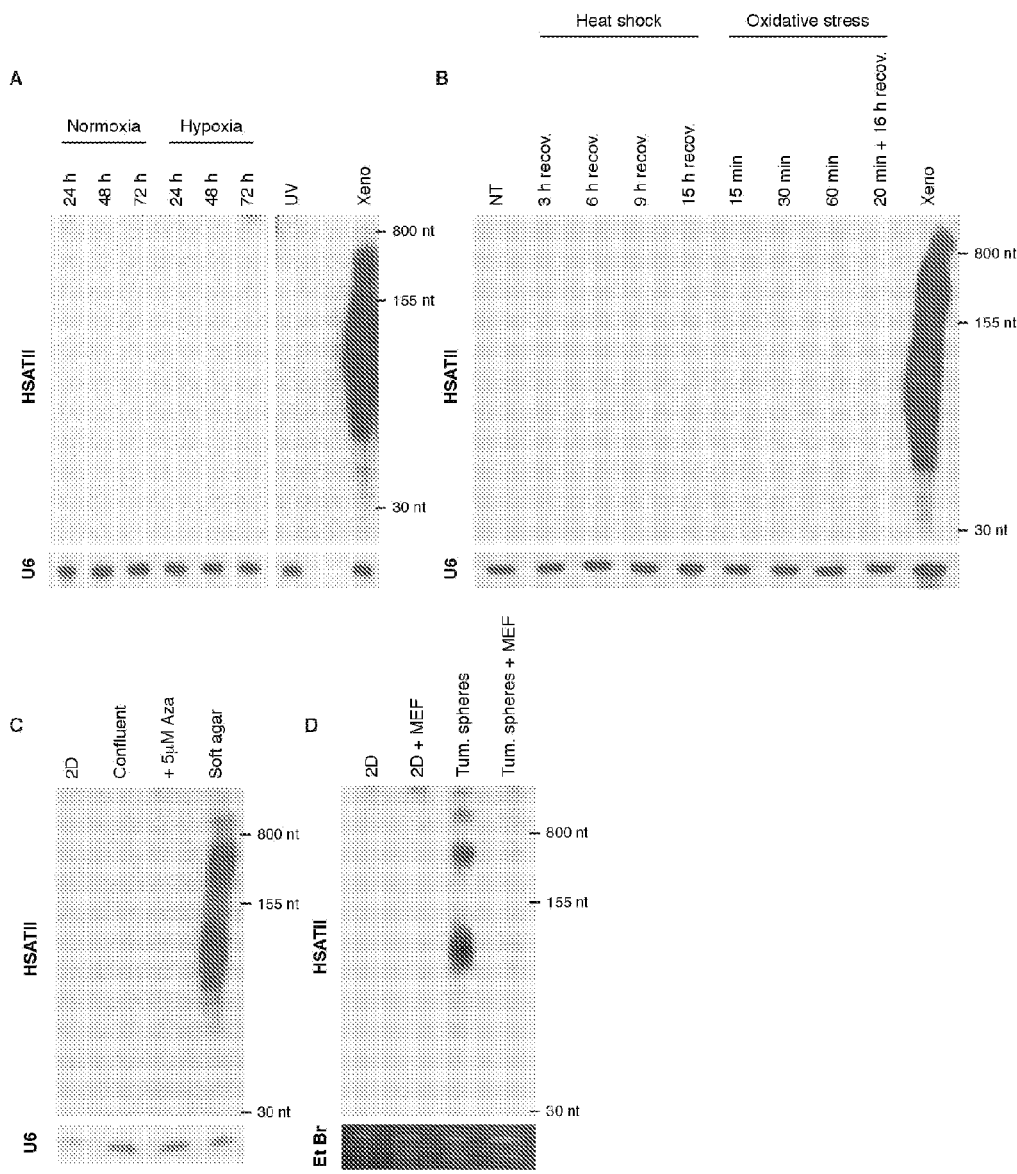
FIGURES 6A-D

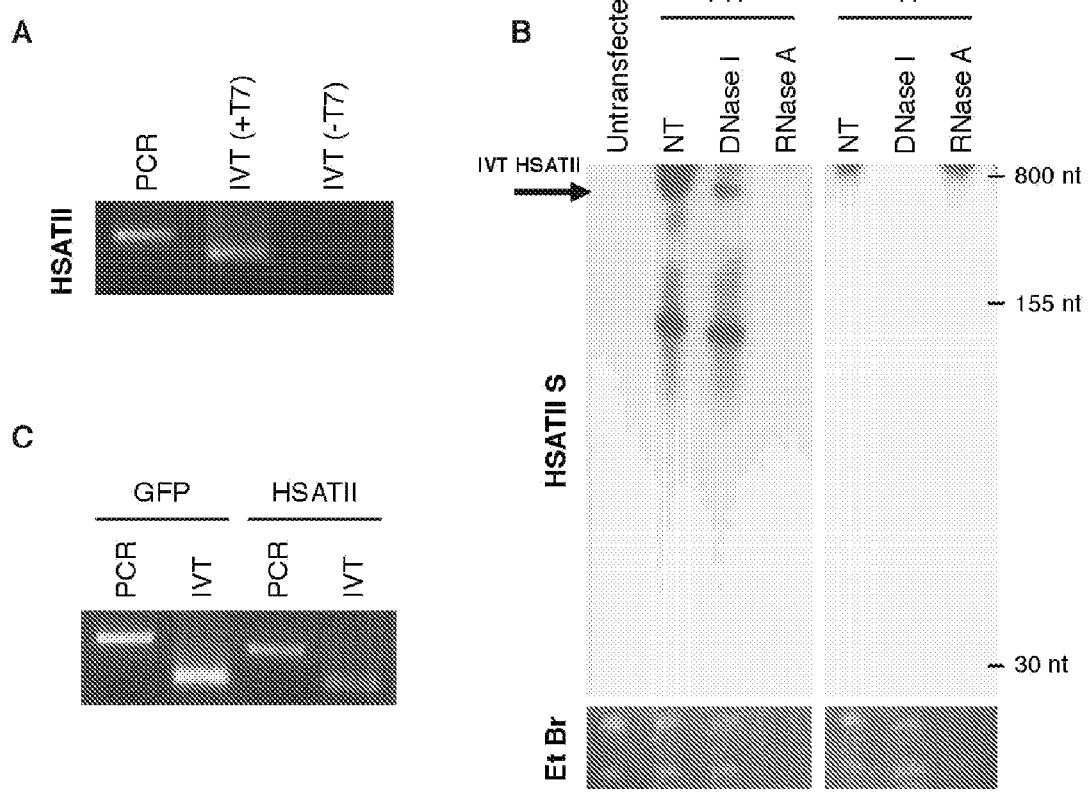
FIGURES 7A-C

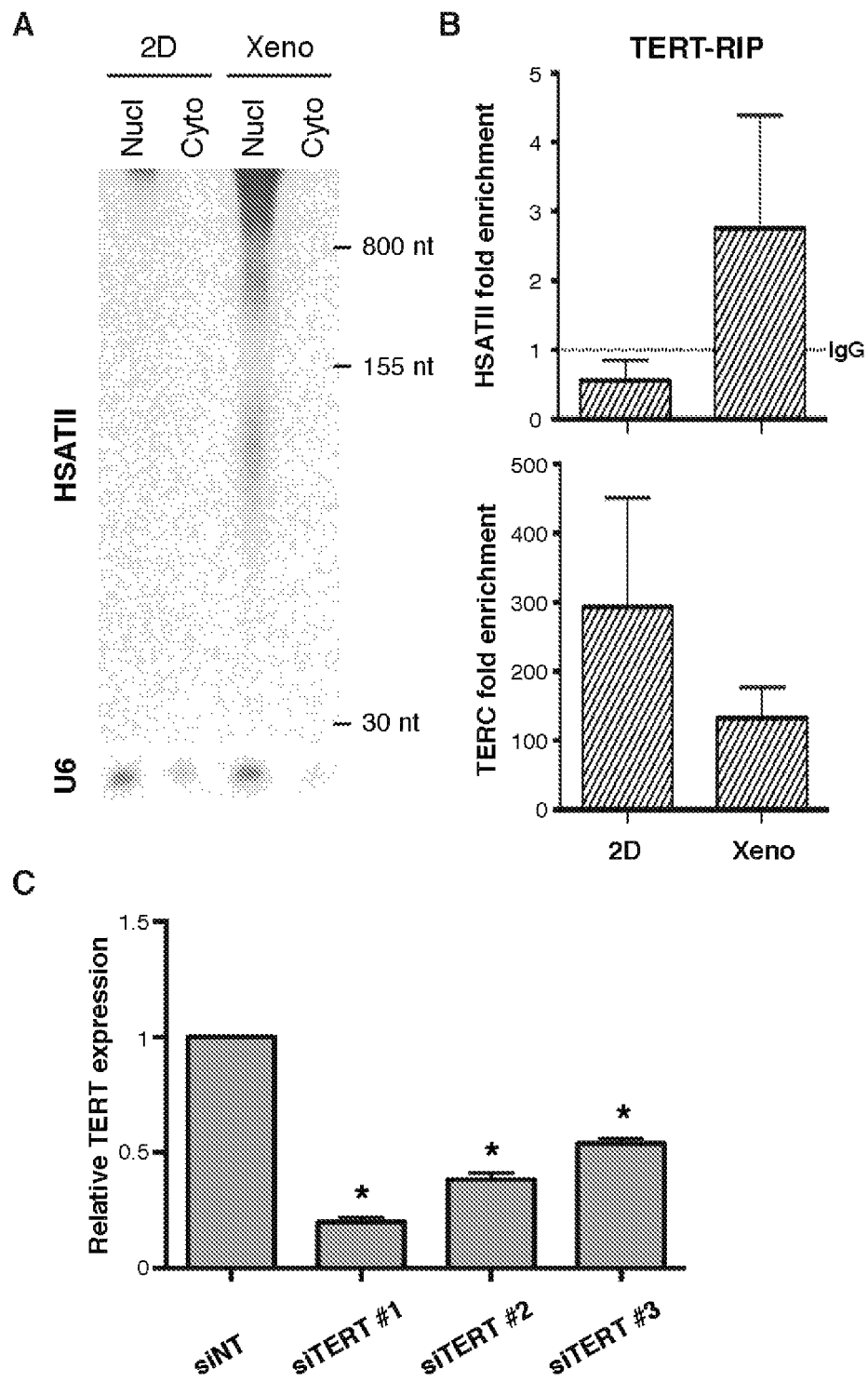
FIGURES 10A-C

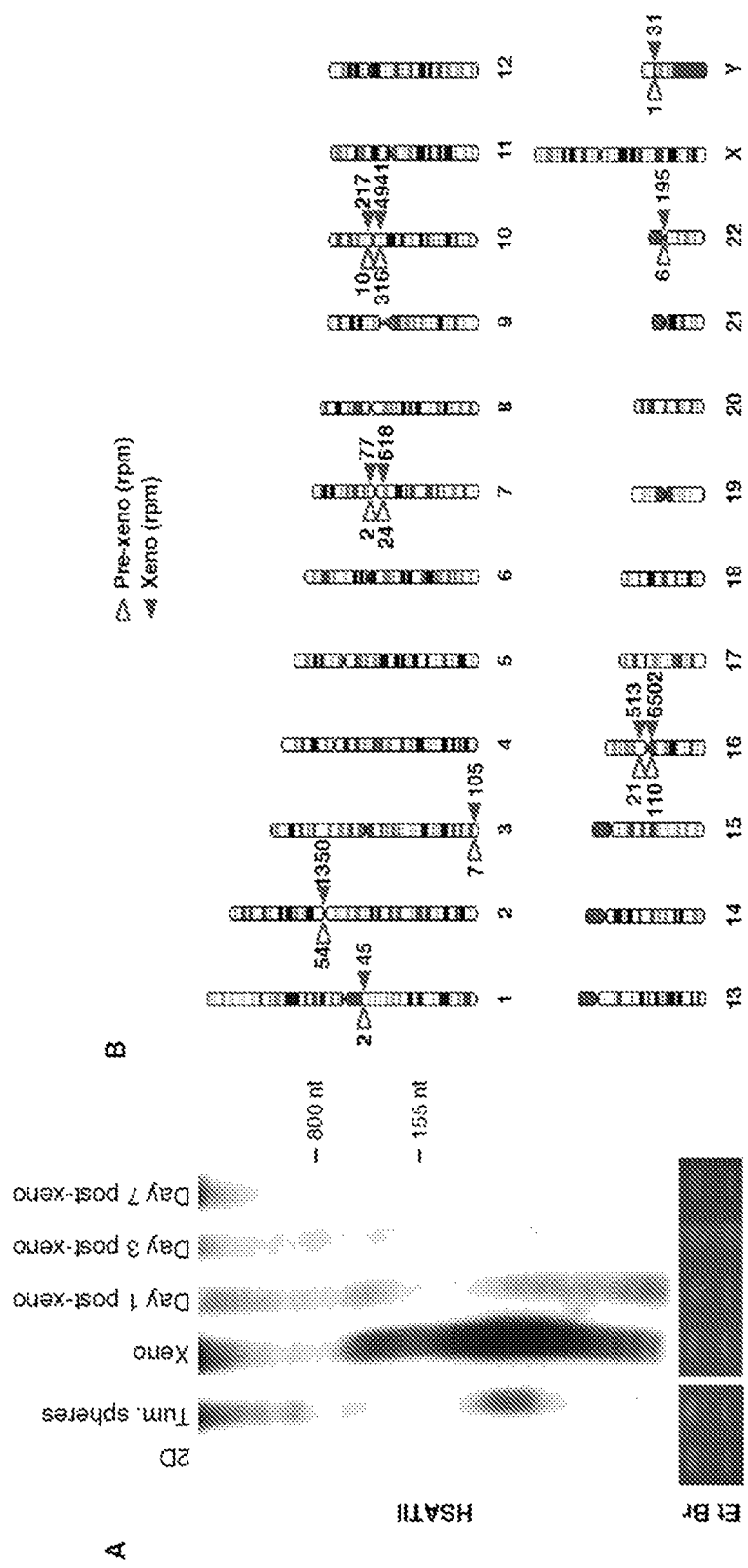
FIGURES 11A-B

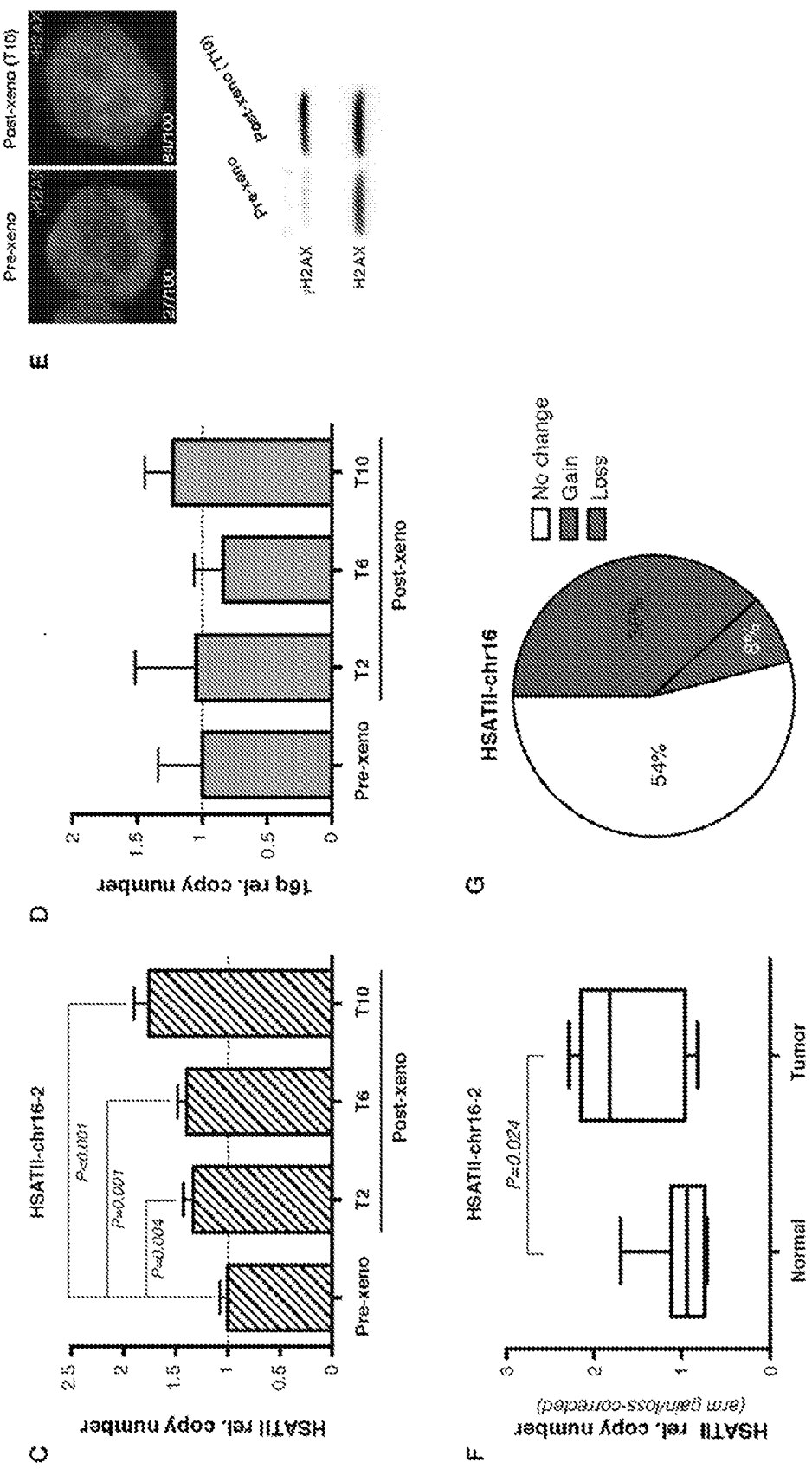
FIGURES 11C-G

| rtype | HSATII | ALR/ALPHA | (CATTC)N | TAR1 | GSATII | BSR/BETA |
|---|---|---|---|---|---|---|
| crcA5YX | 1.248 | 1.05 | 1.283 | -0.127 | | |
| crc3582 | 0.864 | 0.681 | -1.532 | 0.534 | 0.329 | -0.103 |
| crcA5YV | 0.66 | 0.453 | 0.421 | -0.133 | | -0.173 |
| crc3514 | 0.629 | 0.983 | 0.752 | | | |
| crcA01X | 0.498 | | -0.143 | | 0.548 | -0.175 |
| crc3666 | 0.484 | 0.424 | 0.67 | -0.143 | -0.299 | -0.451 |
| crc3555 | 0.483 | | 0.455 | | -0.207 | |
| crc2683 | 0.382 | 0.129 | 0.181 | | | |
| crc3516 | 0.377 | 0.385 | 0.303 | | | |
| crc3518 | 0.371 | 0.754 | 0.323 | -0.242 | | -0.164 |
| crcA03F | 0.339 | | 0.308 | 0.385 | 1.256 | |
| crcA5YW | 0.322 | 0.285 | 0.432 | | -0.09 | -0.17 |
| crc3574 | 0.32 | 0.597 | 0.232 | 0.33 | 1.463 | -0.398 |
| crc6814 | 0.229 | -0.215 | 0.274 | -0.123 | -0.247 | |
| crc3901 | 0.223 | 0.125 | 0.148 | | 0.074 | |
| crcA02Y | 0.223 | 0.31 | -1.53 | 0.107 | 1.085 | -0.211 |
| crc2680 | 0.213 | | | | -0.108 | -0.354 |
| crc3913 | 0.171 | | -1.294 | -0.058 | -0.229 | 0.075 |
| crc2691 | 0.165 | 0.117 | | | | 0.149 |
| crc6141 | 0.133 | 0.095 | 0.083 | | 0.156 | |
| crcA56B | 0.108 | 0.258 | -0.447 | -0.126 | -0.117 | -0.295 |
| crcA5Z1 | 0.105 | 0.303 | -1.637 | -0.238 | -0.183 | |
| crc3896 | 0.102 | 0.205 | 0.251 | | | 0.108 |
| crc2681 | | | -0.386 | | | |
| crcA50V | 0.091 | -0.136 | 0.099 | -0.087 | -0.141 | -0.217 |
| crc4007 | | 0.162 | -1.835 | | -0.186 | -0.288 |
| crcA567 | | | -1.548 | -0.124 | -0.332 | -0.445 |
| crc6718 | | | | | -0.093 | -0.113 |
| crc3727 | | | -0.136 | | -0.248 | -0.229 |
| crc3994 | | 0.459 | | 0.104 | | |
| crc3956 | | 0.354 | -0.693 | | | |
| crc3807 | | -0.033 | -0.354 | | -0.223 | -0.288 |
| crcA032 | | | -0.155 | -0.109 | -0.085 | -0.349 |
| crcA02O | | 0.201 | | 0.185 | 1.509 | -0.133 |
| crcA566 | | 0.201 | | | | |
| crc6781 | | | -0.794 | | | |
| crcA5EJ | | | | -0.132 | | |
| crcA01S | | 0.117 | | -0.115 | 0.096 | -0.302 |
| crcA54L | | | | -0.094 | 0.121 | -0.276 |
| crcA01T | | | -0.176 | -0.194 | -0.099 | -0.271 |
| crc6717 | | 0.066 | | | 0.118 | |
| crc6964 | -0.089 | | | | 0.084 | |
| crc3529 | -0.099 | 0.124 | | | | |
| crc4008 | -0.115 | | -1.386 | -0.189 | -0.23 | -0.216 |
| crc4015 | -0.154 | 0.141 | | | -0.242 | -0.136 |
| crc6540 | -0.185 | | 0.695 | | | -0.076 |
| crcA01R | -0.195 | | -0.816 | -0.072 | | -0.318 |
| crc3685 | -0.196 | 0.487 | -0.636 | -0.067 | | -0.1 |
| crc3664 | -0.279 | 0.195 | -2.088 | 0.203 | -0.239 | -0.255 |
| crcA5EK | -0.31 | | -2.138 | | -0.12 | -0.235 |
| crc2689 | -0.544 | | -0.849 | -0.389 | -0.153 | -1.034 |

FIGURE 12

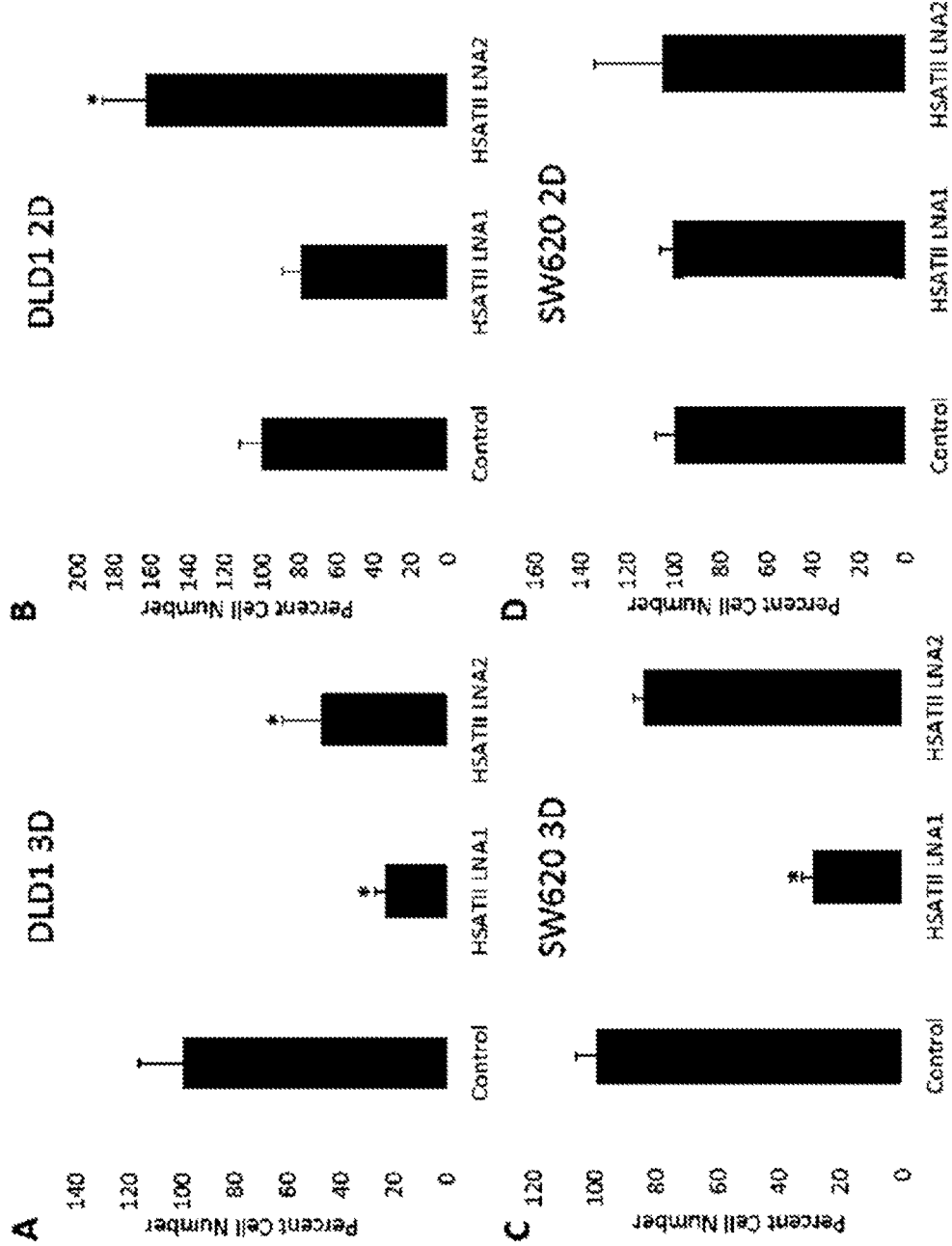
FIGURES 14A-D

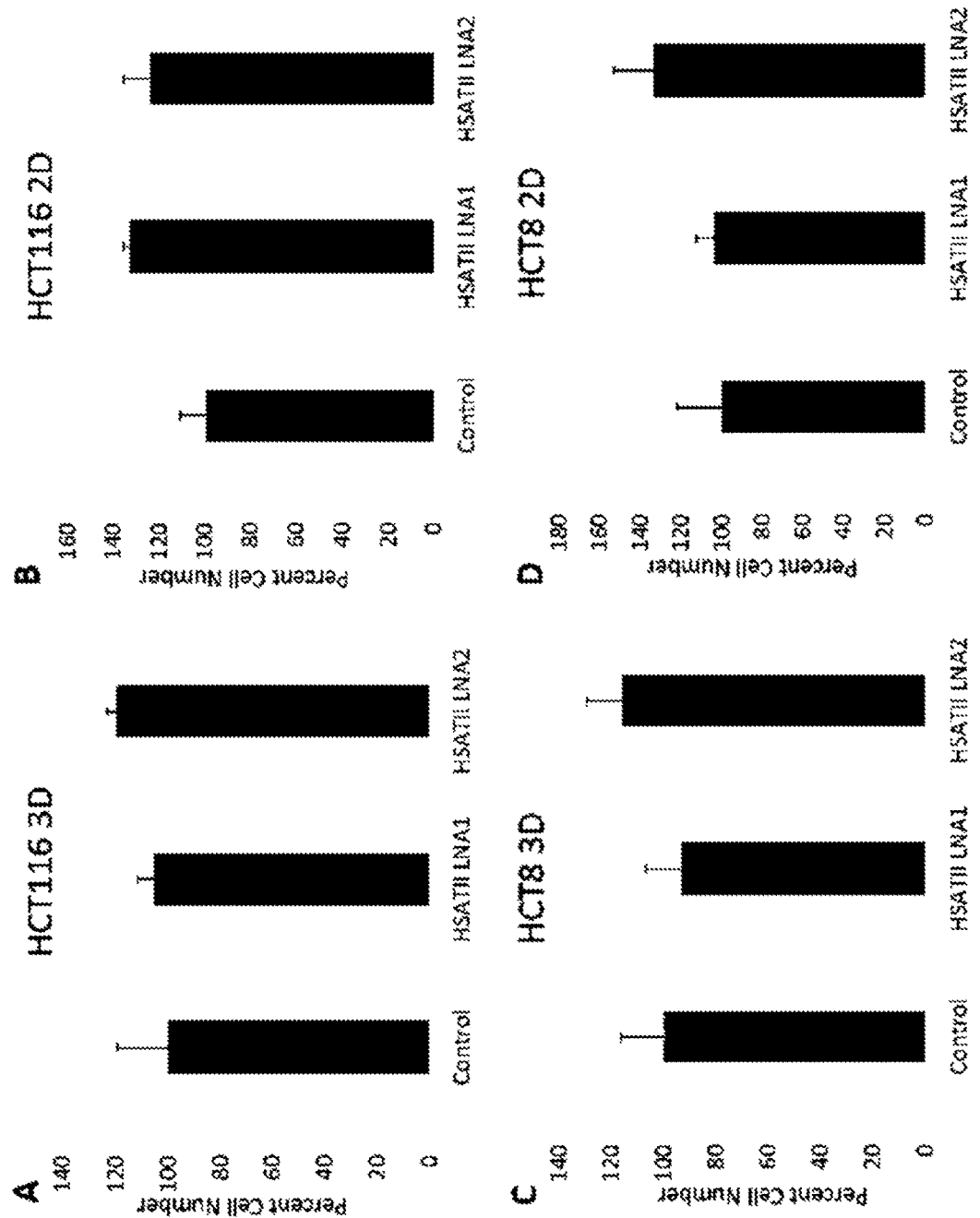
FIGURES 15A-D

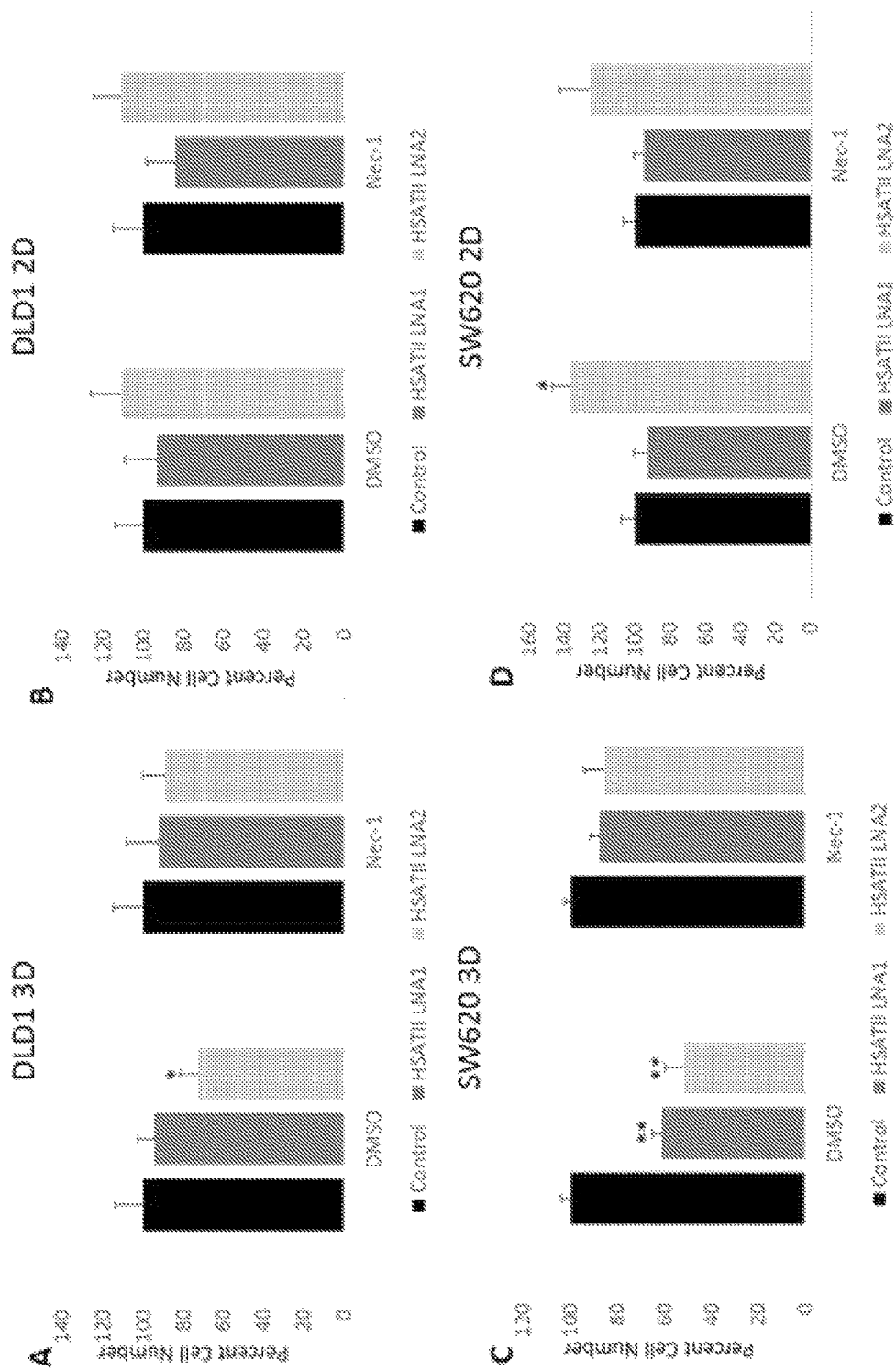
FIGURES 16A-D

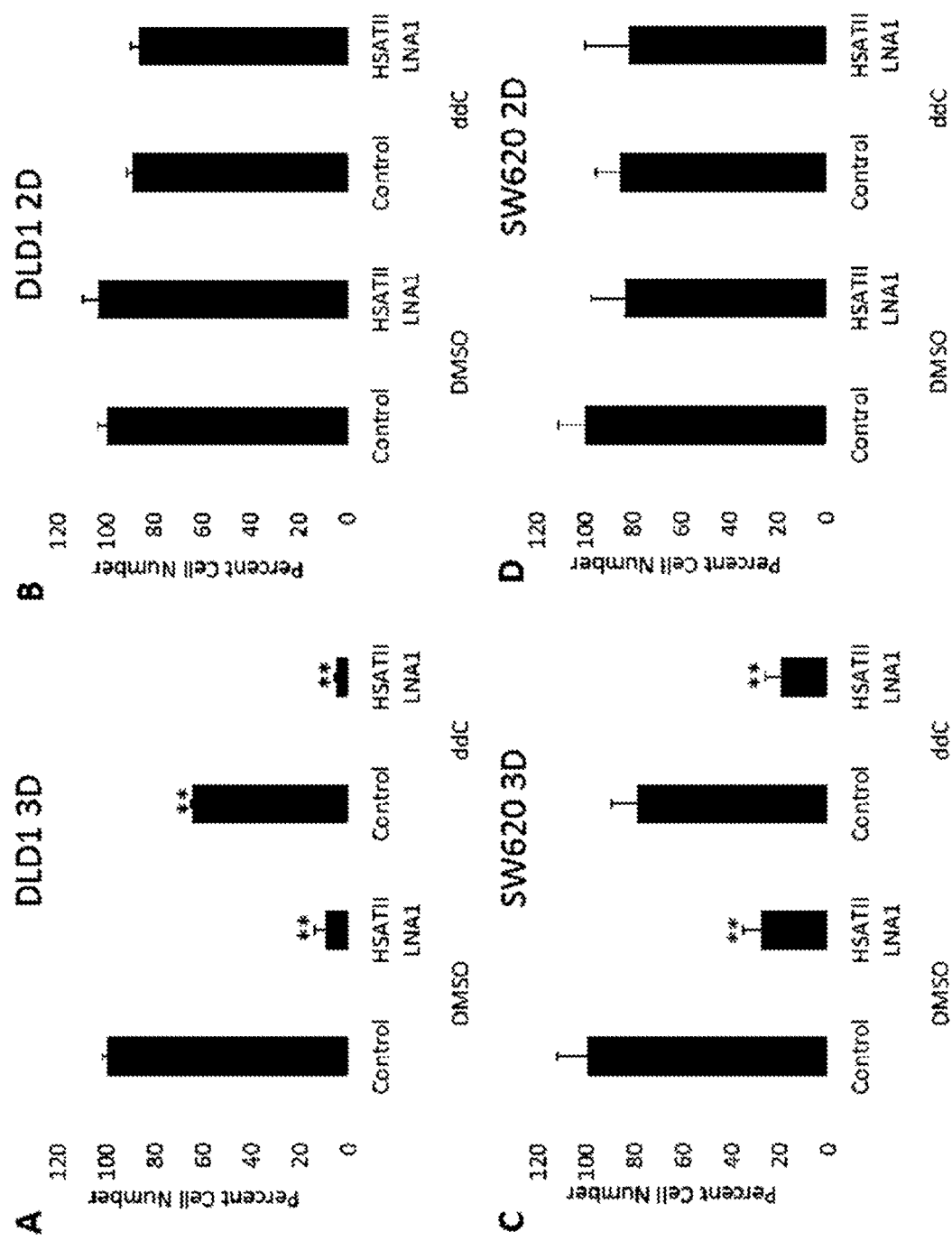
FIGURES 17A-D

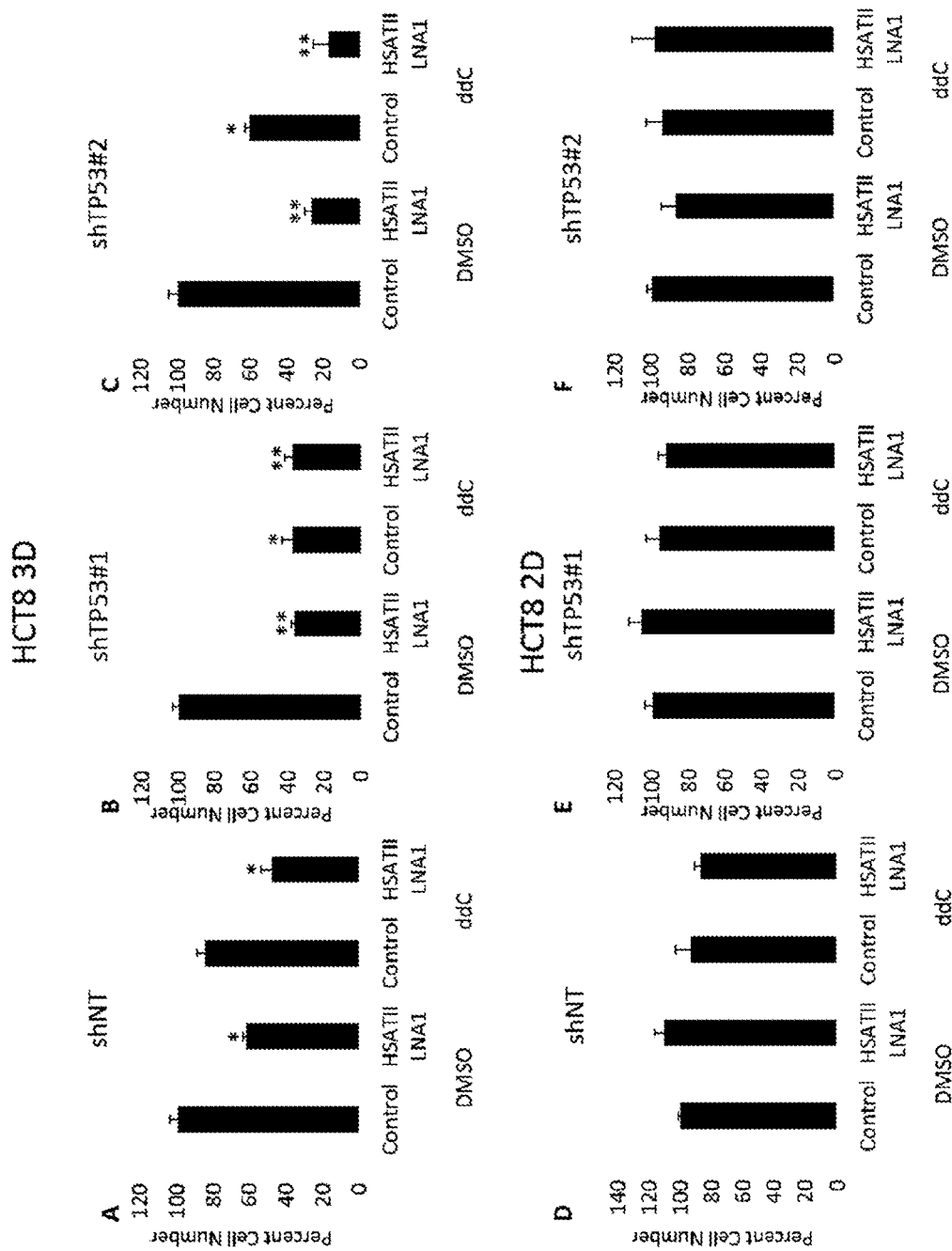
FIGURES 18A-F

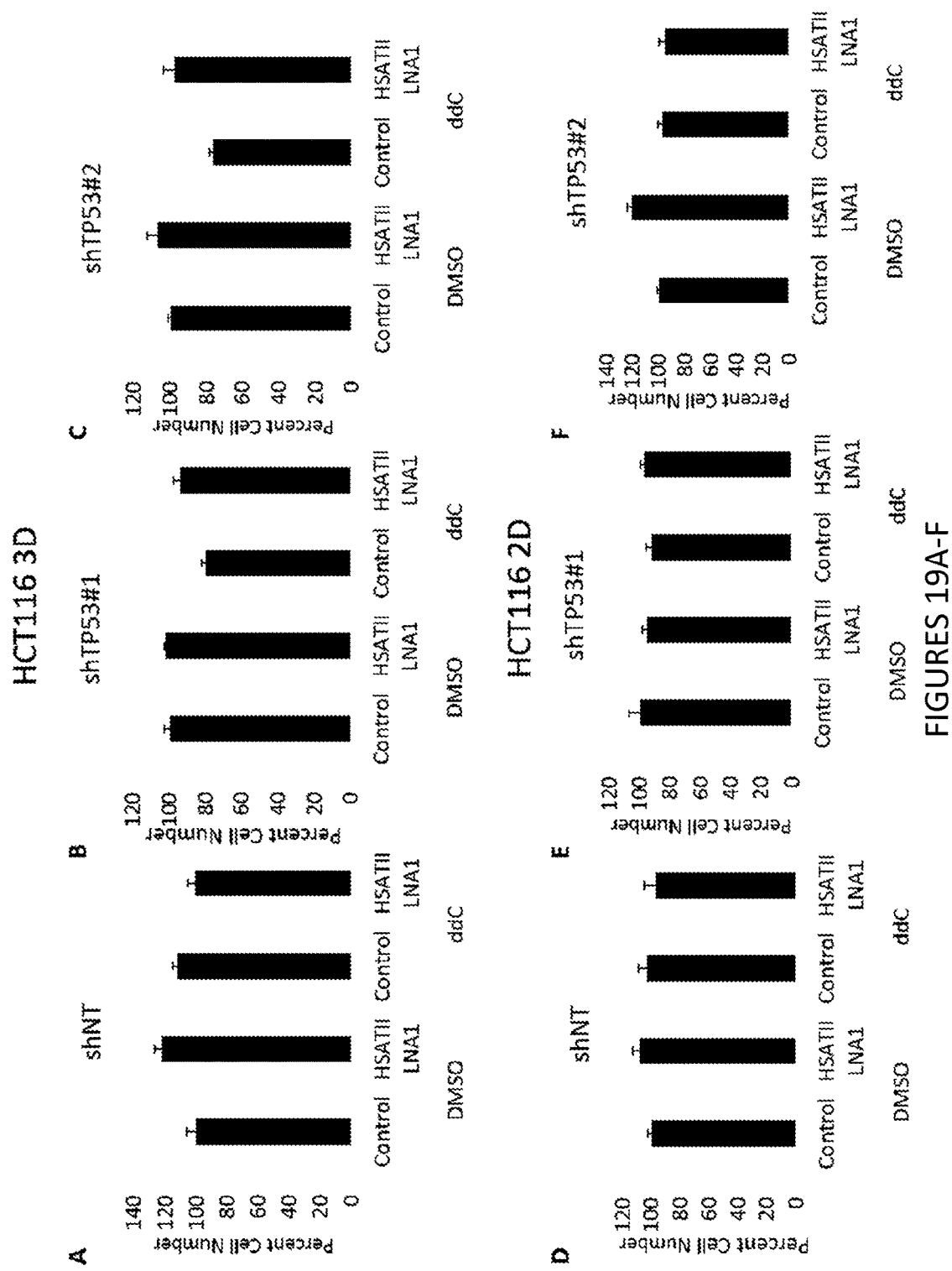
FIGURES 19A-F

TARGETING HUMAN SATELLITE II (HSATII)

CLAIM OF PRIORITY

This application is a § 371 National Stage Application of PCT/US15/37792, filed Jun. 25, 2015, which claims priority under 35 USC § 119(e) to U.S. Patent Application Ser. No. 62/017,012, filed on Jun. 25, 2014. The entire contents of the foregoing are hereby incorporated by reference.

FEDERALLY SPONSORED RESEARCH OR DEVELOPMENT

This invention was made with Government support under Grant Nos. R01CA129933 and K12CA087723-11A1 awarded by the National Institutes of Health, and Grant No. W81XWH-13-1-0237 awarded by the Department of Defense. The Government has certain rights in the invention.

TECHNICAL FIELD

The present invention relates to methods for treating cancer, e.g., cancer of epithelial origin, by specifically targeting human satellite II (HSATII) using sequence specific agents such as oligonucleotides.

BACKGROUND

A high percentage of the human genome is made up of tandemly repeated sequences, wherein multiple copies of a DNA sequence or sequences (the repeat units) are arrayed in head-to-tail pattern. The human satellite II (HSATII) sequence is made up of 23 or 26-nucleotide units that repeat in a 59 bp block. See Prosser et al., J Mol Biol. 187(2):145-55 (1986); Warburton et al., BMC Genomics 9:533 (2008). Overexpression of HSATII transcripts has been shown in pancreatic and other epithelial cancers. See Ting et al., Science. 331(6017):593-6 (2011) and WO2012/048113.

SUMMARY

As shown herein, the heterochromatic HSATII satellite repeat is silenced in normal cells, but massively overexpressed in epithelial cancers and in cancer cell lines when grown as xenografts or in 3D culture. Induction of HSATII RNA, either in xenografts or using in vitro reconstitution models, suggests the appearance of complementary DNA intermediates. This process is suppressed by reverse transcriptase inhibition, and correlated with RNA-immunoprecipitation of the hTERT telomerase subunit. Single molecule next-generation sequencing shows expansion of pericentromeric HSATII loci in mouse tumor xenografts, and HSATII copy number gains are evident in half of primary colon tumors. Together, these observations suggest that the dramatic derepression of HSATII satellites in cancer cells produces RNA-derived DNA intermediates leading to genomic expansion of these loci.

Thus, in one aspect, the present invention provides an isolated oligonucleotide of 7-30 nucleotides that hybridizes to HSATII. In some embodiments, the isolated oligonucleotide hybridizes to at least 7, 8, 9, 10, 11, 12, 13, 14, 15, 16, 17, 18, 19, 20, 21, 22, 23, 24, 25, 26 or more consecutive nucleotides of SEQ ID NO:1.

In some embodiments, the isolated oligonucleotide hybridizes to 7, 8, 9, 10, 11, 12, 13, 14, 15, 16, 17, 18, 19, 20, 21, 22 or 23 consecutive nucleotides of SEQ ID NO:2.

In some embodiments, the isolated oligonucleotide hybridizes to 24, 25, or 26 consecutive nucleotides of SEQ ID NO:3.

In some embodiments, the isolated oligonucleotide hybridizes to 7, 8, 9, 10, 11, 12, 13, 14, 15, 16, 17, 18, 19, 20, 21, 22, 23, 24, 25, 26, 27, 28, 29, 30 or more consecutive nucleotides of SEQ ID NO:4.

In some embodiments, the isolated oligonucleotide hybridizes to 7, 8, 9, 10, 11, 12, 13, 14, 15, 16, 17, 18, 19, 20, or 21 consecutive nucleotides of SEQ ID NO:5.

In some embodiments, the isolated oligonucleotide hybridizes to 7, 8, 9, 10, 11, 12, 13, 14, 15, 16, 17, 18, 19, 20, or 21 consecutive nucleotides of SEQ ID NO:6.

In some embodiments, the isolated oligonucleotide the oligonucleotide does not comprise three or more consecutive guanosine nucleotides.

In some embodiments, the isolated oligonucleotide the oligonucleotide does not comprise four or more consecutive guanosine nucleotides.

In some embodiments, the isolated oligonucleotide the oligonucleotide is 15 to 21 nucleotides in length.

In some embodiments, the isolated oligonucleotide at least one nucleotide of the oligonucleotide is modified and/or is a nucleotide analogue, e.g., is a naturally or non-naturally occurring nucleotide analogue.

In some embodiments, the isolated oligonucleotide at least one nucleotide of the oligonucleotide comprises a 2'O-methyl.

In some embodiments, the isolated oligonucleotide each nucleotide of the oligonucleotide comprises a 2'O-methyl.

In some embodiments, the isolated oligonucleotide the oligonucleotide comprises at least one ribonucleotide, at least one deoxyribonucleotide, or at least one bridged nucleotide. In some embodiments, the isolated oligonucleotide the bridged nucleotide is a LNA nucleotide, a cEt nucleotide or a ENA modified nucleotide. In some embodiments, the isolated oligonucleotide each nucleotide of the oligonucleotide is a LNA nucleotide.

In some embodiments, one or more of the nucleotides of the oligonucleotide comprise 2'-fluoro-deoxyribonucleotides.

In some embodiments, one or more of the nucleotides of the oligonucleotide comprise 2'-O-methyl nucleotides.

In some embodiments, one or more of the nucleotides of the oligonucleotide comprise ENA nucleotide analogues.

In some embodiments, one or more of the nucleotides of the oligonucleotide comprise LNA nucleotides.

In some embodiments, the nucleotides of the oligonucleotide comprise phosphorothioate internucleotide linkages between at least two nucleotides.

In some embodiments, the nucleotides of the oligonucleotide comprise phosphorothioate internucleotide linkages between all nucleotides.

In some embodiments, the isolated oligonucleotide is a gapmer or a mixmer.

In general, the above embodiments are not exclusive and can be present in combination. Exemplary oligonucleotides are presented herein, e.g., SEQ ID NOs. 25 and 26.

In another aspect, the invention provides a pharmaceutical composition comprising an isolated oligonucleotide as described herein, with a pharmaceutically acceptable carrier, e.g., a non-naturally occurring carrier. In some embodiments, the pharmaceitcal composition also includes a reverse transcriptase inhibitor, e.g., a small molecule nucleotide or nucleoside analog reverse transcriptase inhibitor (NRTIs) or Non-nucleoside reverse transcriptase inhibitor (NNRTIs).

In another aspect, the invention provides the isolated oligonucleotides described herein for use as a medicament, e.g., for treating cancer.

In a further aspect, the invention provides methods for treating a subject with cancer, wherein the cancer expresses high levels of HSATII RNA (i.e., levels above a threshold), or has an increased copy number of HSATII, the method comprising administering to the subject a therapeutically effective amount of an oligonucleotide targeting HSATII as described herein. In some embodiments, the methods include detecting the presence of high levels of HSATII RNA, e.g., levels of HSATII RNA above a threshold, or detecting the presence of an increased HSATII copy number, in a sample from the subject, e.g., a biopsy sample comprising tumor cells or tumor tissue from the subject.

In some embodiments, the methods include detecting a level of HSATII RNA or copy number in a sample from the cancer; comparing the level of HSATII RNA or copy number in the sample to a reference level; identifying a subject who has a cancer that has levels of HSATII RNA or copy number above the reference level; and selecting the identified subject for treatment with an oligonucleotide targeting HSATII.

In a further aspect, the invention provides methods for treating a subject with cancer, wherein the cancer has a mutation in TP53. In some embodiments, the methods include detecting a level of TP53 protein in a sample from the cancer; comparing the level of TP53 protein in the sample to a reference level; identifying a subject who has a cancer that has levels of TP53 protein below the reference level; and selecting the identified subject for treatment with an oligonucleotide targeting HSATII.

In some embodiments, the methods include detecting both an increase in HSAT RNA levels or HSATII copy number, and the presence of a TP53 mutation, and selecting a subject who has one or both.

In some embodiments, the methods include comprises detecting a mutation in a TP53 allele in a sample from the cancer; and selecting the subject for treatment with an oligonucleotide targeting HSATII.

In some embodiments, detecting a mutation in a TP53 allele in a sample from the cancer comprises determining a TP53 sequence in the sample and comparing the sequence to a reference sequence; identifying a subject who has a cancer that has a mutation in a TP53 allele; and selecting the identified subject for treatment with an oligonucleotide targeting HSATII.

In some embodiments, detecting a mutation in a TP53 allele in a sample from the cancer comprises; contacting the sample with one or more probes that specifically detect a mutation in TP53; detecting binding of a probe to the sample, thereby detecting the presence of a mutation in TP53 in the cancer; identifying a subject who has a cancer that has a mutation in a TP53 allele; and selecting the identified subject for treatment with an oligonucleotide targeting HSATII.

Also provided herein are the isolated oligonucleotide targeting HSATII as described herein for use in the treatment of a subject with cancer, wherein the cancer expresses levels of HSATII RNA above a reference level, and/or wherein the cancer has a mutation in a TP53 allele.

In some embodiments, instead of or in addition to administering an oligonucleotide targeting HSATII, the methods include administering a reverse transcriptase inhibitor, e.g., a small molecule nucleotide or nucleoside analog reverse transcriptase inhibitor (NRTIs) or Non-nucleoside reverse transcriptase inhibitor (NNRTIs).

In some embodiments, the cancer is an epithelial cancer, e.g., pancreatic, lung, breast, prostate, renal, ovarian, or colorectal cancer.

In an additional aspect, the invention provides isolated oligonucleotides targeting HSATII as described herein for use in the treatment of a subject with cancer, e.g., wherein the cancer expresses high levels of HSATII RNA. In some embodiments, the cancer is an epithelial cancer, e.g., pancreatic, lung, breast, prostate, renal, ovarian, or colorectal cancer.

In another aspect, the invention provides reverse transcriptase inhibitors, e.g., small molecule nucleotide or nucleoside analog reverse transcriptase inhibitors (NRTIs) or Non-nucleoside reverse transcriptase inhibitors (NNRTIs), for use in the treatment of a subject with cancer, e.g., wherein the cancer expresses high levels of HSATII RNA. In some embodiments, the cancer is an epithelial cancer, e.g., pancreatic, lung, breast, prostate, renal, ovarian, or colorectal cancer.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-F. HSATII expression in human tumors and cancer cell models. (A) Experimental layout. (B) Northern blot analysis of HSATII expression in primary samples (see Table 1). Reads per million (rpm) assessed by DGE profiling are indicated below. (C) Linear regression of DGE and Northern blot data of the same samples. (D) Northern blot on HCT116 2D cultures and xenografts probed for HSATII. (E) Northern blot for HSATII on paired 2D and tumor sphere (3D) cultures of colon cancer cell lines. (F) Untreated (NT) or DNAse I-treated extracts from SW620 xenografts hybridized with HSATII probe on a Northern blot. Numbers below indicate relative signal quantitation. Ethidium bromide (Et Br) staining of gels or U6-probed blots are shown for each Northern as a loading control.

TABLE 1

Figure 4F:
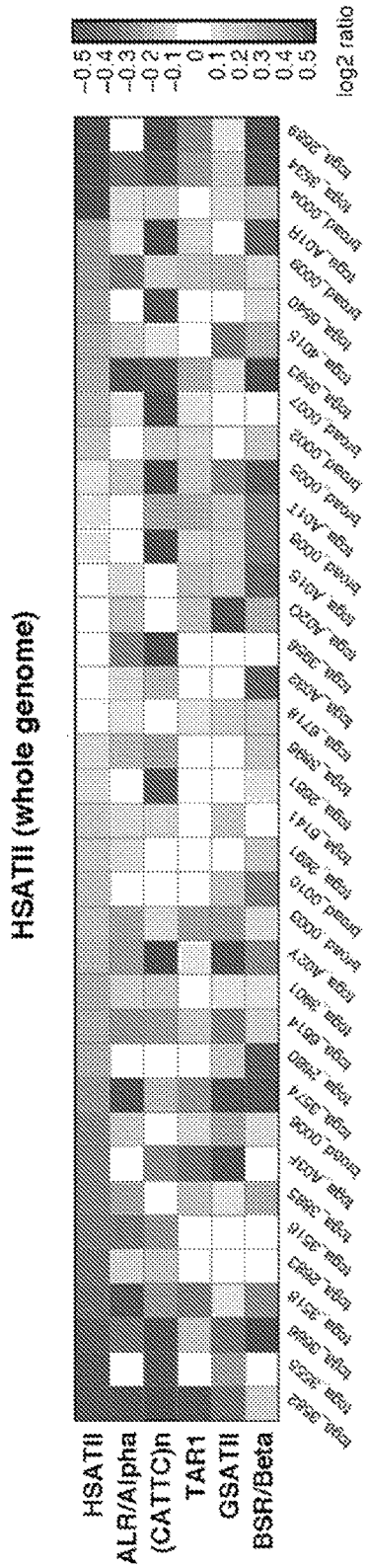

List of primary human samples analyzed by DGE profiling and Northern blot:

| Abbreviation | Sample Type |
|---|---|
| Normal | Normal pancreas |
| PDAC | Pancreatic ductal adenocarcinoma |
| Duodenal ca. | Duodenal carcinoma |
| Well diff NET | Well differentiated neuroendocrine tumor |

FIGS. 2A-E. HSATII RNA gives rise to DNA intermediate species. (A) Experimental layout. (B) Northern blots on extracts from 293T cells transfected with IVT HSATII (corresponding band indicated by the arrow), subjected to the indicated nuclease treatment (NT, untreated) and probed for HSATII S and AS. Ethidium bromide (Et Br) staining of the gel is shown below. (C) Quantification of the relative signal density of the bands in panel (B). (D) and (E) Northern blots on extracts from 293T cells 24 h after transfection with IVT GFP (corresponding band indicated by the arrow) treated with the indicated nucleases. Results of hybridization with GFP S, GFP AS, HSATII S and HSATII AS probes as well as ethidium bromide (Et Br) staining of the gel are shown.

FIGS. 3A-C. HSATII RNA-to-DNA conversion occurs through a reverse transcription mechanism. (A) qPCR analysis on HSATII-chr10 locus following DNAse I or RNase A treatment and reverse transcription of extracts obtained from COLO205 cells treated with DMSO or 2', 3'-dideoxycytidine (ddC). (B) RIP lysates prepared from SW620 2D cultures or xenografts were immunoprecipitated with hTERT or IgG antibody, reverse transcribed and validated by qPCR for HSATII and TERC RNA enrichment. (C) qPCR analysis on HSATII-chr10 locus in COLO205 extracts 72 h after non-targeting (siNT) or TERT-targeting (siTERT) siRNA transfection. For all charts, values represent average of at least three independent experiments ±SEM. *P<0.05 (Student's t test).

FIGS. 4A-G. HSATII rdDNA is re-integrated at the same original locations in the genome leading to pericentromere elongation in xenografts and primary human colon cancers. (A) DGE and copy number analysis of satellite repeats (HSATII, GSATII) in the indicated samples (SW620) quantitated by single molecule sequencing. (B) Representative HSATII DNA FISH on metaphase spreads of pre-xenograft 2D cultures and xenografts obtained from SW620 cells (1000× magnification). (C) Schematic representation of the genomic alignments of DNA-sequencing-derived reads, presented as fold change. (D) qPCR analysis on HSATII-chr16-1 locus. DNA CNV (normalized for beta-Actin) is expressed relative to SW620 cells before xenograft implants (pre-xeno), which was set at 1 (T2, T6, T10=1 week culture post-2nd, -6th and -10th serial transplant respectively). Error bars represent SEM of a triplicate experiment. (E) HSATII-chr16-1 CNV analysis on the indicated paired specimens (left). For each sample, values were normalized for beta-Actin DNA and corrected for chr16q arm changes. P=Student's paired t test. Relative percentage of HSATII copy number changes in colon tumor/normal pairs according to combined HSATII-chr16-1 and -2 CNV analysis (right). (F) Heat map of the WGS data on the indicated primary colon cancer samples (left) and distribution based on a log 2 ratio cut-off=0.1 (right). (G) Proposed model of HSATII overexpression leading to progressive amplification of pericentromeric loci through RT mechanism in 3D cancer cell cultures, xenografts and human tumors.

Figure 5A:
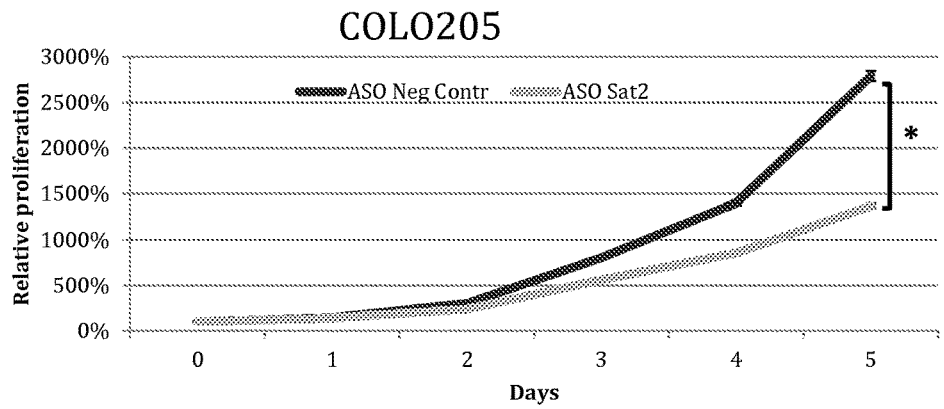
Figure 5B:
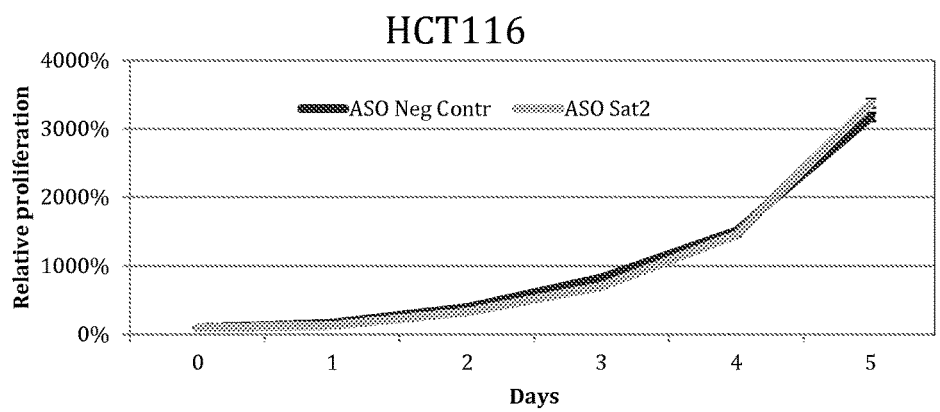
Figure 5C:
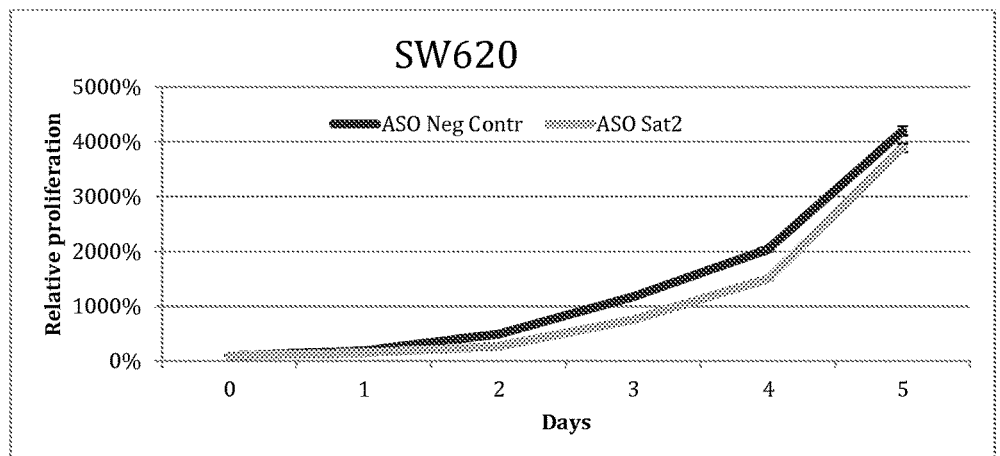

FIGS. 5A-C—LNA-mediated inhibition impairs proliferation in HSATII-expressing cells. Cells were transfected with control (Neg Contr) or HSATII-directed (Sat2) antisense oligonucleotides (ASO). COLO205 (A), HCT116 (B) and SW620 (C) cell proliferation was then evaluated for five days.

FIGS. 6A-D. Assessment of HSATII expression in colon cancer cells. (A) HCT116 cells were grown in low oxygen tension (1%) for the indicated time or UV irradiated for 15 minutes and let recover for 12 hours. RNA was extracted, run on a Northern blot and probed for HSATII and U6. (B) Analogous Northern blot on cells non treated (NT) or subjected to either heat shock (1 hour at 42° C. followed by increasing recovery periods) or oxidative stress (200 μM H2O2 for the indicated times). (C) Same Northern blot on either 2D HCT116 cell cultures or the same cells grown to confluence or in medium containing 5 μM 5-azacytidine for 72 h or in soft agar. (D) Northern blot of HCT116 RNA extracted from the indicated culture conditions and probed for HSATII. For tumor spheres, coculture with irradiated MEF feederlayer cells started 5 days after growth as spheres in absence of adhesion. U6-probed blots or ethidium bromide (Et Br) staining are shown for each Northern as a loading control.

FIGS. 7A-C. Efficiency and specificity of HSATII and GFP IVT. (A) Agarose gel run of HSATII fragment before (PCR) and after in vitro transcription (IVT) with (+T7) or without (−T7) addition of RNA polymerase. (B) Northern blot on 293T cell extracts before (Untransfected) or after transfection with HSATII IVT product and treatment with the indicated nucleases (NT, not treated). Ethidium bromide (Et Br) stainings of the gels are shown below. (C) GFP and HSATII fragments run on an agarose gel prior to (PCR) or after (IVT) in vitro transcription.

Figure 8:
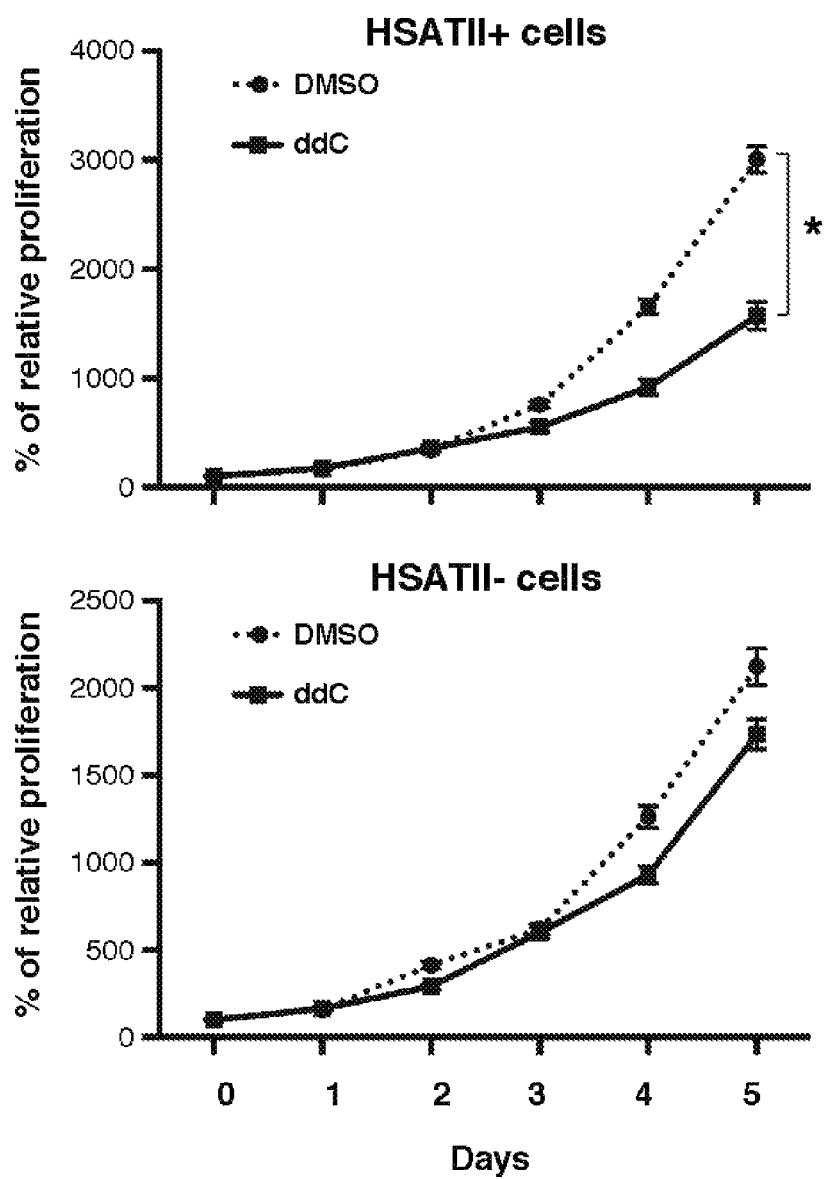

FIG. 8. Proliferation assay of DMSO- or ddC-treated COLO205 (top) and HCT116 (bottom) cells. Cells were seeded at a density of $5 \times 10^2$ cells/well in a 96-well plate and quantified daily using CellTiter-Glo luminescent cell viability assay.

Figure 9:
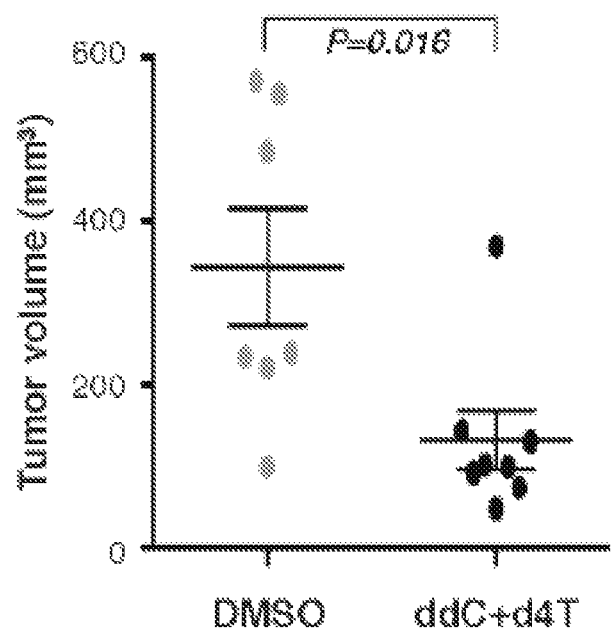

FIG. 9. Nude (Nu/Nu) mice with HCT116 cell line xenografts treated with DMSO or ddC+d4T nucleoside reverse transcriptase inhibitors over 3 weeks shown with tumor volume calculated using diameter and assuming a volumetric sphere. P-value shown using t-test.

FIGS. 10A-C. hTERT contribution to HSATII RT. (A) Northern blot on HSATII following differential nuclear/cytoplasmic RNA extraction from HCT116 2D culture and xenograft. U6 probe was used for relative quantitation. (B) RIP lysates prepared from either 2D cultures or xenografts of HCT116 cells were immunoprecipitated with hTERT or IgG antibody, reverse transcribed and TERC and HSATII RNA enrichment was validated by qPCR. (C) qPCR analysis of TERT expression 72 h after non-targeting (siNT) or TERT-targeting (siTERT) siRNA transfection in COLO205 cells. For all charts, bars represent average of at least three independent experiments ±SEM. *P<0.05 (Student's t test).

FIGS. 11A-G. HSATII expression is only transiently upregulated in xenografts, but its amplification is retained at the DNA level in xenografts and primary human tumors. (A) Northern blot for HSATII on SW620 cells before (2D), during (xeno) and at the indicated times after (post-xeno) in vivo growth. Ethidium bromide (Et Br) staining of the gel is shown below. (B) Schematic representation of the genomic alignments of DNA-sequencing-derived reads, presented as absolute reads per million (rpm), in the two indicated experimental conditions. qPCR analysis on (C) HSATII-chr16-2 locus and (D) chromosome 16q arm. Ct values for all samples were normalized against beta-Actin and DNA CNV is expressed relative to SW620 cells before xenograft implants (pre-xeno), which was set at 1 (T2, T6, T10=1 week culture post-2nd, -6th and -10th serial transplant respectively). Error bars represent SEM of a triplicate experiment. (E) Representative pictures of γH2AX immunofluorescence staining of SW620 cells in the two indicated experimental conditions (upper panel). Insets show counts of cells displaying >3 foci. The same samples where lysed, subjected to western blot and probed for ☐H2AX protein level (lower panel). H2AX was used as a loading control. (F)

HSATII-chr16-2 CNV analysis on the indicated paired specimens. For each sample, values were normalized for beta-Actin DNA and corrected for chr16q arm changes. P=Student's paired t test. (G) Pie chart displaying percentage of HSATII copy number changes in kidney tumor/normal pairs according to combined HSATII-chr16-1 and -2 CNV analysis.

FIG. 12. Satellite DNA enrichment in colorectal cancer samples, adjusted for large copy-number variations (CNV). After correction of these data for large genomic alterations, comparable in size with HSATII stretches, it was found that in fully annotated genomic sequences of 51 colorectal cancers, 23 (45%) had statistically significant genomic gain of HSATII compared with their matched normal germline. Data shown is satellite copy number changes in LOG(2) scale from primary colon cancer from TCGA data. Black is copy number gain>LOG 2(0.2); White is copy number loss<LOG 2(−0.2).

Figure 13:
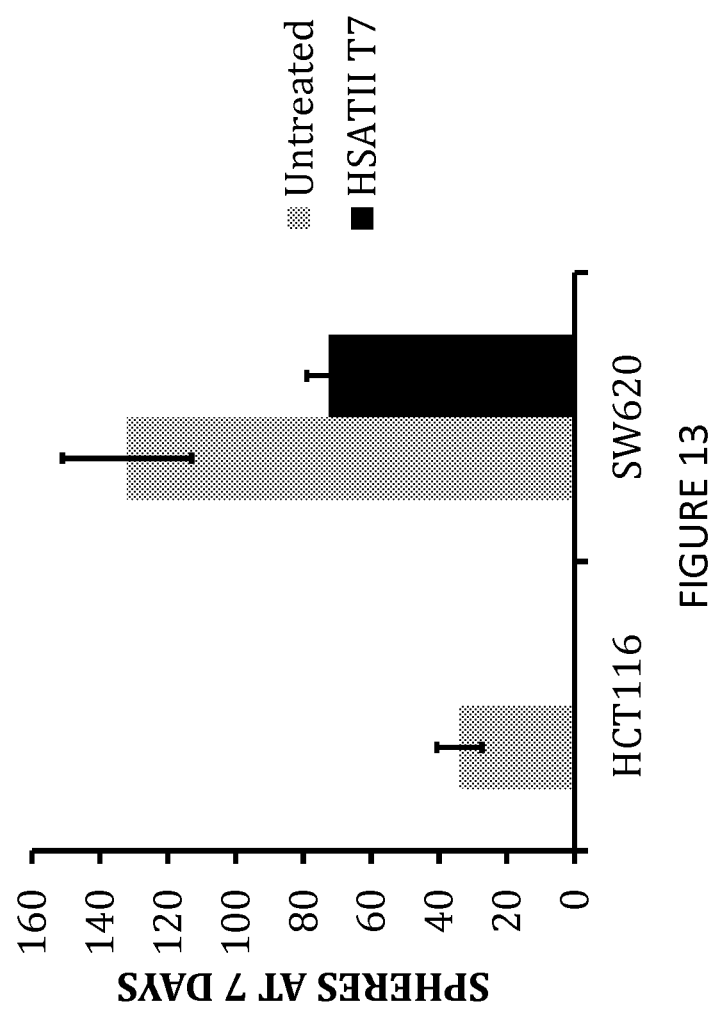

FIG. 13. HSATII in vitro transcribed (IVT) RNA using the T7 RNA polymerase was transfected into colon cancer cell lines HCT116 and SW620 at day −1 followed by tumor sphere culturing at day 0. Total tumor spheres were counted at 7 days after initiation of tumor spheres. Untreated (gray) and HSATII IVT T7 RNA (black).

FIGS. 14A-D. Effect of Locked Nucleic Acids targeting HSATII on TP53 mutant Colorectal Cancer cell lines. DLD1 (A-B), and SW620 (C-D) human colorectal cancer cell lines showed a significant decrease in cell viability in 3 dimensional non-adherent culture (A, C) but not in 2 dimensional adherent conditions in response to treatment with locked nucleic acids targeted to HSATII satellite repeats. Error bars represent standard deviation. P-value was calculated using student's two tailed t-test. *represents $P<0.05$.

FIGS. 15A-D. Effect of Locked Nucleic Acids targeting HSATII on TP53 wild type Colorectal Cancer cell lines. Treatment with Locked Nucleic Acids targeting HSATII satellite repeats does not affect growth of HCT116 (A-B), and HCT8 (C-D) human colorectal cancer cell lines in 3 dimensional (A, C) and 2 dimensional cell culture conditions. Error bars represent standard deviation. P-value was calculated using student's two tailed t-test.

FIGS. 16A-D. HSATII targeted growth inhibition is mediated by the Necroptosis pathway. Treatment of DLD1 (A-B), and SW620 (C-D) TP53 mutant colorectal cancer cell lines with Locked Nucleic Acids targeting HSATII leads to significant growth inhibition in non-adherent (A, C), but not in adherent growth conditions (B, D). This effect can be rescued by treatment with the Necroptosis inhibitor Necrostatin-1 (Nec-1). Error bars represent standard deviation. P-value was calculated using student's two tailed t-test. *represents $P<0.05$, **represents $P<0.01$.

FIGS. 17A-D. Combined HSATII targeting and Reverse Transcriptase inhibition in TP53 mutant human colorectal cancer cell lines. Treatment with Locked Nucleic Acids targeting HSATII leads to significant growth inhibition in DLD-1 (A-B) and SW620 cell lines (C-D) in 3 dimensional (A, C) but not in 2 dimensional (B, D) growth conditions both in the absence, and presence of reverse transcriptase inhibition. Treatment with the reverse transcriptase inhibitor ddC leads to significant growth inhibition in DLD-1 cells (A). HSATII targeting combined with reverse transcriptase inhibition leads to additive growth inhibition in DLD-1 (A), and SW620 (C) cells in 3 dimensional growth conditions. Error bars represent standard deviation. P-value was calculated using student's two tailed t-test. *represents $P<0.05$, **represents $P<0.01$.

FIGS. 18A-F. TP53 knockdown sensitizes HCT8 cells to HSATII targeted Locked Nucleic Acids and Reverse Transcriptase inhibition. HCT8 colorectal cancer cells are resistant to the reverse transcriptase inhibitor ddC under 3D (A) and 2D (D) growth conditions. shRNA mediated knockdown of TP53 sensitizes the cells to reverse transcriptase inhibition under 3D (B-C), but not 2D (E-F) growth conditions. TP53 knockdown sensitizes HCT8 cells to HSATII targeted Locked Nucleic Acids under 3D (B-C), but not 2D (E-F) growth conditions. Error bars represent standard deviation. P-value was calculated using student's two tailed t-test. *represents $P<0.05$, **represents $P<0.01$.

FIGS. 19A-F. HCT116 cells are resistant to HSATII targeting and Reverse Transcriptase inhibition. HCT116 colorectal cancer cells are resistant to the reverse transcriptase inhibitor ddC under 3D (A) and 2D (D) growth conditions. shRNA mediated knockdown of TP53 does not affect sensitivity of HCT116 cells towards HSATII targeted Locked Nucleic Acids, and reverse transcriptase inhibition (B, C, E, F). Error bars represent standard deviation. P-value was calculated using student's two tailed t-test.

DETAILED DESCRIPTION

The stability of pericentromeric heterochromatin structures is essential to ensure chromosomal integrity and faithful duplication of the genome. While pericentromeric satellite repeats are characterized by extreme interspecies sequence diversity, they share a conserved function as core centromere-building elements, thereby stabilizing interactions with DNA-binding proteins, sustaining kinetochore formation, and driving chromosomal segregation during mitosis (1). Heterochromatic repetitive elements were classically considered transcriptionally inactive, but recent studies have shown that fine modulation of transcription in these regions is in fact essential to maintaining heterochromatin architecture and genomic integrity (2). Transcription from pericentromeric satellites has been reported in plants, invertebrates, and during vertebrate development, and some types of satellite repeats are induced following environmental stress in cell line models (3). Massive overexpression of specific classes of satellite repeats in human epithelial cancers resulting from aberrant transcription of these pericentromeric domains has been described (4). In almost all cancers analyzed, subsets of pericentromeric satellites are expressed at very high levels (4-6), whereas others show consistently reduced expression compared with normal tissues. The HSATII satellite is the most differentially expressed human satellite repeat in epithelial cancers (4).

Figure 4G:
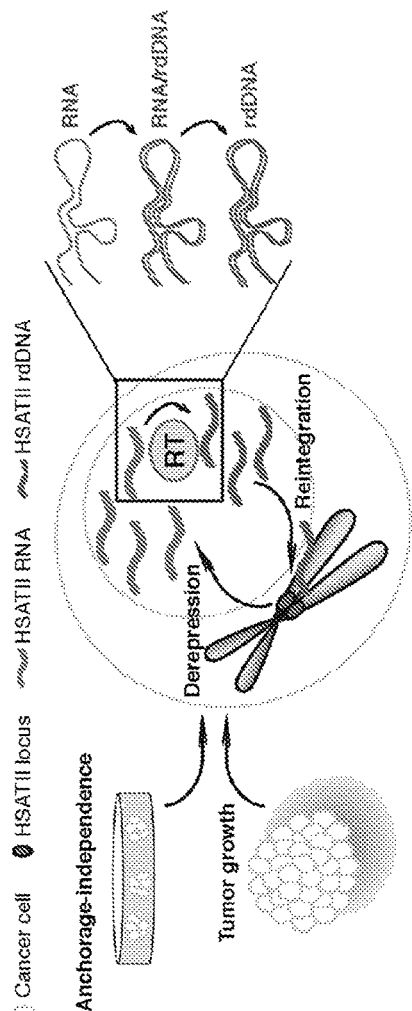

As shows herein, the normally silenced HSATII class of pericentromeric satellites is highly overexpressed in colon cancer cells cultured under non-adherent conditions in vitro or grown as tumor xenografts in vivo, and a population of these RNA transcripts is reverse transcribed into DNA. Reintegration of HSATII RNA-derived-DNA (rdDNA) at the pericentromeric regions from which they emanate appears to drive the progressive amplification of these loci in tumor xenograft models as well as in primary human tumors (FIG. 4G). While this phenomenon is unexpected in mammalian cells, there is ample precedent for retro-element-mediated integration of centromeric repeats in other species (15-17) and the mechanisms underlying telomere expansion in mammalian cells may also apply to intrachromosomal domains (26-30).

Pericentromeric heterochromatin is essential for the initiation of the mitotic spindle, whose disruption leads to a significant fraction of chromosomal defects in human cancers (35, 36). Replication stress also causes double-strand DNA breaks at high frequency within satellite repeat-enriched genomic regions (37). In fact, compared to their parental cells of origin, SW620 cells subjected to ten serial passages as tumor xenografts exhibited massive DNA damage as measured by γH2AX nuclear staining (FIG. 10E). HSATII expansion may partially attenuate the effects of this chromosomal instability. While much remains to be learned about the mechanisms and consequences of specific satellite repeat expansion in cancer, the appropriation by cancer cells of chromosomal integrity pathways mediated by pericentromeric satellites and their dependence on reverse transcriptase activity may point to novel therapeutic targets in colorectal and other epithelial cancers.

Methods of Treatment

The methods described herein can include the administration of oligonucleotides ("oligos") that hybridize specifically to HSATII to treat cancer, e.g., solid tumors of epithelial origin, e.g., pancreatic, lung, breast, prostate, renal, ovarian, or colorectal cancer, in a subject.

As used herein, the term "hyperproliferative" refer to cells having the capacity for autonomous growth, i.e., an abnormal state or condition characterized by rapidly proliferating cell growth. Hyperproliferative disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. A "tumor" is an abnormal growth of hyperproliferative cells. "Cancer" refers to pathologic disease states, e.g., characterized by malignant tumor growth.

As demonstrated herein, the presence of cancer, e.g., solid tumors of epithelial origin, e.g., as defined by the ICD-O (International Classification of Diseases—Oncology) code (revision 3), section (8010-8790), e.g., early stage cancer, is associated with the presence of a massive levels of satellite due to increase in transcription and processing of satellite repeats in epithelial cancer cells. Thus the methods can include the interference of satellite repeats in a sample comprising cells known or suspected of being tumor cells, e.g., cells from solid tumors of epithelial origin, e.g., pancreatic, lung, breast, prostate, renal, ovarian or colon/colorectal cancer cells.

Cancers of epithelial origin can include pancreatic cancer (e.g., pancreatic adenocarcinoma), lung cancer (e.g., non-small cell lung carcinoma or small cell lung carcinoma), prostate cancer, breast cancer, renal cancer, ovarian cancer, or colon cancer. In addition, satellites have been shown to be elevated in preneoplastic or early cancer lesions including intraductal papillary mucinous neoplasm (IPMN), pancreatic intraepithelial neoplasia (PanIN), ductal carcinoma in situ (DCIS), Barrett's Esophagus (Sharma, N Engl J Med. 2009, 24; 361(26):2548-56. Erratum in: N Engl J Med. 2010 Apr. 15; 362(15):1450), etc. The methods can be used to potentially treat early preneoplastic cancers as a means to prevent the development of invasive cancer.

As used herein, "high levels of HSATII RNA" means levels above a reference level or threshold, e.g., a reference that represents a statistically determined threshold above which cancer can be diagnosed or treated using a method described herein; suitable reference levels can be determined by methods known in the art. In some embodiments, the methods include detecting the presence of high levels of HSATII RNA, e.g., levels of HSATII RNA above a threshold, in a sample from the subject, e.g., a biopsy sample comprising tumor cells or tumor tissue from the subject. Levels of HSATII RNA can be determined by any method known in the art, including Northern blot, RNA in situ hybridization (RNA-ISH), RNA expression assays, e.g., microarray analysis, RT-PCR, deep sequencing, cloning, Northern blot, and quantitative real time polymerase chain reaction (qRT-PCR). See WO2012/048113, which is incorporated by reference herein in its entirety. In some embodiments, in place of detecting high levels of HSATII RNA, the methods include detecting copy number of HSATII DNA. An increase in copy number as compared to a normal cell, and/or an increase in levels of HSATII RNA, indicates that the cancer is susceptible to a treatment described herein. Thus the methods can include detecting and/or identifying a cancer that has high levels of HSATII RNA and/or an increased HSATII copy number, and/or selecting a subject who has a cancer with high levels of HSATII RNA and/or an increased HSATII copy number, for treatment with a method described herein.

In some embodiments, the methods include determining TP53 status of the cancer, and selecting a cancer that harbors a mutation in a TP53 allele (or not selecting a cancer that has wild type TP53). Reference genomic sequences for TP53 can be found at NG_017013.2 (Range 5001-24149, RefSeqGene); NC_000017.11 (Range 7668402-7687550, Reference GRCh38.p2 Primary Assembly). The methods can include obtaining a sample containing cells from a subject, and evaluating the presence of a mutation in TP53 as known in the art or described herein in the sample, e.g., by comparing the sequence of TP5S in the sample to a reference sequence, e.g., a reference that represents a sequence in a normal (wild-type) or non-cancerous cell, or a disease reference that represents a sequence in a cell from a cancer, e.g., a malignant cell. A mutation in TP53 associated with susceptibility to treatment using a method described herein is a sequence that is different from the reference sequence (e.g., as provided herein) at one or more positions. In some embodiments, the mutation is a mutation known in the art to be associated with cancer. The International Agency for Research on Cancer maintains a database of TP53 mutations found in human cancers, available online at p53.iarc.fr; see also Petitjean et al., Hum Mutat. 2007 June; 28(6):622-9 (version R17, November 2013). In some embodiments, the mutation is a mutation at codon 175, 245, 248, 249, 273, or 282. See, e.g., Olivier et al. Cold Spring Harb Perspect Biol. 2010 January; 2(1): a001008.

The presence of a mutation in a TP53, and/or HSATII RNA levels and/or HSATII copy number, can be evaluated using methods known in the art, e.g., using polymerase chain reaction (PCR), reverse transcriptase polymerase chain reaction (RT-PCR), quantitative or semi-quantitative real-time RT-PCR, digital PCR i.e. BEAMing ((Beads, Emulsion, Amplification, Magnetics), Diehl (2006) Nat Methods 3:551-559); RNAse protection assay; Northern blot; various types of nucleic acid sequencing (Sanger, pyrosequencing, NextGeneration Sequencing); fluorescent in-situ hybridization (FISH); or gene array/chips); RNA in situ hybridization (RNA-ISH); RNA expression assays, e.g., microarray analysis; multiplexed gene expression analysis methods, e.g., RT-PCR, RNA-sequencing, and oligo hybridization assays including RNA expression microarrays; hybridization based digital barcode quantification assays such as the nCounter® System (NanoString Technologies, Inc., Seattle, Wash.; Kulkarni, Curr Protoc Mol Biol. 2011 April; Chapter 25:Unit25B.10) and lysate based hybridization assays utilizing branched DNA signal amplification such as the QuantiGene 2.0 Single Plex and Multiplex Assays (Affymetrix, Inc., Santa Clara, Calif.; see, e.g., Linton et a., J Mol Diagn. 2012 May-June; 14(3):223-32); SAGE, high-throughput sequencing, multiplex PCR, MLPA, luminex/XMAP, or branched DNA analysis methods. See, e.g., WO2012/048113, which is incorporated herein by reference in it entirety.

In some embodiments, RNA-ISH is used. Certain RNA ISH platforms leverage the ability to amplify the signal within the assay via a branched-chain technique of multiple polynucleotides hybridized to one another (e.g., bDNA) to form a branch structure (e.g., branched nucleic acid signal amplification). In addition to its high sensitivity, the platform also has minimal non-specific background signal compared to immunohistochemistry. While RNA ISH has been used in the research laboratory for many decades, tissue based RNA diagnostics have only recently been introduced in the diagnostic laboratory. However, these have been restricted to highly expressed transcripts such as immunoglobulin light chains as low abundance transcripts such as IgL otherwise cannot be detected by a conventional RNA ISH platform (Hong et al., Surgery 146:250-257, 2009; Magro et al., J Cutan Pathol 30:504-511, 2003). This robust RNA ISH platform with its ability to detect low transcript numbers has the potential to revolutionize RNA diagnostics in paraffin tissue and other tissue assay sample formats.

In some embodiments, the assay is a bDNA assay as described in U.S. Pat. Nos. 7,709,198; 7,803,541; 8,114,681 and 2006/0263769, which describe the general bDNA approach; see especially 14:39 through 15:19 of the '198 patent. In some embodiments, the methods include using a modified RNA in situ hybridization (ISH) technique using a branched-chain DNA assay to directly detect and evaluate the level of biomarker mRNA in the sample (see, e.g., Luo et al., U.S. Pat. No. 7,803,541B2, 2010; Canales et al., Nature Biotechnology 24(9):1115-1122 (2006); Ting et al., Aberrant Overexpression of Satellite Repeats in Pancreatic and Other Epithelial Cancers, Science 331(6017):593-6 (2011)). A kit for performing this assay is commercially-available from Affymetrix, Inc. (e.g., the QuantiGene® ViewRNA Assays for tissue and cell samples).

RNA ISH can be performed, e.g., using the QuantiGene® ViewRNA technology (Affymetrix, Santa Clara, Calif.). QuantiGene® ViewRNA ISH is based on the branched DNA technology wherein signal amplification is achieved via a series of sequential steps (e.g., in a single plex format or a two plex format). Thus in some embodiments, the methods include performing an assay as described in US 2012/0052498 (which describes methods for detecting both a nucleic acid and a protein with bDNA signal amplification, comprising providing a sample comprising or suspected of comprising a target nucleic acid and a target protein; incubating at least two label extender probes each comprising a different L-1 sequence, an antibody specific for the target protein, and at least two label probe systems with the sample comprising or suspected of comprising the target nucleic acid and the target protein, wherein the antibody comprises a pre-amplifier probe, and wherein the at least two label probe systems each comprise a detectably different label; and detecting the detectably different labels in the sample); US 2012/0004132; US 2012/0003648 (which describes methods of amplifying a nucleic acid detection signal comprising hybridizing one or more label extender probes to a target nucleic acid; hybridizing a pre-amplifier to the one or more label extender probes; hybridizing one or more amplifiers to the pre-amplifier; hybridizing one or more label spoke probes to the one or more amplifiers; and hybridizing one or more label probes to the one or more label spoke probes); or US 2012/0172246 (which describes methods of detecting a target nucleic acid sequence, comprising providing a sample comprising or suspected of comprising a target nucleic acid sequence; incubating at least two label extender probes each comprising a different L-1 sequence, and a label probe system with the sample comprising or suspected of comprising the target nucleic acid sequence; and detecting whether the label probe system is associated with the sample). Each hybridized target specific polynucleotide probe acts in turn as a hybridization target for a pre-amplifier polynucleotide that in turn hybridizes with one or more amplifier polynucleotides. In some embodiments two or more target specific probes (label extenders) are hybridized to the target before the appropriate pre-amplifier polynucleotide is bound to the 2 label extenders, but in other embodiments a single label extender can also be used with a pre-amplifier. Thus, in some embodiments the methods include incubating one or more label extender probes with the sample. In some embodiments, the target specific probes (label extenders) are in a ZZ orientation, cruciform orientation, or other (e.g., mixed) orientation; see, e.g., FIGS. 10A and 10B of US 2012/0052498. Each amplifier molecule provides binding sites to multiple detectable label probe oligonucleotides, e.g., chromogen or fluorophore conjugated-polynucleotides, thereby creating a fully assembled signal amplification "tree" that has numerous binding sites for the label probe; the number of binding sites can vary depending on the tree structure and the labeling approach being used, e.g., from 16-64 binding sites up to 3000-4000 range. In some embodiments there are 300-5000 probe binding sites. The number of binding sites can be optimized to be large enough to provide a strong signal but small enough to avoid issues associated with overlarge structures, i.e., small enough to avoid steric effects and to fairly easily enter the fixed/permeabilized cells and be washed out of them if the target is not present, as larger trees will require larger components that may get stuck within pores of the cells (e.g., the pores created during permeabilization, the pores of the nucleus) despite subsequent washing steps and lead to noise generation. A non-limiting bDNA amplification scheme is shown in FIG. 1D.

In some embodiments, the label probe polynucleotides are conjugated to an enzyme capable of interacting with a suitable chromogen, e.g., alkaline phosphatase (AP) or horseradish peroxidase (HRP). Where an alkaline phosphatase (AP)-conjugated polynucleotide probe is used, following sequential addition of an appropriate substrate such as fast red or fast blue substrate, AP breaks down the substrate to form a precipitate that allows in-situ detection of the specific target RNA molecule. Alkaline phosphatase can be used with a number of substrates, e.g., fast red, fast blue, or 5-Bromo-4-chloro-3-indolyl-phosphate (BCIP). Thus in some embodiments, the methods include the use of alkaline phosphatase conjugated polynucleotide probes within a bDNA signal amplification approach, e.g., as described generally in U.S. Pat. Nos. 5,780,277 and 7,033,758. Other enzyme and chromogenic substrate pairs can also be used, e.g., horseradish peroxidase (HRP) and 3,3'-Diaminobenzidine (DAB). Many suitable enzymes and chromogen substrates are known in the art and can be used to provide a variety of colors for the detectable signals generated in the assay, and suitable selection of the enzyme(s) and substrates used can facilitate multiplexing of targets and labels within a single sample. For these embodiments, labeled probes can be detected using known imaging methods, e.g., bright-field microscopy with a CISH approach.

Other embodiments include the use of fluorophore-conjugates probes, e.g., Alexa Fluor dyes (Life Technologies Corporation, Carlsbad, Calif.) conjugated to label probes. In these embodiments, labeled probes can be detected using known imaging methods, e.g., fluorescence microscopy (e.g., FISH). Selection of appropriate fluorophores can also facilitate multiplexing of targets and labels based upon, e.g., the emission spectra of the selected fluorophores.

In some embodiments, the assay is similar to those described in US 2012/0100540; US 2013/0023433; US 2013/0171621; US 2012/0071343; or US 2012/0214152. All of the foregoing are incorporated herein by reference in their entirety.

In some embodiments, an RNA ISH assay is performed without the use of bDNA, and the HSATII or TP53 specific probes are directly or indirectly (e.g., via an antibody) labeled with one or more labels as discussed herein.

The assay can be conducted manually or on an automated instrument, such the Leica BOND family of instruments, or the Ventana DISCOVERY ULTRA or DISCOVERY XT instruments.

As used herein, a "test sample" refers to a biological sample obtained from a subject of interest including a cell or cells, e.g., tissue, from the tumor. (Lehninger Biochemistry (Worth Publishers, Inc., current addition; Sambrook, et al, Molecular Cloning: A Laboratory Manual (3. Sup.rd Edition, 2001); Bernard (2002) Clin Chem 48(8): 1178-1185; Miranda (2010) Kidney International 78:191-199; Bianchi (2011) EMBO Mol Med 3:495-503; Taylor (2013) Front. Genet. 4:142; Yang (2014) PLOS One 9(11):e110641); Nordstrom (2000) Biotechnol. Appl. Biochem. 31(2):107-112; Ahmadian (2000) Anal Biochem 280:103-110. In some embodiments, high throughput methods, e.g., protein or gene chips as are known in the art (see, e.g., Ch. 12, Genomics, in Griffiths et al., Eds. Modern genetic Analysis, 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect the presence and/or level of a mutation in TP53.

In some embodiments a technique suitable for the detection of alterations in the structure or sequence of nucleic acids, such as the presence of deletions, amplifications, or substitutions, can be used for the detection of alterations in HSATII or TP53. In some embodiments, RT-PCR can be used to detect mutations and CNV. The first step in expression profiling by RT-PCR is the reverse transcription of the RNA template into cDNA, followed by its exponential amplification in a PCR reaction (Ausubel et al (1997) Current Protocols of Molecular Biology, John Wiley and Sons). To minimize errors and the effects of sample-to-sample variation, RT-PCR is usually performed using an internal standard, which is expressed at constant level among tissues, and is unaffected by the experimental treatment. Housekeeping genes as known in the art are most commonly used.

In some embodiments, the methods can include detecting protein levels of tp53, and comparing the protein levels to reference protein levels in a normal cell. A mutation in TP53 typically results in a decrease in protein expression levels, so a decrease in protein expression levels as compared to a wild type reference or threshold level can be used as a proxy for mutation status; a cancer in which tp53 levels are decreased can be selected for treatment with a method described herein (or a cancer in which tp53 levels are normal or not substantially decreased as compared to a wild type reference or threshold can be excluded from treatment with a method described herein). The level of a protein can be evaluated using methods known in the art, e.g., using standard electrophoretic and quantitative immunoassay methods for proteins, including but not limited to, Western blot; enzyme linked immunosorbent assay (ELISA); biotin/avidin type assays; protein array detection; radio-immunoassay; immunohistochemistry (IHC); immune-precipitation assay; FACS (fluorescent activated cell sorting); mass spectrometry (Kim (2010) Am J Clin Pathol 134:157-162; Yasun (2012) Anal Chem 84(14):6008-6015; Brody (2010) Expert Rev Mol Diagn 10(8):1013-1022; Philips (2014) PLOS One 9(3): e90226; Pfaffe (2011) Clin Chem 57(5): 675-687). The methods typically include detectable labels such as fluorescent, chemiluminescent, radioactive, and enzymatic or dye molecules that provide a signal either directly or indirectly. As used herein, the term "label" refers to the coupling (i.e. physically linkage) of a detectable substance, such as a radioactive agent or fluorophore (e.g. phycoerythrin (PE) or indocyanine (Cy5), to an antibody or probe, as well as indirect labeling of the probe or antibody (e.g. horseradish peroxidase, HRP) by reactivity with a detectable substance.

In some embodiments, an ELISA method may be used, wherein the wells of a mictrotiter plate are coated with an antibody against which the protein is to be tested. The sample containing or suspected of containing the biological marker is then applied to the wells. After a sufficient amount of time, during which antibody-antigen complexes would have formed, the plate is washed to remove any unbound moieties, and a detectably labelled molecule is added. Again, after a sufficient period of incubation, the plate is washed to remove any excess, unbound molecules, and the presence of the labeled molecule is determined using methods known in the art. Variations of the ELISA method, such as the competitive ELISA or competition assay, and sandwich ELISA, may also be used, as these are well-known to those skilled in the art.

In some embodiments, an IHC method may be used. IHC provides a method of detecting a biological marker in situ. The presence and exact cellular location of the biological marker can be detected. Typically a sample (e.g., a biopsy sample) is fixed with formalin or paraformaldehyde, embedded in paraffin, and cut into sections for staining and subsequent inspection by light microscopy. Current methods of IHC typically use either direct or indirect labelling. The sample may also be inspected by fluorescent microscopy when immunofluorescence (IF) is performed, as a variation to IHC.

Mass spectrometry, and particularly matrix-assisted laser desorption/ionization mass spectrometry (MALDI-MS) and surface-enhanced laser desorption/ionization mass spectrometry (SELDI-MS), is useful for the detection of biomarkers of this invention. (See U.S. Pat. Nos. 5,118,937; 5,045,694; 5,719,060; 6,225,047).

The sample can be, e.g., a biopsy, e.g., needle biopsy or a resection specimen, taken from a mass known or suspected to be a tumor or cancerous.

The reference or predetermined level can be a single cut-off (threshold) value, such as a median or mean, or a level that defines the boundaries of an upper or lower quartile, tertile, or other segment of a cohort, e.g., a clinical trial population, that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

Subjects associated with predetermined values are typically referred to as reference subjects. For example, in some embodiments, a control reference subject does not have does not have cancer.

In some embodiments, the amount by which the level in the subject is greater than the reference level is sufficient to distinguish a subject from a control subject, and optionally is statistically significantly greater than the level in a control subject. In cases where the copy number in a subject is "equal to" the reference copy number, the "being equal" refers to being approximately equal (e.g., not statistically different).

The predetermined value can depend upon the particular population of subjects (e.g., human subjects) selected. Appropriate ranges and categories can be selected with no more than routine experimentation by those of ordinary skill in the art.

In characterizing likelihood, or risk, numerous predetermined values can be established.

Inhibiting HSATII Reverse Transcription with Sequence-Specific Oligonucleotides

As noted above, oligonucleotides ("oligos") that hybridize specifically to HSATII can be used disrupt this reverse transcriptional program and cause reduction in tumor proliferation. An exemplary sequence of HSATII is as follows:

```
HSATII
                                            (SEQ ID NO: 1)
CCATTCGATTCCATTCGATGATTCCATTCGATTCCATTCGATGATGATT

CCATTCGATTCCATTCGATGATTCCATTCGATTCCATTCGATGATGATT

CCATTCGATTCCATTCGATGATTCCATTCGATTCCATTCGATGATGATT

CCATTCGATTCCATTCGATGATT
```

In some embodiments, the oligos hybridize to at least 7, 8, 9, 10, 11, 12, 13, 14, 15, 16, 17, 18, 19, 20, 21, 22, 23, 24, 25, 26, 27, 28, 29, 30 or more consecutive nucleotides of SEQ ID NO1. In some embodiments, the oligos hybridize to at least 7, 8, 9, 10, 11, 12, 13, 14, 15, 16, 17, 18, 19, 20, 21, 22 or 23 consecutive nucleotides of the sequence CCATTCGATTCCATTCGATGATT (SEQ ID NO:2), or to at least 24, 25, or 26 consecutive nucleotides of the sequence CCATTCGATTCCATTCGATGATGATT (SEQ ID NO:3). HSATII includes varying numbers of repeats of the sequence CCATTCGATTCCATTCGATGATTCCATTCGATTCCATTCGATGATGATT (SEQ ID NO:4); the oligos can thus be designed to target 7, 8, 9, 10, 11, 12, 13, 14, 15, 16, 17, 18, 19, 20, 21, 22, 23, 24, 25, 26, 27, 28, 29, 30 or more consecutive nucleotides of SEQ ID NO:4. In some embodiments, the oligos hybridize to at least 7, 8, 9, 10, 11, 12, 13, 14, 15, 16, 17, 18, 19, 20, or 21 consecutive nucleotides of the sequence CATTCGATTCCATTCGATGAT (SEQ ID NO:5) or ATCATCGAATGGAATCGAATG (SEQ ID NO:6).

In some embodiments, the methods include introducing into the cell an oligo that specifically binds, or is complementary, to HSATII. A nucleic acid that "specifically" binds primarily to the target, i.e., to HSATII RNA but not to other non-target RNAs. The specificity of the nucleic acid interaction thus refers to its function (e.g., inhibiting HSATII) rather than its hybridization capacity. Oligos may exhibit nonspecific binding to other sites in the genome or other mRNAs, without interfering with binding of other regulatory proteins and without causing degradation of the non-specifically-bound RNA. Thus this nonspecific binding does not significantly affect function of other non-target RNAs and results in no significant adverse effects. These methods can be used to treat a subject, e.g., a subject with cancer, by administering to the subject a composition (e.g., as described herein) comprising an oligo that binds to a HSATII. Examples of oligos and target sequences are provided herein.

As used herein, treating includes "prophylactic treatment" which means reducing the incidence of or preventing (or reducing risk of) a sign or symptom of a disease in a patient at risk for the disease, and "therapeutic treatment", which means reducing signs or symptoms of a disease, reducing progression of a disease, reducing severity of a disease, in a patient diagnosed with the disease.

In some embodiments, the methods described herein include administering a composition, e.g., a sterile composition, comprising an oligo that is complementary to HSATII sequence as described herein. Oligos for use in practicing the methods described herein can be an antisense or small interfering RNA, including but not limited to an shRNA or siRNA. In some embodiments, the oligo is a modified nucleic acid polymer (e.g., a locked nucleic acid (LNA) molecule), a gapmer, or a mixmer.

Oligos have been employed as therapeutic moieties in the treatment of disease states in animals, including humans. Oligos can be useful therapeutic modalities that can be configured to be useful in treatment regimens for the treatment of cells, tissues and animals, especially humans.

For therapeutics, an animal, preferably a human, suspected of having cancer is treated by administering an oligo in accordance with this disclosure. For example, in one non-limiting embodiment, the methods comprise the step of administering to the animal in need of treatment a therapeutically effective amount of an oligo as described herein.

Oligonucleotides

Oligos useful in the present methods and compositions include antisense oligonucleotides, ribozymes, external guide sequence (EGS) oligonucleotides, siRNA compounds, single- or double-stranded RNA interference (RNAi) compounds such as siRNA compounds, molecules comprising modified bases, locked nucleic acid molecules (LNA molecules), antagomirs, peptide nucleic acid molecules (PNA molecules), mixmers, gapmers, and other oligomeric compounds or oligonucleotide mimetics that hybridize to at least a portion of HSATII and modulate its function. In some embodiments, the oligos include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO2010/040112. However, in some embodiments the oligo is not an miRNA, an stRNA, an shRNA, an siRNA, an RNAi, or a dsRNA.

In some embodiments, the oligos are 10 to 50, 13 to 50, or 13 to 30 nucleotides in length. One having ordinary skill in the art will appreciate that this embodies oligonucleotides having antisense (complementary) portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. It is understood that non-complementary bases may be included in such oligos; for example, an oligo 30 nucleotides in length may have a portion of 15 bases that is complementary to the targeted HSATII RNA. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies oligos having antisense (complementary) portions of 12, 13, 14, 15, 16, 17, 18, 19, 20, 21, 22, 23, 24, 25, 26, 27, 28, 29 or 30 nucleotides in length, or any range therewithin.

Preferably the oligo comprises one or more modifications comprising: a modified sugar moiety, and/or a modified internucleoside linkage, and/or a modified nucleotide and/or combinations thereof. It is not necessary for all positions in a given oligonucleotide to be uniformly modified, and in fact more than one of the modifications described herein may be incorporated in a single oligonucleotide or even at within a single nucleoside within an oligonucleotide.

In some embodiments, the oligos are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric oligos of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5, 220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the oligo comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, ~N($CH_3$)~O~$CH_2$ (known as a methylene(methylimino) or MMI backbone], $CH_2$—O—N ($CH_3$)—$CH_2$, $CH_2$—N ($CH_3$)—N ($CH_3$)—$CH_2$ and O—N ($CH_3$)—$CH_2$—$CH_2$ backbones, wherein the native phosphodiester backbone is represented as O—P—O—CH); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2; see U.S. Pat. Nos. 3,687,808; 4,469,863; 4,476,301; 5,023,243; 5, 177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010; the disclosures of which are incorporated herein by reference in their entireties).

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264, 562; 5,264,564;

5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Modified oligonucleotides are also known that include oligonucleotides that are based on or constructed from arabinonucleotide or modified arabinonucleotide residues. Arabinonucleosides are stereoisomers of ribonucleosides, differing only in the configuration at the 2'-position of the sugar ring. In some embodiments, a 2'-arabino modification is 2'-F arabino. In some embodiments, the modified oligonucleotide is 2'-fluoro-D-arabinonucleic acid (FANA) (as described in, for example, Lon et al., Biochem., 41:3457-3467, 2002 and Min et al., Bioorg. Med. Chem. Lett., 12:2651-2654, 2002; the disclosures of which are incorporated herein by reference in their entireties). Similar modifications can also be made at other positions on the sugar, particularly the 3' position of the sugar on a 3' terminal nucleoside or in 2'-5' linked oligonucleotides and the 5' position of 5' terminal nucleotide.

PCT Publication No. WO 99/67378 discloses arabinonucleic acids (ANA) oligomers and their analogues for improved sequence specific inhibition of gene expression via association to complementary messenger RNA.

Other preferred modifications include ethylene-bridged nucleic acids (ENAs) (e.g., International Patent Publication No. WO 2005/042777, Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties). Preferred ENAs include, but are not limited to, 2'-O,4'-C-ethylene-bridged nucleic acids.

Examples of LNAs are described in WO 2008/043753 and WO2007031091 and include compounds of the following formula.

Scheme 1

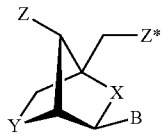

where X and Y are independently selected among the groups —O—, —S—, —N(H)—, N(R)—, —CH$_2$— or —CH— (if part of a double bond), —CH$_2$—O—, —CH$_2$—S—, —CH$_2$—N(H)—, —CH$_2$—N(R)—, —CH$_2$—CH$_2$— or —CH$_2$—CH— (if part of a double bond), —CH=CH—, where R is selected from hydrogen and C$_{1-4}$-alkyl; Z and Z* are independently selected among an internucleoside linkage, a terminal group or a protecting group; B constitutes a natural or non-natural nucleotide base moiety; and the asymmetric groups may be found in either orientation.

Preferably, the LNA used in the oligomer of the invention comprises at least one LNA unit according any of the formulas Scheme 2

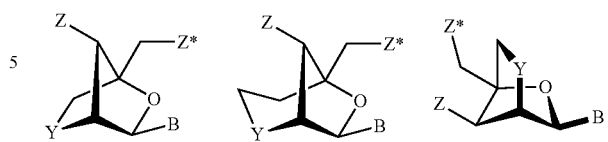

wherein Y is —O—, —S—, —NH—, or N(R$^H$); Z and Z* are independently selected among an internucleoside linkage, a terminal group or a protecting group; B constitutes a natural or non-natural nucleotide base moiety, and RH is selected from hydrogen and C$_{1-4}$-alkyl. Preferably, the Locked Nucleic Acid (LNA) used in an oligomeric compound, such as an antisense oligonucleotide, as described herein comprises at least one nucleotide comprises a Locked Nucleic Acid (LNA) unit according any of the formulas shown in Scheme 2 of PCT/DK2006/000512 (WO2007031091).

Preferably, the LNA used in the oligomer of the invention comprises internucleoside linkages selected from —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—, where R$^H$ is selected from hydrogen and C$_{1-4}$-alkyl.

Specifically preferred LNA units are shown in scheme 3:

Scheme 3

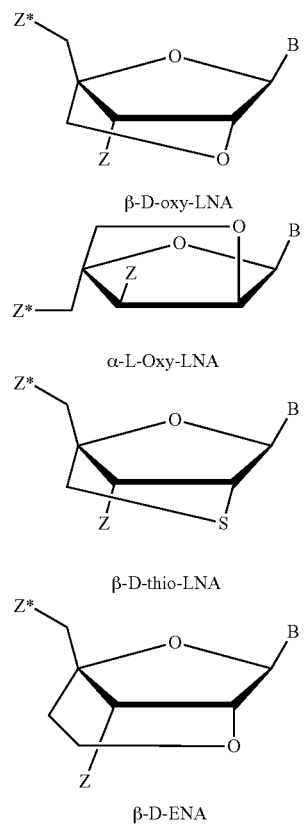

β-D-oxy-LNA

α-L-Oxy-LNA

β-D-thio-LNA

β-D-ENA

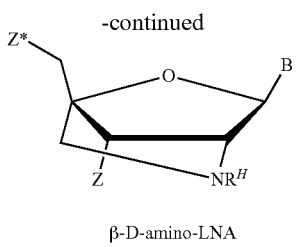

β-D-amino-LNA

The term "thio-LNA" comprises a locked nucleotide in which at least one of X or Y in the general formula above is selected from S or —CH$_2$—S—. Thio-LNA can be in both beta-D and alpha-L-configuration.

The term "amino-LNA" comprises a locked nucleotide in which at least one of X or Y in the general formula above is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleotide in which at least one of X or Y in the general formula above represents —O— or —CH$_2$—O—. Oxy-LNA can be in both beta-D and alpha-L-configuration.

The term "ena-LNA" comprises a locked nucleotide in which Y in the general formula above is —CH$_2$—O— (where the oxygen atom of —CH$_2$—O— is attached to the 2'-position relative to the base B).

LNAs are described in additional detail below. One or more substituted sugar moieties can also be included, e.g., one of the following at the 2' position: OH, SH, SCH$_3$, F, OCN, OCH$_3$ OCH$_3$, OCH$_3$ O(CH$_2$)n CH$_3$, O(CH$_2$)n NH$_2$ or O(CH$_2$)n CH$_3$ where n is from 1 to about 10; Ci to C10 lower alkyl, alkoxyalkoxy, substituted lower alkyl, alkaryl or aralkyl; Cl; Br; CN; CF3; OCF3; O—, S—, or N-alkyl; O—, S—, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-0-CH$_2$CH$_2$OCH$_3$, also known as 2'-O-2-methoxyethyl)] (Martin et al, Helv. Chim. Acta, 1995, 78, 486). Other preferred modifications include 2'-methoxy (2'-0-CH$_3$), 2'-propoxy (2'-OCH$_2$ CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligos can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, isocytosine, pseudoisocytosine, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 5-propynyluracil, 8-azaguanine, 7-deazguanine, N6 (6-aminohexyl)adenine, 6-aminopurine, 2-aminopurine, 2-chloro-6-aminopurine and 2,6-diaminopurine or other diaminopurines. See, e.g., Kornberg, "DNA Replication," W. H. Freeman & Co., San Francisco, 1980, pp 75-77; and Gebeyehu, G., et al. Nucl. Acids Res., 15:4513 (1987)). A "universal" base known in the art, e.g., inosine, can also be included. 5-Me-C substitutions have been shown to increase nucleic acid duplex stability by 0.6-1.2<0>C. (Sanghvi, in Crooke, and Lebleu, eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the modifications described herein may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Oligos can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in "The Concise Encyclopedia of Polymer Science And Engineering", pages 858-859, Kroschwitz, ed. John Wiley & Sons, 1990; those disclosed by Englisch et al., Angewandle Chemie, International Edition, 1991, 30, page 613, and those disclosed by Sanghvi, Chapter 15, Antisense Research and Applications," pages 289-302, Crooke, and Lebleu, eds., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, et al., eds, "Antisense Research and Applications," CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175, 273; 5, 367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

In some embodiments, the oligos are chemically linked to one or more moieties or conjugates that enhance the activity, cellular distribution, or cellular uptake of the oligonucleotide. For example, one or more oligos, of the same or different types, can be conjugated to each other; or oligos can be conjugated to targeting moieties with enhanced specificity for a cell type or tissue type. Such moieties include, but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S—tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5, 245,022; 5,254,469; 5,258,506; 5,262,536; 5,272,250; 5,292,873; 5,317,098; 5,371,241, 5,391, 723; 5,416,203, 5,451,463; 5,510,475; 5,512,667; 5,514,785; 5, 565,552; 5,567,810; 5,574,142; 5,585,481; 5,587,371; 5,595,726; 5,597,696; 5,599,923; 5,599, 928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The oligos useful in the present methods are sufficiently complementary to the target HSATII, e.g., hybridize sufficiently well and with sufficient biological functional specificity, to give the desired effect. "Complementary" refers to the capacity for pairing, through base stacking and specific hydrogen bonding, between two sequences comprising naturally or non-naturally occurring (e.g., modified as described above) bases (nucleosides) or analogs thereof. For example, if a base at one position of an oligo is capable of hydrogen bonding with a base at the corresponding position of HSATII, then the bases are considered to be complementary to each other at that position. 100% complementarity is not required. As noted above, oligos can comprise universal bases, or inert a basic spacers that provide no positive or negative contribution to hydrogen bonding. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and SantaLucia, Nucl. Acids Research, 2005; 33 (19): 6258-6267.

In some embodiments, the location on a target HSATII binding site to which an oligo hybridizes is a region to which a protein binding partner binds. The identification of these binding sites is described in the Examples below. Routine methods can be used to design an oligo that binds to a selected strong or moderate binding site sequence with sufficient specificity. In some embodiments, the methods include using bioinformatics methods known in the art to identify regions of secondary structure, e.g., one, two, or more stem-loop structures, or pseudoknots, and selecting those regions to target with an oligo. For example, methods of designing oligonucleotides similar to the oligos described herein, and various options for modified chemistries or formats, are exemplified in Lennox and Behlke, Gene Therapy (2011) 18: 1111-1120, which is incorporated herein by reference in its entirety, with the understanding that the inhibitory oligonucleotides of the present disclosure do not target miRNA 'seed regions'.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure. One having skill in the art armed with the sequences provided herein will be able, without undue experimentation, to identify further preferred regions to target with complementary oligos.

In the context of the present disclosure, hybridization means base stacking and hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as the term is used in the art, refers to the capacity for precise pairing between two nucleotides. For example, if a nucleotide at a certain position of an oligonucleotide is capable of hydrogen bonding with a nucleotide at the same position of HSATII molecule, then the oligo and the HSATII molecule are considered to be complementary to each other at that position. The oligos and the HSATII molecule are complementary to each other when a sufficient number of corresponding positions in each molecule are occupied by nucleotides that can hydrogen bond with each other through their bases. Thus, "specifically hybridizable" and "complementary" are terms which are used to indicate a sufficient degree of complementarity or precise pairing such that stable and specific binding occurs between the oligo and the HSATII molecule. For example, if a base at one position of an oligo is capable of hydrogen bonding with a base at the corresponding position of HSATII, then the bases are considered to be complementary to each other at that position. 100% complementarity is not required.

It is understood in the art that a complementary nucleic acid sequence need not be 100% complementary to that of its target nucleic acid to be specifically hybridizable. A complementary nucleic acid sequence for purposes of the present methods is specifically hybridizable when binding of the sequence to the target HSATII molecule interferes with the normal function of HSATII to cause a loss of activity and there is a sufficient degree of complementarity to avoid non-specific binding of the sequence to non-target sequences under conditions in which avoidance of the non-specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl, and 75 mM trisodium citrate, preferably less than about 500 mM NaCl, and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 ng/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl, and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

In general, the oligos useful in the methods described herein have at least 80% sequence complementarity to a target region within the target nucleic acid, e.g., 90%, 95%, or 100% sequence complementarity to the target region within HSATII. For example, an antisense compound in which 18 of 20 nucleobases of the antisense oligonucleotide are complementary, and would therefore specifically hybridize, to a target region would represent 90 percent complementarity. Percent complementarity of an oligo with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Antisense and other compounds of the invention that hybridize to HSATII are identified through routine experimentation. In general the oligos must retain specificity for their target, i.e., either do not directly bind to, or do not directly significantly affect expression levels of, transcripts other than the intended target.

Target-specific effects, with corresponding target-specific functional biological effects, are possible even when the oligo exhibits non-specific binding to a large number of non-target RNAs. For example, short 8 base long oligos that are fully complementary to HSATII may have multiple 100% matches to hundreds of sequences in the genome, yet may produce target-specific effects, e.g. upregulation of a specific target gene through inhibition of HSATII activity. 8-base oligos have been reported to prevent exon skipping with with a high degree of specificity and reduced off-target effect. See Singh et al., RNA Biol., 2009; 6(3): 341-350. 8-base oligos have been reported to interfere with miRNA activity without significant off-target effects. See Obad et al., Nature Genetics, 2011; 43: 371-378.

For further disclosure regarding oligos, please see US2010/0317718 (antisense oligos); US2010/0249052 (double-stranded ribonucleic acid (dsRNA)); US2009/0181914 and US2010/0234451 (LNA molecules); US2007/0191294 (siRNA analogues); US2008/0249039 (modified siRNA); and WO2010/129746 and WO2010/040112 (oligos).

Antisense

In some embodiments, the oligos are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to HSATII in vitro, and are expected to inhibit the activity of HSATII in vivo. Thus, oligonucleotides are chosen that are sufficiently complementary to the target, i.e., that hybridize sufficiently well and with sufficient biological functional specificity, to give the desired effect.

Modified Bases, Including Locked Nucleic Acids (LNAs)

In some embodiments, the oligos used in the methods described herein comprise one or more modified bonds or bases. Modified bases include phosphorothioate, methylphosphonate, peptide nucleic acids, or locked nucleic acids (LNAs). Oligos that have been modified (locked nucleic acid—LNA) have demonstrated the "on target" specificity of this approach. Preferably, the modified nucleotides are part of locked nucleic acid molecules, including [alpha]-L-LNAs. LNAs include ribonucleic acid analogues wherein the ribose ring is "locked" by a methylene bridge between the 2'-oxgygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., HSATII sequences as described herien.

The modified base/LNA molecules can include molecules comprising, e.g., 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the HSATII. The modified base/LNA molecules can be chemically synthesized using methods known in the art.

The modified base/LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of a modified base/LNA molecule; for example, a series of oligonucleotides of 10-30 nucleotides spanning the length of a target HSATII can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing modified base/LNA molecules are known in the art; for example, LNA sequences will bind very tightly to other LNA sequences, so it is preferable to avoid significant complementarity within an LNA molecule. Contiguous runs of three or more Gs or Cs, or more than four LNA residues, should be avoided where possible (for example, it may not be possible with very short (e.g., about 9-10 nt) oligonucleotides). In some embodiments, the LNAs are xylo-LNAs.

For additional information regarding LNA molecules see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

As demonstrated herein, LNA molecules can be used as a valuable tool to manipulate and aid analysis of HSATII RNAs. Advantages offered by an LNA molecule-based system are the relatively low costs, easy delivery, and rapid action. While other oligos may exhibit effects after longer periods of time, LNA molecules exhibit effects that are more rapid, e.g., a comparatively early onset of activity, are fully reversible after a recovery period following the synthesis of new HSATII molecules, and occur without causing substantial or substantially complete RNA cleavage or degradation. One or more of these design properties may be desired properties of the oligos of the invention. Additionally, LNA molecules make possible the systematic targeting of domains within much longer nuclear transcripts. The LNA technology enables high-throughput screens for functional analysis of HSATII RNAs and also provides a novel tool to manipulate chromatin states in vivo for therapeutic applications.

In various related aspects, the methods described herein include using LNA molecules to target HSATII for a number of uses, including as a research tool to probe the function of HSATII, e.g., in vitro or in vivo. The methods include selecting one or more desired HSATII sequences, designing one or more LNA molecules that target the HSATII sequences, providing the designed LNA molecule, and administering the LNA molecule to a cell or animal.

In still other related aspects, the LNA molecules targeting HSATII as described herein can be used to create animal or cell models of conditions associated with altered HSATII expression.

Antagomirs

In some embodiments, the oligo is an antagomir. Antagomirs are chemically modified antisense oligonucleotides that can target HSATII. For example, an antagomir for use in the methods described herein can include a nucleotide sequence sufficiently complementary to hybridize to HSATII target sequence of about 12 to 25 nucleotides, preferably about 15 to 23 nucleotides.

In some embodiments, antagomirs include a cholesterol moiety, e.g., at the 3'-end. In some embodiments, antagomirs have various modifications for RNase protection and pharmacologic properties such as enhanced tissue and cellular uptake. For example, in addition to the modifications discussed above for antisense oligos, an antagomir can have one or more of complete or partial 2'-O-methylation of sugar and/or a phosphorothioate backbone. Phosphorothioate modifications provide protection against RNase or other nuclease activity and their lipophilicity contributes to enhanced tissue uptake. In some embodiments, the antagomir cam include six phosphorothioate backbone modifications; two phosphorothioates are located at the 5'-end and four at the 3'-end, but other patterns of phosphorothioate modification are also commonly employed and effective. See, e.g., Krutzfeldt et al., Nature 438,685-689 (2005); Czech, N Engl J Med 2006; 354:1194-1195 (2006); Robertson et al., Silence. 1:10 (2010); Marquez and McCaffrey, Hum Gene Ther. 19(1):27-38 (2008); van Rooij et al., Circ Res. 103(9):919-928 (2008); and Liu et al., Int. J. Mol. Sci. 9:978-999 (2008). Krutzfeld et al. (2005) describe chemically engineered oligonucleotides, termed 'antagomirs', that are reported to be efficient and specific silencers of endogenous miRNAs in mice.

In general, the design of an antagomir avoids target RNA degradation due to the modified sugars present in the molecule. The presence of an unbroken string of unmodified sugars supports RNAseH recruitment and enzymatic activity. Thus, typically the design of an antagomir will include bases that contain modified sugar (e.g., LNA), at the ends or interspersed with natural ribose or deoxyribose nucleobases.

Antagomirs useful in the present methods can also be modified with respect to their length or otherwise the number of nucleotides making up the antagomir. In some embodiments, the antagomirs must retain specificity for their target, i.e., must not directly bind to, or directly significantly affect expression levels of, transcripts other than the intended target. In some embodiments, antagomirs may exhibit nonspecific binding that does not produce significant undesired biologic effect, e.g., the antagomirs do not affect expression levels of non-target transcripts or their association with regulatory proteins or regulatory RNAs.

Interfering RNA, Including siRNA/shRNA

In some embodiments, the oligo sequence that is complementary to HSATII can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc NatlAcadSci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Ribozymes

In some embodiments, the oligos are ribozymes. Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Man, 1995 J. Med. Chem. 38, 2023-2037). Enzymatic nucleic acid molecules can be designed to cleave specific caRNA targets within the background of cellular RNA. Such a cleavage event renders the caRNA non-functional.

In general, enzymatic nucleic acids with RNA cleaving activity act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261:1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $min^{-1}$ in the presence of saturating (10 MM) concentrations of $Mg^{2+}$ cofactor. An artificial "RNA ligase" ribozyme has been shown to catalyze the corresponding self-modification reaction with a rate of about 100 $min^{-1}$. In addition, it is known that certain modified hammerhead ribozymes that have substrate binding arms made of DNA catalyze RNA cleavage with multiple turn-over rates that approach 100 $min^{-1}$.

Making and Using Oligos

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. If desired, nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)).

Preferably, oligos of the invention are synthesized chemically. Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066; WO/2008/043753 and WO/2008/049085, and the refences cited therein.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

In some embodiments, the nucleic acid can include one or more 5-Methyl deoxycytidine nucleosides, and/or one or more 6-Azathymidine, 6-aza-2'-deoxycytidine, 6-methyl-2'-deoxyuridine, 5,6-dimethyl-2'-deoxyuridine, 2'-deoxyuridine, 5-iodo-2'-deoxyuridine, 5-bromo-2'-deoxyuridine, 5-fluoro-2'-deoxyuridine, 5-bromo-2'-deoxycytidine, and/or 5-methyl-2'-deoxycytidine nucleosides.

It is understood that any of the modified chemistries or formats of oligos described herein can be combined with each other, and that one, two, three, four, five, or more different types of modifications can be included within the same molecule.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., Molecular Cloning; A Laboratory Manual 3d ed. (2001); Current Protocols in Molecular Biology, Ausubel et al., eds. (John Wiley & Sons, Inc., New York 2010); Kriegler, Gene Transfer and Expression: A Laboratory Manual (1990); Laboratory Techniques In Biochemistry And Molecular Biology: Hybridization With Nucleic Acid Probes, Part I. Theory and Nucleic Acid Preparation, Tijssen, ed. Elsevier, N.Y. (1993).

Modification Patterns

In some embodiments, the inhibitory oligonucleotide comprises locked nucleic acids (LNA), ENA modified nucleotides, 2'-O-methyl nucleotides, or 2'-fluoro-deoxyribonucleotides. In some embodiments, the inhibitory oligonucleotide comprises alternating deoxyribonucleotides and 2'-fluoro-deoxyribonucleotides. In some embodiments, the inhibitory oligonucleotide comprises alternating deoxyribonucleotides and 2'-O-methyl nucleotides. In some embodiments, the inhibitory oligonucleotide comprises alternating deoxyribonucleotides and ENA modified nucleotides. In some embodiments, the inhibitory oligonucleotide comprises alternating deoxyribonucleotides and locked nucleic acid nucleotides. In some embodiments, the inhibitory oligonucleotide comprises alternating locked nucleic acid nucleotides and 2'-O-methyl nucleotides.

The oligonucleotide may comprise deoxyribonucleotides flanked by at least one bridged nucleotide (e.g., a LNA nucleotide, cEt nucleotide, ENA nucleotide) on each of the 5' and 3' ends of the deoxyribonucleotides. The oligonucleotide may comprise deoxyribonucleotides flanked by 1, 2, 3, 4, 5, 6, 7, 8 or more bridged nucleotides (e.g., LNA nucleotides, cEt nucleotides, ENA nucleotides) on each of the 5' and 3' ends of the deoxyribonucleotides. In some embodiments, the 5' nucleotide of the oligonucleotide is a deoxyribonucleotide. In some embodiments, the 5' nucleotide of the oligonucleotide is a locked nucleic acid nucleotide. In some embodiments, the nucleotides of the oligonucleotide comprise deoxyribonucleotides flanked by at least one locked nucleic acid nucleotide on each of the 5' and 3' ends of the deoxyribonucleotides. In some embodiments, the nucleotide at the 3' position of the oligonucleotide has a 3' hydroxyl group or a 3' thiophosphate.

In some embodiments, the inhibitory oligonucleotide comprises phosphorothioate internucleotide linkages. In some embodiments, the single stranded oligonucleotide comprises phosphorothioate internucleotide linkages between at least two nucleotides. In some embodiments, the single stranded oligonucleotide comprises phosphorothioate internucleotide linkages between all nucleotides.

It should be appreciated that the oligonucleotide can have any combination of modifications as described herein.

As an example, the oligonucleotide may comprise a nucleotide sequence having one or more of the following modification patterns.

(a) (X)Xxxxxx, (X)xXxxxx, (X)xxXxxx, (X)xxxXxx, (X)xxxxXx and (X)xxxxxX, (b) (X)XXxxxx, (X)XxXxxx, (X)XxxXxx, (X)XxxxXx, (X)XxxxxX, (X)xXXxxx, (X)xXxXxx, (X)xXxxXx, (X)xXxxxX, (X)xxXXxx, (X)xxXxXx, (X)xxXxxX, (X)xxxXXx, (X)xxxXxX and (X)xxxxXX, (c) (X)XXXxxx, (X)xXXXxx, (X)xxXXXx, (X)xxxXXX, (X)XXxXxx, (X)XXxxXx, (X)XXxxxX, (X)xXXxXx, (X)xXXxxX, (X)xxXXxX, (X)XxXXxx, (X)XxxXXx, (X)XxxxXX, (X)XxxXxX, (X)xXxXXx, (X)xXxXxX, (X)xxXxXX, (X)xXxXxX and (X)XxXxXx, (d) (X)xxXXXX, (X)xXxXXX, (X)xXXxXX, (X)xXXXxX, (X)x)XXXXXx, (X)Xxx)XXXX, (X)XxXxXX, (X)XxXXxX, (X)XxXXXx, (X)XXxxXX, (X)XXxXxX, (X)XXxXXx, (X)XXXxxX, (X)XXXxXx, (X)XXXXxx, (e) (X)x, (X)XxXXXX, (X)XXxXXX, (X)XXXxXX, (X)XXXXxX and (X)XXXXXx, and (f) XXXXXX, XxXXXXX, XXxXXXX, XXXxXXX, XXXXxXX, XXXXXxX and XXXXXXx, in which "X" denotes a nucleotide analogue, (X) denotes an optional nucleotide analogue, and "x" denotes a DNA or RNA nucleotide unit. Each of the above listed patterns may appear one or more times within an oligonucleotide, alone or in combination with any of the other disclosed modification patterns.

In some embodiments, the oligonucleotide is a gapmer (contain a central stretch (gap) of DNA monomers sufficiently long to induce RNase H cleavage, flanked by blocks of LNA modified nucleotides; see, e.g., Stanton et al., Nucleic Acid Ther. 2012. 22: 344-359; Nowotny et al., Cell, 121:1005-1016, 2005; Kurreck, European Journal of Biochemistry 270: 1628-1644, 2003; FLuiter et al., Mol Biosyst. 5(8):838-43, 2009). In some embodiments, the oligonucleotide is a mixmer (includes alternating short stretches of LNA and DNA; Naguibneva et al., Biomed Pharmacother. 2006 November; 60(9):633-8; Ørom et al., Gene. 2006 May 10; 3720:137-41).

Additional Sequence Structural Information

The inhibitory oligonucleotides described herein may have a sequence that does not contain guanosine nucleotide stretches (e.g., 3 or more, 4 or more, 5 or more, 6 or more consecutive guanosine nucleotides). In some embodiments, oligonucleotides having guanosine nucleotide stretches have increased non-specific binding and/or off-target effects, compared with oligonucleotides that do not have guanosine nucleotide stretches.

The inhibitory oligonucleotides have a sequence that has less than a threshold level of sequence identity with every sequence of nucleotides, of equivalent length, that map to a genomic position encompassing or in proximity to an off-target gene. For example, an oligonucleotide may be designed to ensure that it does not have a sequence that maps to genomic positions encompassing or in proximity with all known genes (e.g., all known protein coding genes) other than the gene of interest. The oligonucleotide is expected to have a reduced likelihood of having off-target effects. The threshold level of sequence identity may be 50%, 60%, 70%, 80%, 85%, 90%, 95%, 99% or 100% sequence identity.

The inhibitory oligonucleotides may have a sequence that is complementary to a region that encodes an RNA that forms a secondary structure comprising at least two single stranded loops. In some embodiments, oligonucleotides that are complementary to a region that encodes an RNA that forms a secondary structure comprising one or more single stranded loops (e.g., at least two single stranded loops) have a greater likelihood of being active (e.g., of being capable of activating or enhancing expression of a target gene) than a randomly selected oligonucleotide. In some cases, the secondary structure may comprise a double stranded stem between the at least two single stranded loops. Accordingly, the area of complementarity between the oligonucleotide and the nucleic acid region may be at a location of the region that encodes at least a portion of at least one of the loops. In some embodiments, the predicted secondary structure RNA (e.g., of the HSATII sequence) containing the nucleic acid region is determined using RNA secondary structure prediction algorithms, e.g., RNAfold, mfold. In some embodiments, oligonucleotides are designed to target a region of the RNA that forms a secondary structure comprising one or more single stranded loop (e.g., at least two single stranded loops) structures which may comprise a double stranded stem between the at least two single stranded loops.

The inhibitory oligonucleotide may have a sequence that is has greater than 30% G-C content, greater than 40% G-C content, greater than 50% G-C content, greater than 60% G-C content, greater than 70% G-C content, or greater than 80% G-C content. The inhibitory oligonucleotide may have a sequence that has up to 100% G-C content, up to 95% G-C content, up to 90% G-C content, or up to 80% G-C content.

In some embodiments, the region of complementarity of the inhibitory oligonucleotide is complementary with at least 8 to 15, 8 to 30, 8 to 40, or 10 to 50, or 5 to 50, or 5 to 40 bases, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides of HSATII as known in the art or disclosed herein. In some embodiments, the region of complementarity is complementary with at least 8, 10, 12, 14, 16, 18, or 20 consecutive nucleotides of HSATII as known in the art or disclosed herein.

Reverse Transcriptase Inhibitors (RTIs)

As an alternative or in addition to oligos targeting HSATII, reverse transcriptase inhibitors, e.g., small molecule nucleotide or nucleoside analog reverse transcriptase inhibitors (NRTIs), can be used, a number of which are known in the art, including Tenofovir, Adefovir, Zidovudine, Didanosine, Zalcitabine, Stavudine, Lamivudine, Abacavir, Emtricitabine, and Entecavir. Non-nucleoside reverse transcriptase inhibitors (NNRTIs) can also be used, e.g., efavirenz, nevirapine, delavidine, etravirine, and rilpivirine.

Pharmaceutical Compositions

The methods described herein can include the administration of pharmaceutical compositions and formulations comprising oligo sequences designed to target HSATII and/or reverse transcriptase inhibitors (RTIs).

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., Remington: The Science and Practice of Pharmacy, 21st ed., 2005.

The oligos can be administered alone or as a component (e.g., active agent) of a pharmaceutical formulation (composition); the RTIs will typically be administered as a component (e.g., active agent) of a pharmaceutical formulation (composition). The compositions may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. In some embodiments, the composition will include both oligos and RTIs as active ingredients.

Formulations of the compositions include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations of this invention can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat.

No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an oligo can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is at risk of or has a disorder described herein, in an amount sufficient to cure, alleviate or partially arrest the clinical manifestations of the disorder or its complications; this can be called a therapeutically effective amount.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; Remington: The Science and Practice of Pharmacy, 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation.

In some embodiments, the methods described herein can include co-administration with other drugs or pharmaceuticals, e.g., compositions for providing cholesterol homeostasis. For example, the oligos can be co-administered with drugs for treating or reducing risk of a disorder described herein.

EXAMPLES

The invention is further described in the following examples, which do not limit the scope of the invention described in the claims.

Materials and Methods

The following materials and methods were used in the Examples 1-7 set forth below.

Cell Lines and Cellular Assays

All colon cancer cell lines were cultured in RPMI-1640+ 10% FBS+1% Pen/Strep (Gibco/Life Technologies). DMEM with the same supplements was used for 293T cells.

For drug treatment, cells were cultured in presence of either DMSO or 100 µM 2', 3'-dideoxycytidine (ddC, Sigma) for two weeks.

For tumor sphere assay, $1\times10^3$ cells were plated as single cell suspension in ultralow attachment 6-well plates (Corning) and grown in serum-free RPMI medium supplemented with 20 µl/ml B27 (Invitrogen/Life Technologies), 20 ng/ml EGF (Invitrogen/Life Technologies) and 20 ng/ml bFGF (Invitrogen/Life Technologies). Fresh medium was added every 3 days. Spheres were collected at day 10.

For soft agar anchorage-independent growth, cells were suspended in 0.4% low-melting agarose (Sigma Aldrich) in 10% RPMI at a density of $2\times10^4$/well, plated on a layer of 0.8% agarose in 10% RPMI in 6-well plates and cultured for 2 weeks.

For proliferation assays, cells were seeded at a density of $5\times10^2$ cells/well in a 96-well plate (Corning) in presence of DMSO/ddC (100 µM) or one day after transfection with control/HSATII antisense oligonucleotides. Daily quantification was performed using CellTiter-Glo luminescent cell viability assay (Promega) with a SpectraMax M5 microplate reader (Molecular Devices).

Xenografts Studies and Human Tissues

For xenograft studies, performed within an animal protocol approved by the MGH Subcommittee on Research Animal Care, $1\times10^6$ cells were injected in the flank of six-week old female nude mice (Charles River Laboratories). Tumors were collected 3 weeks later. Cell cultures were obtained from xenografts upon collagenase IV (Sigma) digestion in 1×HBSS (Gibco/Life Technologies) and filtration through a 70 µm cell strainer. For serial transplantation, collected tumors were minced and a piece of ~2 mm×2 mm was transferred subcutaneously into a recipient mouse.

Human normal and tumor tissues were obtained from the Massachusetts General Hospital within an IRB-approved protocol. Normal human pancreas total RNA was purchased from Clontech.

RNA/DNA Extraction and Nuclease Treatment

Total RNA was extracted with TRIzol (Ambion/Life Technologies) according to standard procedures. Nuclear/cytoplasmic RNA extracts were obtained using Paris Kit (Ambion/Life Technologies) pursuant to the protocol guidelines. DNA was extracted with DNeasy Blood & Tissue Kit (Qiagen) following instructions and including the optional RNase A digestion step.

Nuclease treatments (0.5 U/µl dDNase I, Roche; 10 ng/µl RNase A, Ambion/Life Technologies) were performed on 5 µg of total RNA following the manufacturer's instructions.

Northern Blot

For Northern blot analysis, 5 µg of total RNA, before or after nuclease treatment, were electrophoresed in a 4% or 8% polyacrylamide-urea gel and transferred by electroblotting onto Hybond-N+ membrane (Amersham/GE Healthcare). Hybridization was performed with the following $^{32}$P-labeled DNA oligos: HSATII S, 5'-cattcgattccattcgatgat-3' (SEQ ID NO:7); HSATII AS (also indicated in the text as HSATII), 5'-atcatcgaatggaatcgaatg-3'(SEQ ID NO:8); GFP S, 5'-cgcgcttctcgttggggtctt-3'(SEQ ID NO:9); GFP AS, 5'-aagaccccaacgagaagcgcg-3' (SEQ ID NO:10); U6, 5'-ttgcgtgtcatccttgcgcagg-3'(SEQ ID NO:11). Relative signal density was quantified with Image J software.

In Vitro Transcription and Transfection

HSATII was amplified from the genome with the following primers: FOR, 5'-cattccattccattagatgattcca-3'; REV, 5'-tgaatggaataatccttgaacggaa-3' and inserted into pCRII-TOPO vector (Invitrogen/Life Technologies) via TOPO-TA Cloning (Invitrogen/Life Technologies). GFP was subcloned into the BamHI-SalI sites of pSuper vector (Oligoengine). Both fragments were amplified by PCR with M13 for/rev primers and subjected to in vitro transcription with T7 RNA polymerase following the T7 transcription kit recommendations (Roche). This included a Turbo DNase digestion step after RNA transcription to prevent DNA carryover. 12.5 µg of RNA were then transfected into a 6 cm tissue culture dish containing sub-confluent 293T using Lipofectamine 2000 (Invitrogen/Life Technologies) according to the manufacturer's instructions. Where not indicated, cells were collected 24 h post-transfection for RNA extraction.

RNA-IP (RIP)

At all steps, protease inhibitor cocktail (Roche) and RNaseOUT (Invitrogen/Life Technologies) were added into buffers and solutions. Cells ($1\times10^8$) or minced xenografts were crosslinked for 15 minutes with 1% formaldehyde and the reaction was blocked by addition of 0.125 M glycine. After one wash in PBS, pellets were lysed in 6.5 ml of Buffer A (20 mM Tris-HC1 pH 7.4, 150 mM NaCl, 0.5% NP-40, 0.1 M dithiothreitol) and incubated 30 minutes at 4° C. After centrifuging for 20 minutes at maximum speed at 4° C. and a freeze/thaw cycle, we proceeded with protein determination. Equal amounts of lysate (2 mg per antibody) were first pre-cleared with Protein A Dynabeads (Invitrogen/Life Technology) for 2 hours at 4° C. and then incubated overnight with 3 µg antibody (Rabbit-anti-TERT, Rockland; Normal rabbit IgG, Cell Signaling) at 4° C. 1% input was set aside before addition of antibodies. Fresh Dynabeads (40 µl) were added to the lysate and incubated 2 hours at 4° C. After binding, beads were washed three times for 30 minutes with Buffer A and immunocomplexes were eluted in 250 µl Elution buffer (100 mM NaHCO$_3$, 1% SDS). Samples were then de-crosslinked by addition of 200 mM NaCl and incubation at 65° C. for 2 hours. RNA extraction was performed after addition of 750 ul TRIzol-LS (Ambion/Life Technologies) according to standard procedures and was followed by DNase I digestion and reverse transcription. After qPCR (see details below) RIP fraction Ct values were normalized against input RNA fractions (1%) and fold enrichment was calculated for each sample as the $2^{(-\Delta\Delta Ct)}$ of the normalized TERT-RIP Ct values over the normalized background (IgG-RIP fraction), which was set at 1. Mean values shown in FIG. 3B and S4 B are from biological replicates of 4 2D and 10 xenograft samples.

qPCR

RNA was reverse transcribed using a SuperScript III First-Strand Synthesis kit (Invitrogen/Life Technologies) and cDNA was analyzed by qPCR using either Power SYBR-Green PCR Maser Mix or TaqMan Universal Master Mix on an ABI/PRISM 7500 platform (all reagents were from Applied Biosystems/Life Technologies). The following primers were used: HSATH-chr10 for, 5'-gcattcaattcattagatgacgg-3' (SEQ ID NO:12); HSATH-chr10 rev, 5'-ccttgacccgaatgcaatca-3' (SEQ ID NO:13); TERC for, 5'-tctaaccctaactgagaagggcgt-3'(SEQ ID NO:14); TERC rev, 5'-tgctctagaatgaacggtggaagg-3'(SEQ ID NO:15). In DNase I/RNase A digestion experiments followed by qPCR, HSATII Ct values were normalized against the corresponding untreated samples.

For copy number variation assessment on purified DNA, the following primer pairs were used: HSATII-chr16-1 for, 5'-ccattcgttaatgcctttcg-3' (SEQ ID NO:16); HSATII-chr16-1 rev, 5'-cacgaatggaatcattgtcg-3'(SEQ ID NO:17); HSATII-chr16-2 for, 5'-tccattcgaggattccactc-3'(SEQ ID NO:18); HSATII-chr16-2 rev, 5'-caaagggaagcaaaggaaatc-3'(SEQ ID NO:19); 16q for, 5'-ggggtaaaagggcatgtttt-3'(SEQ ID NO:20); 16q rev, 5'-ctgaagaagcccactcaagg-3'(SEQ ID NO:21); β-Actin for, 5'-ctcttccagccttccttcct-3'(SEQ ID NO:22); β-Actin rev, 5'-agcactgtgttggcgtacag-3'(SEQ ID NO:23).

TaqMan probes were employed for TERT (Hs00972656_m1) and β-Actin (Hs01060665_g1) analysis on COLO205 cells.

siRNA and LNA Transfection 50 nM ON-TARGETplus Non-targeting pool siRNA (Thermo Scientific) and Mission Pre-designed TERT siRNAs (Sigma Aldrich) or 500 nM Negative Control and HSATII LNA antisense oligonucleotides (Exiqon) were electroporated into COLO205 cells according to the Neon Transfection System (Invitrogen/Life Technology) instructions using the following conditions: 1600V; pulse width 10; 3 pulses. 500 nM Negative Control/HSATII LNA antisense oligonucleotides were transfected in HCT116 and SW620 cells using Lipofectamine 2000 (Invitrogen/Life Technologies) according to the manufacturer's instructions.

Metaphase Spreads and DNA-FISH

Cultured cells were trypsinized, resuspended in culture medium and kept in solution in a tube to work as a control for xenograft-derived single cell suspensions. Both preparations were treated with Karyomax Colcemid (Gibco/Life Technologies) at a final concentration of 20 ng/ml. After 4 h of incubation at 37° C., cells were pelleted and resuspended in ice-cold hypotonic solution (0.56% KCl). After 6 min of incubation at room temperature and a 4 min spin at 1000 rpm, pellets were fixed with methanol:acetic acid (3:1), incubated for 10 min at room temperature, spinned again and resuspended in 1 ml fixative. Cells were finally dropped on wet slides from a height of about 45 cm. After "aging" the chromosomes for 72 hours, slides were washed once with 2×SSC for 10 minutes, dehydrated in 70, 90, 100% ethanol for 2 min each and air dried. Probe (Sat.2 Repeat LNA fluorescein probe, Exiqon) was added at a concentration of 1.25 µM in a 50% formammide/2×SSC pH 7.0/10% dextran sulphate solution. DNA was denatured at 75° C. for 5 minutes, then hybridized for 4 h at 37° C. After three washes in 0.1×SSC at 50° C. for 5 min, two washes in 4×SSC/0.05% Tween at 37° C. for 5 min and one wash in PBS at room temperature for 5 min, slides were mounted with Vectashield Mounting Medium with DAPI (Vectorlabs). Pictures were taken at 1000× magnification with a Nikon 90i scope with color camera.

Immunofluorescence and Western Blot

For immunofluorescence, cells were fixed with 4% paraformaldehyde and washed with PBS. Fixed cells were then permeabilized with 1% NP40 in PBS, blocked with 3% BSA/2% goat serum, and then immunostained with anti-γH2AX primary antibody (Millipore, 05-636). Secondary fluorescent Alexa Fluor 594 antibody (Invitrogen/Life Technologies, A21125) was used for signal amplification. Nuclei were counter-stained with DAPI.

For histone analysis by Western blot, cell pellets ($1\times10^7$) were lysed in Triton extraction buffer (0.5% Triton X 100, 2 mM phenylmethylsulfonyl fluoride, 0.02% NaN$_3$) supplemented with protease and phosphatase inhibitors. After centrifuging at 2000 rpm for 10 minutes at 4° C., pellets were resuspended in 0.2 N HCl for acidic extraction overnight at 4° C. Following a 10 minutes spin at 4° C., supernatants were mixed with an equal volume of 50% trichloroacetic acid for histone precipitation. Once incubated on ice for 30 minutes, samples were centrifuged at maximum speed for 20 minutes at 4° C. The resulting pellets were washed twice in ice-cold acetone, air dried, resuspended in H$_2$O and quantified. Lysates (2.5 µg) were run on a SDS/4-15% polyacrylamide gel (Bio-Rad), transferred onto PVDF membranes (Invitrogen/Life Technologies), and immunoblots were visualized with a Western Lightning Plus chemiluminescence kit (PerkinElmer). The following primary antibodies were used: anti-γH2AX (Millipore, 05-636) and anti-H2AX (Millipore, 07-627).

Single Molecule Sequencing and Data Analysis

Purified RNA was subjected to digital gene expression (DGE) sample prepping and analysis on the HeliScope Single Molecule Sequencer from formerly Helicos BioSciences and now SeqLL, LLC (Woburn, Mass.). This method has been previously described (38). Briefly, single stranded cDNA was reverse transcribed from RNA with a dTU25V primer and the Superscript III cDNA synthesis kit (Invitrogen/Life Technoligies). Purified single stranded cDNA was denatured and then a poly-A tail was added to the 3' end using terminal transferase (New England Biolabs).

Purified DNA was subjected to the DNA sequencing sample prepping protocol from Helicos that has been previously described (39). Briefly, genomic DNA was sheared with a Covaris S2 acoustic sonicator producing fragments averaging 200 bps and ranging from 100 to 500 bps. Cleaned-up DNA was then denatured and a poly-A tail was added to the 3' end using terminal transferase (New England Biolabs).

Tailed cDNA or DNA were then hybridized to the sequencing flow cell followed by "Fill and Lock" and single molecule sequencing. Sequence reads were subjected to filtering for a minimum read length of 25 and removal of artifact reads followed by alignment of reads to the human genome (UCSC hg19) as well as the satellite reference library from Repeat Masker (4) using the indexDPgenomic aligner (38). RNA and genomic DNA sequence reads aligning to satellites were then normalized to total genomic alignments to obtain reads per million (rpm).

Estimating Satellite Copy-Number Changes from Whole-Genome Sequencing

We developed a computational method to detect amplification or deletions of satellite DNAs in high-depth sequencing data in cancer genomes by estimating enrichment/depletion of specific repetitive sequences relative to the genome of the matched normal tissue. Briefly, the approach relies on a custom alignment procedure to satellite sequence libraries (40). The enrichment/depletion ratio is estimated based on the total read counts uniquely associated with different repeat types, adjusted for the GC-bias estimated from reads mapped to copy-neutral regions and (optionally) copy-number changes expected based on the broad copy-number variation (CNV) events, such as aneuploidy (10 Mb CNV correction is shown in FIG. 11). The copy number profiles were inferred using a modified version of BIC-seq (41).

Example 1. Modified Northern Blot HSATII Assays

The highly repetitive nature of satellites precludes their precise quantitation and qualitative analysis using PCR-based RNA sequencing approaches. We have previously shown that PCR-independent single molecule next-generation sequencing (digital gene expression profiling, DGE; SeqLL) is uniquely sensitive and quantitative (7), but additional assays are desired that would be usable in a broad range of experimental conditions (FIG. 1A). To develop experimental models of HSATII expression, we therefore designed a modified Northern blot HSATII assay (FIG. 1B). Quantitation of DGE profiles and Northern blot signal intensity of matched primary gastrointestinal cancer specimens were highly correlated (FIGS. 1B and C). HSATII satellites encompass arrays of variable lengths of a 23-26 nt consensus sequence, derived from multiple different genomic locations (8). Northern blot probes generated a pattern of bands ranging from 30 nt to greater than 800 nt in size (FIG. 1B), consistent with that reported for murine minor satellites (9), human satellite 3 (10), and TERRA noncoding RNA (11).

Example 2. HSATII RNA Expression in Colorectal Cancer Cell Lines

We have previously demonstrated that mouse pancreatic cancers express high levels of major satellites, which are rapidly silenced following in vitro culture (4). Similarly, we observed that human colorectal cancer cell lines do not express HSATII under standard in vitro adherent (2D) culture conditions, but massively upregulate its expression when grown as tumor xenografts (FIG. 1D). To define experimental conditions that trigger HSATII expression, we tested multiple stimuli associated with cellular stress and tumorigenesis, including hypoxia, UV irradiation, heat shock, oxidative stress, overconfluence, treatment with demethylating agents, coculturing with stromal-derived feeder layers, and culture under anchorage-free conditions (FIGS. 6A-D). Remarkably, only culture under non-adherent 3D tumor sphere conditions or in soft agar led to robust induction of HSATII in 5 colorectal cancer cell lines (FIGS. 1E and 6C). A sixth line, COLO205, noteworthy for its growth as a mixed population of adherent and floating cells, was unique in expressing HSATII RNA under standard culture conditions. Together, these experimental systems enabled detailed analysis of satellite transcripts in human cancer cells.

Example 3. HSATII is Reverse Transcribed in Cancer Cells

As a routine procedure, we performed DNase I digestion of the RNA and unexpectedly observed that a portion of the HSATII signal derived from TRIzol extraction of tumor xenografts was DNA (FIG. 1F). The fact that the same cell lines cultured under 2D adherent conditions and subjected to multiple stimuli lacked HSATII DNA signal in Northern blots (FIGS. 1D, E and 6A-D) excluded the possibility of genomic DNA (gDNA) contamination. We therefore questioned whether deregulated satellite transcripts coexist with matched DNA fragments. Reverse transcription (RT) of other major repetitive elements, such as LINE1 (12) and telomeres (13, 14), is known in mammalian cells, and retrotransposons directly modulate the evolution of centromeres in plants (15, 16). RT-mediated integration of DNA sequences within centromeres has not been reported in mammals, with the exception of the marsupial tammar wallaby, whose exceptionally short centromeres harbor signatures of retroviral insertions alongside domains of satellite-rich sequences (17).

To directly test the possibility of HSATII RNA-to-DNA conversion, we first developed an in vitro transcription (IVT) assay taking advantage of a unique pericentromeric HSATII locus at chromosome 10q11 (HSATII-chr10), whose expression is most highly induced in cancer (4). Following IVT using T7 polymerase (FIG. 7A), ectopic single stranded HSATII RNA was introduced into 293T cells (FIG. 2A), which do not express this satellite under standard culture conditions (FIG. 7B). Presence in transfected cells of the expected 670 nt sense (S) HSATII RNA was readily detected using a single stranded complementary probe, peaking at 24 hours after transfection (FIGS. 2B and C). As anticipated, the HSATII S signal was completely abolished by treatment with RNase A, but not by DNase I, suggesting that S strand sequences were comprised entirely of RNA corresponding to the transfected IVT product. In contrast, probing the Northern blot for the antisense (AS) strand identified complementary species that were unaffected by RNAse A, but degraded by DNAse I. This strand selectivity suggested that exogenous RNA (S) is reverse transcribed exclusively into a complementary DNA (AS) strand, supporting the generation of RNA-derived-DNA (rdDNA) intermediates. Presence of DNA signal on only one strand further excludes the possibility of gDNA contamination. While the overall level of rdDNA was lower than that of HSATII RNA directly transfected into cells, the DNA signal persisted for up to 3 days, whereas the RNA was more rapidly depleted as cells proliferated (FIG. 2C). As control, transfection of comparable amounts of IVT GFP RNA (FIG. 7C) generated the expected RNA signal but showed no evidence of complementary rdDNA, nor did introduction of GFP RNA lead to the induction of either HSATII satellite RNA or DNA signal (FIGS. 2D and E).

Example 4. Nucleoside Analog RT Inhibitor (NRTI) Inhibits HSATII Reverse Transcription and Suppresses Cell Proliferation Having demonstrated the co-existence of transfected (FIG. 2B) as well as endogenous (FIG. 1F) HSATII RNA with potential rdDNA intermediates, we questioned whether these are dependent on RT activity. Given the CT-rich nature of HSATII template, we selected the nucleoside analog RT inhibitor (NRTI) 2′, 3′-dideoxycytidine (ddC) to test the consequences of suppressing RT activity in COLO205 cells, whose anchorage-independent growth is associated with baseline HSATII RNA expression (FIG. 1E). Indeed, exposure of cells to ddC for two weeks reduced the levels of endogenous HSATII rdDNA, while increasing the HSATII RNA species, as measured using a highly specific real-time PCR (qPCR) assay on HSATII-chr10 (FIG. 3A). While ddC had no effect on cells without endogenous HSATII expression under adherent growth conditions, it suppressed COLO205 cell proliferation (FIG. 8). Additional work using a combination of NRTIs ddC and d4T was effective in significantly reducing xenograft tumors from colon cancer cell line HCT116 (FIG. 9). Together, these observations are consistent with RT activity in HSATII-expressing cells, contributing to the generation of RNA/DNA intermediates from satellite transcripts.

Example 5. Suppression of hTERT Reduces HSATII rdDNA, Increases HSATII RNA

RT activity in mammalian cells is derived primarily from various retrotransposons and telomerase (hTERT). Genome-wide mapping studies have recently identified multiple binding sites within pericentromeric regions for the hTERT protein complex, including its RNA component TERC and shelterin (18, 19), raising the possibility that, in addition to chromosome ends, telomerase activity may also contribute to maintenance of intrachromosomal repeats. We first undertook cellular fractionation studies, demonstrating that HSATII RNA and DNA signals are restricted to the nucleus (FIG. 10A). RNA-immunoprecipitation (RIP) analysis of endogenous hTERT from extracts of two colon cancer cells (SW620 and HCT116), followed by reverse transcription and qPCR of HSATII-chr10, demonstrated significant enrichment of HSATII RNA with hTERT relative to control IgG (FIG. 3B and FIG. 10B). This enrichment was only observed when the cancer cells were grown as xenografts, but not under standard 2D in vitro culture conditions. As control, the coprecipitation of hTERT with TERC, its primary RNA template for telomere elongation was unaffected by culture conditions. We then knocked down hTERT using three different siRNA constructs in COLO205 cells (FIG. 10C), which express HSATII RNA at baseline. Consistent with the effect observed following exposure to the NRTI, suppression of hTERT induced a significant reduction in endogenous HSATII rdDNA and an increase in HSATII RNA (FIG. 3C). Together, these observations point to a role for telomerase in mediating reverse transcription of HSATII RNA into small DNA intermediates within the nucleus. While unexpected, this finding is consistent with emerging evidence of diverse roles for hTERT in the DNA damage response, transcriptional regulation, and small RNA biogenesis (20-23). However, we cannot exclude additional contributions from the multitude of cellular LINE-1 and retroviral encoded RTs, for which high specificity antibodies and inhibitors are not readily available.

Example 6. HSATII rdDNA Sequences May Reintegrate into the Genome

The existence of abundant HSATII rdDNA sequences in the nucleus led us to speculate whether these may be reintegrated into chromosomes, akin to LINE-1 mediated retrotransposition events observed in epithelial cancers, including colon carcinoma (24). To address this possibility, we first analyzed the dynamics of HSATII RNA and DNA expression using single molecule next-generation sequencing in SW620 colon cancer cells that were transitioned from 2D in vitro conditions to mouse xenografts. As expected, HSATII RNA was barely detectable at baseline under 2D culture, but it was induced 360-fold in the xenograft, and then promptly downregulated as xenograft-derived tumor cells were returned to 2D in vitro cultures (FIGS. 4A and 11A). Total cellular HSATII DNA copy number, which was already abundant at baseline, increased as much as 25-fold in xenografts and then remained stable upon subsequent return to culture in vitro (FIG. 4A). As control we analyzed the GSATII satellite which is structurally similar to HSATII but whose expression is not deregulated in cancer (4). GSATII expression within the same cell line showed minimal changes in RNA or DNA content as cells transitioned between in vitro and xenograft culturing conditions (FIG. 4A and Table 2). Fluorescent in-situ hybridization (FISH) applied to cells with amplified HSATII DNA sequences did not reveal detectable extrachromosomal elements, nor was hybridization signal detectable outside the five chromosomes (chr 2, 7, 10, 16 and 22) known to harbor long arrays of pericentromeric HSATII (FIG. 4B). Analysis of HSATII gDNA reads from the SW620 xenografts, using single molecule sequencing, showed that the additional HSATII sequences were distributed among the various endogenous HSATII pericentromeric loci (FIGS. 4C and 11B).

TABLE 2

Comprehensive summary of all satellite repeats identified by DNA- and RNA-seq in the indicated samples derived from SW620 cells. Values are expressed as reads per million (rpm).

| Sat. type | DNA CNV (rpm) | | | RNA DGE (rpm) | | |
|---|---|---|---|---|---|---|
| | Pre-xeno | Xeno | Post-xeno | Pre-xeno | Xeno | Post-xeno |
| ALR/Apha | 4922 | 66549 | 72474 | 2371 | 52602 | 5932 |
| HSATII | 518 | 13066 | 13143 | 19 | 6908 | 4 |
| BSR/Beta | 855 | 4962 | 5077 | 712 | 3501 | 1883 |
| (GAATG)n | 113 | 3949 | 3379 | 25 | 2395 | 37 |
| (CATTC)n | 135 | 3604 | 3069 | 19 | 2044 | 54 |
| SAR | 226 | 1786 | 2211 | 0 | 782 | 4 |
| GSATII | 545 | 565 | 730 | 305 | 904 | 2662 |
| ACRO1 | 15 | 1183 | 707 | 203 | 849 | 158 |
| SST1 | 168 | 659 | 651 | 254 | 506 | 41 |
| SATR1 | 84 | 525 | 595 | 127 | 428 | 62 |
| CER | 66 | 632 | 588 | 64 | 412 | 37 |
| SATR2 | 43 | 361 | 374 | 133 | 267 | 58 |
| HSATI | 3 | 230 | 216 | 0 | 192 | 4 |
| REP522 | 65 | 194 | 152 | 210 | 294 | 483 |
| GSAT | 44 | 112 | 112 | 127 | 140 | 233 |
| TAR1 | 643 | 113 | 104 | 235 | 209 | 187 |
| HSAT4 | 20 | 94 | 83 | 83 | 82 | 150 |
| D20S16 | 5 | 66 | 57 | 44 | 46 | 8 |
| LSAU | 16 | 59 | 53 | 19 | 46 | 37 |
| GSATX | 37 | 34 | 38 | 57 | 228 | 604 |
| MSR1 | 8 | 45 | 26 | 0 | 28 | 8 |
| HSAT5 | 2 | 37 | 25 | 13 | 32 | 4 |
| HSAT6 | 0 | 9 | 6 | 0 | 5 | 0 |
| SUBTEL_sa | 4 | 1 | 2 | 19 | 1 | 4 |

We then generated a cellular model to follow HSATII DNA copy gain over time by serially transplanting SW620 cells in vivo. Remarkably, over ten successive rounds of in vivo tumor initiation, progressive amplification of HSATII gDNA was evident at the two highest density HSATII pericentromeric regions on chromosome 16q (HSATII-chr16-1 and -2), using a real-time PCR-based copy number variation (CNV) assay (FIGS. 4D and 11C). An adjacent chromosomal region showed no transplantation-associated CNV changes, ruling out gains in 16q chromosomal arm or ploidy (FIG. 11D). Thus, the copy number gain at preexisting pericentromeric HSATII genomic loci appears to rise gradually over time, consistent with the possibility of multiple rDNA-mediated reintegration events.

To determine whether HSATII copy number gain occurs in primary human colon cancer, we analyzed CNV in 10 matched pairs of tumor and adjacent normal tissue. After correcting for chr16q arm loss or gain, significantly increased HSATII copy number was evident at the two independent HSATII loci tested in 5/10 (50%) colon cancers (FIGS. 4E and 11F). Among other cancers analyzed, 5/13 (38%) kidney cancers similarly showed HSATII gene copy gain (FIG. 11G).

Example 7. HSATII CNV Analysis Shows Genomic Gain in Human Cancer

To date, the complexity of sequencing and assembling genomic reads from highly repetitive sequences has precluded their detailed analysis in cancer through genome wide databases such as TCGA. To extend our study of focal HSATII loci to a genome-wide survey of human cancers, we used a satellite CNV algorithm to undertake computational analyses of whole genome sequencing (WGS) from TCGA along with a published database (25). In fully annotated genomic sequences of 38 colorectal cancers, 20 (53%) had statistically significant genomic gain of HSATII compared with their matched normal germline (FIG. 4F). HSATII amplification in these tumors was only partly overlapping with the changes affecting other satellite repeats (ALR/Alpha, TART, BSR/Beta and GSATII), which were considerably less prevalent. We note that the read depth obtained on these samples (>30×) provides high confidence CNV calls, but the intrinsic difficulty in PCR-based sequencing and subsequent alignment of repetitive sequences still poses considerable challenges. The high-stringency algorithm that we have applied here is likely to underestimate the true magnitude of gene copy changes. Correction of these data for large genomic alterations, comparable in size with HSATII stretches, returned consistent results (FIG. 12).

Example 8. Targeting HSATII with RNA Inhibits Tumor Sphere Formation

Using in vitro transcribed (IVT) HSATII RNA, transfection in colon cancer cell lines HCT116 and SW620 had negligible effects in 2D adherent culture where HSATII is not being expressed. However, when IVT HSATII RNA is used in the same cell line in non-adherent tumor sphere formation conditions, there is a significant reduction in tumor sphere capability (FIG. 13). Together, this indicates that HSATII stranded RNA has a significant effect on tumorigenesis using the tumor sphere assay.

Example 9. Targeting HSATII with LNAs Inhibits Cell Proliferation

As shown in Example 4, reverse transcription inhibition with ddC, a nucleoside analogue reverse transcriptase inhibitor (NRTI), impairs cell proliferation only in cancer cells displaying basal expression of HSATII. Locked nucleic acids (LNA) probes commercially purchased from Exiqon (GATTCCATTCGATGAT; SEQ ID NO:24) specifically targeting HSATII showed a similar effect in cancer cells. The fact that COLO205 cells, with their unique ability to produce satellite transcripts in 2D culture, were affected by antisense oligonucleotides against HSATII (FIG. 5A-C) suggested that HSATII itself, when expressed, plays a critical role in promoting tumor cell proliferation, thus representing a promising target suitable for therapeutic intervention in cancer.

The therapeutic efficacy of Locked Nucleic Acids targeting the HSATII satelite repeats was further evaluated against four human colorectal cancer cell lines (DLD1, SW620, HCT116, and HCT8) under non-adherent, and adherent growth conditions. Cell lines DLD1, and SW620 carry point mutations in the TP53 tumor suppressor protein (R241F, and R273H respectively). Cell lines HCT116 and HCT8 are wild type for TP53.

Locked nucleic acids (LNAs) were designed targeting the HSATII sequence that were different from the original Exiqon design:

HSATII LNA1:
(SEQ ID NO: 25)
+ A* + T* + G* + G*A*A*T*C*A*T*C*A*T* + C* + G* + A* + A

HSATIILNA2:
(SEQ ID NO: 26)
+ T* + G* + G*A*A*T*C*A*T*/iMe-dC/G*A*A*T* + G* + G* + A

-continued

Control LNA:
(SEQ ID NO: 27)
AACACGTCTATACGC

In the sequences above, an asterisk (*) before a base means phosphorothioate linkage, and +before a base in the oligo sequence denotes LNA modification of the base. "iMe-dC" represents 5-Methyl deoxyCytidine. The presence of 5-Methyl dC in CpG motifs can prevent or limit unwanted immune responses that otherwise occur if oligos are administered in vivo, which is of particular importance in antisense applications.

Cells were transfected with LNAs either targeting HSATII or with non-specific control Locked Nucleic Acids at 500 nM concentrations using Lipofectamine 2000 according to manufacturer recommended conditions. Cells were trypsinized 24 hours after transfection and seeded at concentration of 1000 cells per well in 96 well plates either in 2 dimensional or 3 dimensional culture conditions. For 2D conditions, the cells were transferred to cell culture treated 96 well plates and grown in RPMI+10% FBS. For 3D conditions, cells were grown in (RPMI+10% FBS+) in ultra-low attachment 96 well plates. Cells were observed to form non-adherent tumor spheres in 3D conditions.

The results showed that treatment with LNAs targeting HSATII led to significant growth inhibition in the TP53 mutant DLD1, and SW620 cell lines in non-adherent (3D) but not in adherent (2D) growth conditions (FIGS. 14A-D). The TP53 wild type cell lines HCT116 and HCT8 were refractory to this growth inhibition in both adherent, and non-adherent conditions (FIGS. 15A-D), suggesting a correlation of mutant TP53 status with HSATII LNA sensitivity.

It was hypothesized that LNA mediated targeting of HSATII leads to induction of programmed necrosis (necroptosis). To test this hypothesis, the RIP1K inhibitor Necrostatin-1 (Nec-1), which is known to inhibit necroptosis, was utilized. While treatment with HSATII targeted LNAs induced growth inhibition in DLD1 and SW620 cells in non-adherent conditions, this phenotype was rescued by treatment with Nec-1 (10 µM) (FIGS. 16A-D). These findings indicated that LNA-induced growth inhibition is mediated by the Necroptosis pathway, of which RIP1K is a major component.

The effect of reverse transcriptase inhibition was further evaluated on the colorectal cancer cell lines. Treatment with the reverse transcriptase inhibitor ddC (5 µM) led to significant growth inhibition in the DLD1 colon cancer cell line in 3 dimensional, but not in 2 dimensional culture conditions (FIGS. 17A-D). Furthermore, treatment with LNAs targeted to HSATII led to synergistic growth inhibition in DLD1, and SW620 cells when combined with ddC under 3D but not 2D culture conditions. Thus, there was a synergistic efficacy of reverse transcriptase inhibitors with HSATII LNAs.

Example 10. TP53 Loss Confers Cancer Cell Sensitivity to Reverse Transcriptase Inhibitors in HSATII High Cell Lines As the TP53 wild type colorectal cancer cell lines were resistant to HSATII targeting, experiments were performed to evaluate whether shRNA mediated knockdown of TP53 would sensitize these cells to HSATII targeting. Notably, Northern blot analysis had already identified HCT8 as a cell line that produced significant HSATII in 3D culture, and on the contrary, HCT116 did not express robust HSATII in 3D. Stable cell lines carrying either one of two shRNAs targeting TP53, or a non-target shRNA using lentiviral infection, were generated.

(SEQ ID NO: 28)
shTP53#1: GTCCAGATGAAGCTCCCAGAA (SEQ ID NO :29)
shTP53#2: CACCATCCACTACAACTACAT shRNA mediated knockdown of TP53 led to significantly increased sensitivity of HCT8 cells towards HSATII targeted LNAs under 3D growth conditions (FIGS. 18A-F). Interestingly, while HCT8 cells were normally resistant to ddC induced reverse transcriptase inhibition, TP53 knockdown in these cells led to significant growth inhibition in response to ddC under 3D culture conditions, but not under 2D conditions.

In contrast, shRNA-mediated knockdown of TP53 did not affect susceptibility of HCT116 cells to HSATII targeted LNAs, and ddC mediated reverse transcriptase inhibition, and these cell lines continued to show resistance in spite of TP53 knockdown in both 3D, and 2D culture conditions (FIGS. 19A-F). Together this suggests that HSATII expression and TP53 status are both important determinants of HSATII LNA and ddC sensitivity in cancer cell lines. Therefore, HSATII RNA-ISH and TP53 mutation status would be predictive biomarkers of efficacy.

REFERENCES

1. M. Plohl, A. Luchetti, N. Mestrovic, B. Mantovani, Gene 409, (2008).
2. H. Bierhoff, A. Postepska-Igielska, I. Grummt, Epigenetics 9, (2013).
3. A. Eymery, M. Callanan, C. Vourc'h, Int J Dev Biol 53, (2009).
4. D. T. Ting et al., Science 331, (2011).
5. A. Eymery et al., Nucleic Acids Res 37, (2009).
6. Q. Zhu et al., Nature 477, (2011).
7. F. Ozsolak et al., Nat Methods 7, (2010).
8. M. Jeanpierre, Ann Genet 37, (1994).
9. H. Bouzinba-Segard, A. Guais, C. Francastel, Proc Natl Acad Sci USA 103, (2006).
10. N. Rizzi et al., Mol Biol Cell 15, (2004).
11. C. M. Azzalin, P. Reichenbach, L. Khoriauli, E. Giulotto, J. Lingner, Science 318, (2007).
12. E. S. Lander et al., Nature 409, (2001).
13. T. de Lange, Nat Rev Mol Cell Biol 5, (2004).
14. P. Martinez, M. A. Blasco, Nat Rev Cancer 11, (2011).
15. J. Jiang, J. A. Birchler, W. A. Parrott, R. K. Dawe, Trends Plant Sci 8, (2003).
16. P. Neumann et al., Mob DNA 2, (2011).
17. D. M. Carone et al., Chromosoma 118, (2009).
18. C. Chu, K. Qu, F. L. Zhong, S. E. Artandi, H. Y. Chang, Mol Cell 44, (2011).
19. T. Simonet et al., Cell Res 21, (2011).
20. K. Masutomi et al., Proc Natl Acad Sci USA 102, (2005).
21. J. I. Park et al., Nature 460, (2009).
22. N. K. Sharma et al., Nucleic Acids Res 40, (2012).
23. Y. Maida et al., Nature 461, (2009).
24. E. Lee et al., Science 337, (2012).
25. A. J. Bass et al., Nat Genet 43, (2011).
26. J. Meyne et al., Chromosoma 99, (1990).
27. E. J. Richards, H. M. Goodman, F. M. Ausubel, Nucleic Acids Res 19, (1991).
28. A. L. Tek, J. Jiang, Chromosoma 113, (2004).

29. N. S. Zhdanova et al., Chromosome Res 13, (2005).
30. A. Villasante, J. P. Abad, M. Mendez-Lago, Proc Natl Acad Sci USA 104, (2007).
31. J. Cheng, A. Torkamani, Y. Peng, T. M. Jones, R. A. Lerner, Proc Natl Acad Sci USA 109, (2012).
32. G. P. Smith, Science 191, (1976).
33. Z. Cohen, E. Bacharach, S. Lavi, Oncogene 25, (2006).
34. J. C. Black et al., Cell 154, (2013).
35. A. H. Peters et al., Cell 107, (2001).
36. A. C. Martinez, K. H. van Wely, Carcinogenesis 32, (2011).
37. N. Crosetto et al., Nat Methods 10, (2013).
38. D. Lipson et al., Nat Biotechnol 27, (2009).
39. D. Pushkarev, N. F. Neff, S. R. Quake, Nat Biotechnol 27, (2009).
40. D. S. Day, L. J. Luquette, P. J. Park, P. V. Kharchenko, Genome Biol 11, (2010).
41. R. Xi et al., Proceedings of the National Academy of Sciences of the United States of America 108, (2011).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated oligonucleotide of 13-30 nucleotides that hybridizes to human satellite II (HSATII) wherein at least one nucleotide of the oligonucleotide is modified or is a nucleotide analogue, wherein the isolated oligonucleotide is complementary to at least 17 consecutive nucleotides of SEQ ID NO: 1; is complementary to at least 12 consecutive nucleotides of SEQ ID NO: 2; is complementary to at least 24 consecutive nucleotides of SEQ ID NO: 3; is complementary to at least 17 consecutive nucleotides of SEQ ID NO: 4; or is complementary to at least 11 consecutive nucleotides of SEQ ID NO: 5.

2. The isolated oligonucleotide of claim 1, wherein the oligonucleotide is 15 to 21 nucleotides in length.

3. The isolated oligonucleotide of claim 1, wherein at least one nucleotide of the oligonucleotide is a non-naturally occurring nucleotide analogue.

4. The isolated oligonucleotide of claim 1, wherein at least one nucleotide of the oligonucleotide comprises a 2' O-methyl.

5. The isolated oligonucleotide of claim 1, wherein the oligonucleotide comprises at least one ribonucleotide, at least one deoxyribonucleotide, or at least one bridged nucleotide.

6. The isolated oligonucleotide of claim 1, wherein one or more of the nucleotides of the oligonucleotide comprise 2'-fluoro-deoxyribonucleotides.

7. The isolated oligonucleotide of claim 1, wherein one or more of the nucleotides of the oligonucleotide comprise 2'-O-methyl nucleotides, ENA nucleotide analogues, or LNA nucleotides.

8. The isolated oligonucleotide of claim 1, wherein the nucleotides of the oligonucleotide comprise phosphorothioate internucleotide linkages between at least two nucleotides.

9. The isolated oligonucleotide of claim 1, wherein the isolated oligonucleotide is a gapmer or a mixmer.

10. A pharmaceutical composition comprising the isolated oligonucleotide of claim 1.

11. A method of treating a subject with cancer, wherein the cancer expresses high levels of HSATII RNA, the method comprising administering to the subject the isolated oligonucleotide of claim 1.

12. The method of claim 11, wherein the cancer is an epithelial cancer.

13. The method of claim 12, wherein the epithelial cancer is pancreatic, lung, breast, prostate, renal, ovarian, or colorectal cancer.

14. The method of claim 11, wherein the method comprises detecting a level of HSATII RNA in a sample from the cancer;
comparing the level of HSATII RNA in the sample to a reference level;
identifying a subject who has a cancer that has levels of HSATII RNA above the reference level; and
selecting the identified subject for treatment with the isolated oligonucleotide of claim 1.

15. The method of claim 11, wherein the cancer has a mutation in TP53.

16. The method of claim 15, wherein the method comprises detecting a level of TP53 protein in a sample from the cancer;
comparing the level of TP53 protein in the sample to a reference level;
identifying a subject who has a cancer that has levels of TP53 protein below the reference level; and
selecting the identified subject for treatment with the isolated oligonucleotide of claim 1.

17. The method of claim 12, wherein the method comprises detecting a mutation in a TP53 allele in a sample from the cancer; and
selecting the subject for treatment with the isolated oligonucleotide of claim 1.

18. The isolated oligonucleotide of claim 1, wherein the sequence of the isolated oligonucleotide comprises SEQ ID NO: 25.

19. The isolated oligonucleotide of claim 1, wherein the sequence of the isolated oligonucleotide consists of SEQ ID NO: 25.

20. The isolated oligonucleotide of claim 18, wherein the isolated oligonucleotide comprises one or more phosphorothioate internucleotide linkages and one or more LNA modifications.

21. The isolated oligonucleotide of claim 1, wherein the sequence of the isolated oligonucleotide comprises SEQ ID NO: 26.

22. The isolated oligonucleotide of claim 1, wherein the sequence of the isolated oligonucleotide consists of SEQ ID NO: 26.

23. The isolated oligonucleotide of claim 21, wherein the isolated oligonucleotide comprises one or more phosphorothioate internucleotide linkages and one or more LNA modifications.

24. A locked nucleic acid (LNA) oligonucleotide of 13-30 nucleotides that hybridizes to human satellite II (HSATII) wherein the LNA oligonucleotide is complementary to at least 17 consecutive nucleotides of SEQ ID NO: 1; is complementary to at least 12 consecutive nucleotides of SEQ ID NO: 2; is complementary to at least 24 consecutive nucleotides of SEQ ID NO: 3; is complementary to at least 17 consecutive nucleotides of SEQ ID NO: 4; or is complementary to at least 11 consecutive nucleotides of SEQ ID NO: 5.

25. The LNA oligonucleotide of 24, wherein the sequence of the isolated oligonucleotide consist of SEQ ID NO: 25 or SEQ ID NO: 26.

* * * * *

SEQUENCE LISTING

```
<160> NUMBER OF SEQ ID NOS: 29

<210> SEQ ID NO 1
<211> LENGTH: 170
<212> TYPE: DNA
<213> ORGANISM: Homo sapiens

<400> SEQUENCE: 1
ccattcgatt ccattcgatg attccattcg attccattcg atgatgattc cattcgattc      60
cattcgatga ttccattcga ttccattcga tgatgattcc attcgattcc attcgatgat    120
tccattcgat tccattcgat gatgattcca ttcgattcca ttcgatgatt                170

<210> SEQ ID NO 2
<211> LENGTH: 23
<212> TYPE: DNA
<213> ORGANISM: Artificial Sequence
<220> FEATURE:
<223> OTHER INFORMATION: oligo target sequence

<400> SEQUENCE: 2
ccattcgatt ccattcgatg att                                              23

<210> SEQ ID NO 3
<211> LENGTH: 26
<212> TYPE: DNA
<213> ORGANISM: Artificial Sequence
<220> FEATURE:
<223> OTHER INFORMATION: oligo target sequence

<400> SEQUENCE: 3
ccattcgatt ccattcgatg atgatt                                           26

<210> SEQ ID NO 4
<211> LENGTH: 49
<212> TYPE: DNA
<213> ORGANISM: Artificial Sequence
<220> FEATURE:
<223> OTHER INFORMATION: oligo target sequence

<400> SEQUENCE: 4
ccattcgatt ccattcgatg attccattcg attccattcg atgatgatt                  49

<210> SEQ ID NO 5
<211> LENGTH: 21
<212> TYPE: DNA
<213> ORGANISM: Artificial Sequence
<220> FEATURE:
<223> OTHER INFORMATION: oligo target sequence
```

<400> SEQUENCE: 5
cattcgattc cattcgatga t                                              21

<210> SEQ ID NO 6
<211> LENGTH: 21
<212> TYPE: DNA
<213> ORGANISM: Artificial Sequence
<220> FEATURE:
<223> OTHER INFORMATION: oligo target sequence

<400> SEQUENCE: 6
atcatcgaat ggaatcgaat g                                              21

<210> SEQ ID NO 7
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 7
cattcgattc cattcgatga t                                              21

<210> SEQ ID NO 8
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 8
atcatcgaat ggaatcgaat g                                              21

<210> SEQ ID NO 9
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 9
cgcgcttctc gttggggtct t                                              21

<210> SEQ ID NO 10
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 10
aagaccccaa cgagaagcgc g                                              21

<210> SEQ ID NO 11
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 11
ttgcgtgtca tccttgcgca gg                                             22

<210> SEQ ID NO 12
<211> LENGTH: 23

```
<212> TYPE: DNA
<213> ORGANISM: Artificial Sequence
<220> FEATURE:
<223> OTHER INFORMATION: synthetically generated oligonucleotide

<400> SEQUENCE: 12
gcattcaatt cattagatga cgg                                              23

<210> SEQ ID NO 13
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 13
ccttgacccg aatgcaatca                                                  20

<210> SEQ ID NO 14
<211> LENGTH: 24
<212> TYPE: DNA
<213> ORGANISM: Artificial Sequence
<220> FEATURE:
<223> OTHER INFORMATION: synthetically generated oligonucleotide

<400> SEQUENCE: 14 tctaaccta actgagaagg gcgt                                              24

<210> SEQ ID NO 15
<211> LENGTH: 24
<212> TYPE: DNA
<213> ORGANISM: Artificial Sequence
<220> FEATURE:
<223> OTHER INFORMATION: synthetically generated oligonucleotide

<400> SEQUENCE: 15
tgctctagaa tgaacggtgg aagg                                             24

<210> SEQ ID NO 16
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 16
ccattcgtta atgcctttcg                                                  20

<210> SEQ ID NO 17
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 17
cacgaatgga atcattgtcg                                                  20

<210> SEQ ID NO 18
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 18
```

-continued tccattcgag gattccactc                                              20

<210> SEQ ID NO 19
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 19
caaagggaag caaaggaaat c                                            21

<210> SEQ ID NO 20
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 20
ggggtaaaag ggcatgtttt                                              20

<210> SEQ ID NO 21
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 21
ctgaagaagc ccactcaagg                                              20

<210> SEQ ID NO 22
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 22
ctcttccagc cttccttcct                                              20

<210> SEQ ID NO 23
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 23
agcactgtgt tggcgtacag                                              20

<210> SEQ ID NO 24
<211> LENGTH: 16
<212> TYPE: DNA
<213> ORGANISM: Artificial Sequence
<220> FEATURE:
<223> OTHER INFORMATION: synthetically generated oligonucleotide

<400> SEQUENCE: 24
gattccattc gatgat                                                  16

<210> SEQ ID NO 25
<211> LENGTH: 17
<212> TYPE: DNA
<213> ORGANISM: Artificial Sequence

```
<220> FEATURE:
<223> OTHER INFORMATION: synthetically generated oligonucleotide

<400> SEQUENCE: 25
atggaatcat catcgaa                                                   17

<210> SEQ ID NO 26
<211> LENGTH: 17
<212> TYPE: DNA
<213> ORGANISM: Artificial Sequence
<220> FEATURE:
<223> OTHER INFORMATION: synthetically generated oligonucleotide

<400> SEQUENCE: 26
tggaatcatc gaatgga                                                   17

<210> SEQ ID NO 27
<211> LENGTH: 15
<212> TYPE: DNA
<213> ORGANISM: Artificial Sequence
<220> FEATURE:
<223> OTHER INFORMATION: synthetically generated oligonucleotide

<400> SEQUENCE: 27
aacacgtcta tacgc                                                     15

<210> SEQ ID NO 28
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 28
gtccagatga agctcccaga a                                              21

<210> SEQ ID NO 29
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 29
caccatccac tacaactaca t                                              21
```